(12) United States Patent
Goswami et al.

(10) Patent No.: US 9,044,332 B2
(45) Date of Patent: Jun. 2, 2015

(54) TOE JOINT REPLACEMENT MODELS

(71) Applicant: Wright State University, Dayton, OH (US)

(72) Inventors: Tarun K. Goswami, Beavercreek, OH (US); Allison L. Van Horn, Centerville, OH (US); Alexander O. Sheets, Dayton, OH (US)

(73) Assignee: Wright State University, Dayton, OH (US)

( * ) Notice: Subject to any disclaimer, the term of this patent is extended or adjusted under 35 U.S.C. 154(b) by 0 days.

(21) Appl. No.: 13/655,269

(22) Filed: Oct. 18, 2012

(65) Prior Publication Data

US 2013/0046387 A1    Feb. 21, 2013

Related U.S. Application Data

(62) Division of application No. 12/748,405, filed on Mar. 27, 2010, now abandoned.

(60) Provisional application No. 61/163,920, filed on Mar. 27, 2009.

(51) Int. Cl.
*A61F 2/42* (2006.01)
*A61F 2/30* (2006.01)

(52) U.S. Cl.
CPC ........... *A61F 2/4225* (2013.01); *A61F 2/30734* (2013.01); *A61F 2/30749* (2013.01); *A61F 2002/30205* (2013.01); *A61F 2002/30224* (2013.01); *A61F 2002/30331* (2013.01); *A61F 2002/30332* (2013.01); *A61F 2002/30387* (2013.01); *A61F 2002/30405* (2013.01); *A61F 2002/30497* (2013.01); *A61F 2002/305* (2013.01); *A61F 2002/30579* (2013.01); *A61F 2002/3085* (2013.01); *A61F 2002/30878* (2013.01); *A61F 2002/30884* (2013.01); *A61F 2002/4235* (2013.01); *A61F 2220/0008* (2013.01); *A61F 2220/0025* (2013.01); *A61F 2220/0033* (2013.01); *A61F 2230/0067* (2013.01); *A61F 2230/0069* (2013.01)

(58) Field of Classification Search
CPC ........... A61F 2/4241; A61F 2002/4241; A61F 2002/4243; A61F 2002/4246; A61F 2002/4248; A61F 2002/4225
USPC .............................................. 623/21.15–21.17
See application file for complete search history.

(56) References Cited

U.S. PATENT DOCUMENTS

| | | | | |
|---|---|---|---|---|
| 5,370,695 A | * | 12/1994 | Meuli et al. | 623/23.53 |
| 2003/0114934 A1 | * | 6/2003 | Steinberg | 623/22.17 |
| 2004/0225367 A1 | * | 11/2004 | Glien et al. | 623/19.14 |
| 2005/0216090 A1 | * | 9/2005 | O'Driscoll et al. | 623/20.32 |
| 2006/0074492 A1 | * | 4/2006 | Frey | 623/21.15 |

* cited by examiner

*Primary Examiner* — Bruce E Snow
*Assistant Examiner* — Brian Dukert
(74) *Attorney, Agent, or Firm* — Dinsmore & Shohl LLP

(57) ABSTRACT

In various embodiments, provided are implantable devices for replacing all or a portion of a metatarsophalangeal joint, comprising (i) a metatarsal component comprising a substantially convex bearing surface; or (ii) a phalanx component comprising a substantially concave bearing surface; or (iii) both. In various embodiments, also provided are methods of treating hallux valgus by replacing all or a portion of a metatarsophalangeal joint with one or more of the provided implantable devices.

11 Claims, 32 Drawing Sheets

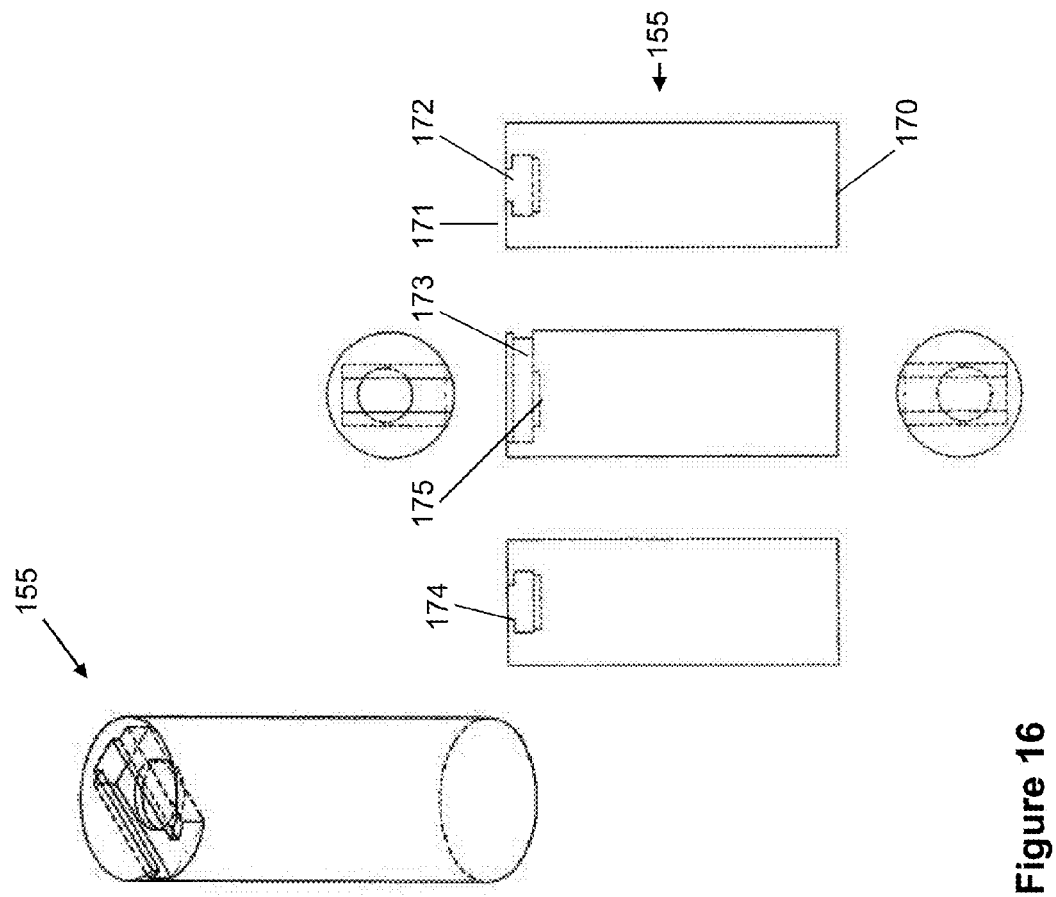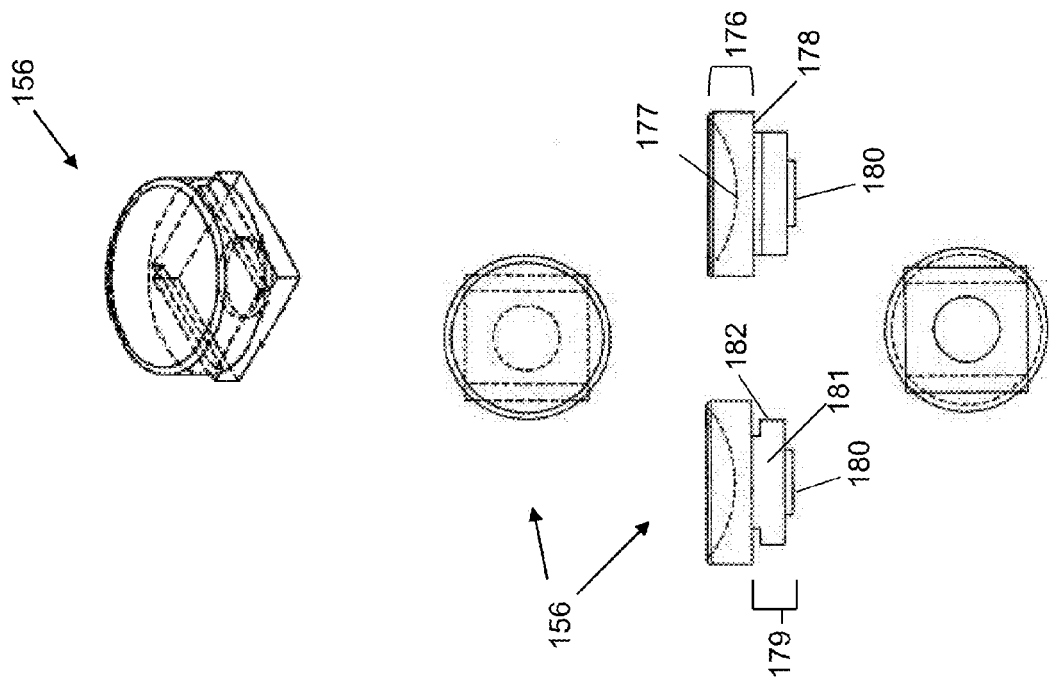
Figure 16

TOE JOINT REPLACEMENT MODELS

CROSS REFERENCE TO RELATED APPLICATION

This application is a division of U.S. patent application Ser. No. 12/748,405, filed Mar. 27, 2010, which claims the benefit of priority under 35 U.S.C. Section 119(e) of U.S. Provisional Patent Application No. 61/163,920, filed Mar. 27, 2009, all of which are hereby incorporated in their entireties

BACKGROUND

Hallux valgus is characterized as a deformity of the great toe (hallux) and first metatarsophalangeal joint, wherein the first metatarsal is medially deviated, the great toe is laterally deviated and/or rotated on the head of the metatarsal, the plantar pad and sesamoids are displaced with the toe, and the ligaments on the medial side of the metatarsophalangeal joint are stretched. The position of the great toe with respect to the second toe can be overriding, underriding, abutting, or without contact. Thus, hallux valgus can involve transverse plane deformities (hallux abductus), or frontal and transverse plane deformities (hallux abductovalgus). With respect to deformities in the transverse plane, the angle between the longitudinal axis of the metatarsals of the first and second toes (intermetatarsal angle) typically deviates beyond the normal range of 8-12°. With respect to deformities in the frontal plane, the angle between the longitudinal axis of the metatarsal and proximal phalanx of the great toe (hallux valgus angle) typically deviates beyond the normal upper limit of 15-20°.

In addition to physical deformity, hallux valgus is often accompanied by formation of a callous, bursa, or bunion over the first metatarsal head, pain in the first metatarsophalangeal joint during ambulation, pain in the metatarsal head, and combinations thereof.

Hallux valgus is estimated to affect more than 43 million people in the United States, with incidence more predominate in females, those older than 60 years of age, teenagers who wear high heels, and athletes. It can develop due to numerous factors, including biomechanical instability (e.g., excessive protonation), arthritic/metabolic conditions (e.g., osteo/rheumatoid arthritis), neuromuscular disease (e.g., multiple sclerosis), trauma (e.g., soft-tissue sprains, dislocations, and sports-related injuries), and structural deformities (e.g., abnormal metatarsal length). Additionally, there tends to be familial disposition to developing hallux valgus.

Development of hallux valgus typically occurs in four stages. See Root, M L, "Normal and Abnormal Function of the Foot," Vol. 2, *Clinical Biomechanics* (1977). The first stage is associated with lateral subluxation (partial or complete dislocation) of the proximal phalanx. The second stage is associated with increased abduction of the hallux in the transverse and/or frontal planes. The third stage is associated with additional subluxation at the first metatarsophalangeal joint. The fourth stage is associated with dislocation of the first metatarsophalangeal joint.

Hallux valgus is a complex deformity and various approaches to treating or correcting the deformity may be available. For example, when hallux valgus is in its early stages, or where surgical correction is contraindicated, braces, straps, splints, orthotics, or combinations thereof may be used to manage progression of the deformity and relieve the associated symptoms. However, surgery is the only means of correcting the deformity.

The first surgical treatment to address hallux valgus dates to 1881 when an osteotomy procedure involving an incision medial to the extensor hallucis longus, followed by incision of the periosteum, removal of exostosis, removal of bone from behind the caputulum of the metatarsus, and suturing of the bone. Since this forerunning procedure, numerous other procedures have been developed, all with the goal of addressing the deformity with minimal complications. Such surgical procedures, while varying depending upon the nature of the deformity and particular needs of the patient, generally allow for establishment of a congruous first metatarsophalangeal joint, reduction of the intermetatarsal angle, realignment of the sesamoids, realignment of the hallux to a rectus (rather than an abductus) position, and maintenance or increase of the range of motion of the first metatarsophalangeal joint.

Typical surgical procedures involve one or more of osteotomy of the metatarsal head, osteotomy of the metatarsal shaft or base, fusion of the metatarsophalangeal joint, resectional arthroplasty, resectional arthroplasty with a partial (hemi) implant, and resectional arthroplasty with a total implant. With respect to procedures involving an implant, numerous devices for use therewith are known in the art. For example, known hemi arthroplasty devices, which are typically used when the proximal phalanx is degenerated but the metatarsal head is intact, include the BioPro® hemi toe implant (BioPro, Inc., Port Huron, Mich.); Futura™ Metal Hemi Toe implant (Tornier, Edina, Minn.); K2™ Hemi Toe Implant System (Integra LifeSciences Corp., Plainsboro, N.J.); and Swanson™ Great Toe Implant (Wright Medical Technology, Inc., Arlington, Tenn.), all of which are depicted in FIG. 1A. Examples of known double-stemmed hinges, which are typically used when both the proximal phalanx and the metatarsal head are degenerated, include the Swanson™ Flexible Hinge Toe implant (Wright Medical Technology, Inc., Arlington, Tenn.); GAIT Implant™ (Sgarlato Med, San Jose, Calif.); and Futura™ Flexible Great Toe implant (Tornier, Edina, Minn.), all of which are depicted in FIG. 1B. In addition, examples of known two-component devices, which are also typically used when both the proximal phalanx and the metatarsal head are degenerated, include the Total ToeTm System (Biomet, Warsaw, Ind.); Bio-Action™ Great Toe Implant (Osteomed, Inc., Addison, Tex.); ReFlexion™ $1^{st}$ MPJ Implant System (Osteomed, Inc., Addison, Tex.); and KGTI™ Kinetik Great Toe Implant System (Integra LifeSciences Corp., Plainsboro, N.J.), all of which are depicted in FIG. 1C.

Along with the knowledge in the art of numerous implant devices is the knowledge of numerous problems associated with such devices. Examples include, but are not limited to, shearing stress, loosening of the device, fragmentation, fracture through the proximal phalanx, breakage of hinged implants at the hinge, misalignment, recurrence of deformity, limited joint motion, development of plantar keratosis, development of tenderness around the joint, development of long flexor tendonitis, development of metatarsalgia, and development of metallosis. Accordingly, there is need in the art for improved implant devices for use in correcting hallux valgus. Moreover, there is need in the art for devices that are aligned and articulate in a manner consistent with natural motion of the metatarsophalangeal joint, that resist torsion forces applied to the device, and that are designed to be implanted without complex assembly, positioning, or other manipulation by the surgeon.

SUMMARY

Embodiments of the present invention provide novel implantable devices used to replace all or a portion of a joint of the human toe. In some embodiments, the implantable devices are designed to replace all or a portion of the metatarsophalangeal joint. In some embodiments, the devices replace all or a portion of the metatarsal head and function as the metatarsal component of the metatarsophalangeal joint. In some embodiments, the devices replace all or a portion of the proximal end of the proximal phalanx and function as the phalanx component of the metatarsophalangeal joint.

In various embodiments, the implantable devices replace all or a portion of a metatarsophalangeal joint and comprise (i) a metatarsal component for surgical implantation into the distal end of a metatarsal bone, comprising a metatarsal articulation member comprising a substantially convex bearing surface; or (ii) a phalanx component for surgical implantation into the proximal end of a proximal phalanx bone, comprising a phalanx articulation member comprising a substantially concave bearing surface; or (iii) a metatarsal component for surgical implantation into the distal end of a metatarsal bone, comprising a metatarsal articulation member comprising a substantially convex bearing surface; and a phalanx component for surgical implantation into the proximal end of a proximal phalanx bone, comprising a phalanx articulation member comprising a substantially concave bearing surface. In some embodiments, the metatarsal component and the phalanx component are adapted to cooperatively engage when implanted such that the metatarsal articulation member and the phalanx articulation member may move with respect to each other and collectively serve as a prosthetic metatarsophalangeal joint.

In various embodiments, also provided are methods of treating hallux valgus, comprising replacing all or a portion of a metatarsophalangeal joint with implantable devices selected from: (i) a metatarsal component for surgical implantation into the distal end of a metatarsal bone, comprising a metatarsal articulation member comprising a substantially convex bearing surface; (ii) a phalanx component for surgical implantation into the proximal end of a proximal phalanx bone, comprising a phalanx articulation member comprising a substantially concave bearing surface; or (iii) a metatarsal component for surgical implantation into the distal end of a metatarsal bone, comprising a metatarsal articulation member comprising a substantially convex bearing surface; and a phalanx component for surgical implantation into the proximal end of a proximal phalanx bone, comprising a phalanx articulation member comprising a substantially concave bearing surface.

These and additional features of the invention will become apparent in the course of the following detailed description.

BRIEF DESCRIPTION OF THE DRAWINGS

A more complete appreciation of the invention and the many embodiments thereof will be readily obtained as the same becomes better understood by reference to the following detailed description when considered in connection with the accompanying drawings, wherein:

FIGS. 14-16 illustrate an additional example of an implantable two-component device and elements thereof;

DETAILED DESCRIPTION

Figure 1:
FIG. 1 illustrates various examples of implantable devices known in the art.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art. Similarly, the present invention should not be considered limited to the specific examples described herein, but rather should be understood to cover all aspects of the invention. Various modifications and equivalents, as well as numerous structures and devices to which the present invention may be applicable will be readily apparent to those of skill in the art. Those skilled in the art will understand that various changes may be made without departing from the scope of the invention, which is not to be considered limited to what is described in the specification.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Additionally, the disclosure of any ranges in the specification and claims are to be understood as including the range itself and also anything subsumed therein, as well as endpoints. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

Provided are implantable devices used to replace all or part of a human toe joint. In some embodiments, the devices replace all or a portion of the metatarsophalangeal joint, said devices being designed to be positioned during implantation such that when the muscles and tendons of the foot exert a force on the natural phalanx and metatarsal bones, the components of the device provide functional cooperation that emulates the desired and permissible movements of the metatarsophalangeal joint. In some embodiments, the provided devices align and articulate in a manner consistent with natural motion of the joint. In some embodiments, the devices are adapted to be implanted without complex assembly, positioning, or other manipulation by the surgeon.

In various embodiments, the implantable devices replace all or a portion of a metatarsophalangeal joint and comprise (i) a metatarsal component for surgical implantation into the distal end of a metatarsal bone, comprising a metatarsal articulation member comprising a substantially convex bearing surface; or (ii) a phalanx component for surgical implantation into the proximal end of a proximal phalanx bone, comprising a phalanx articulation member comprising a substantially concave bearing surface; or (iii) a metatarsal component for surgical implantation into the distal end of a metatarsal bone, comprising a metatarsal articulation member comprising a substantially convex bearing surface; and a phalanx component for surgical implantation into the proximal end of a proximal phalanx bone, comprising a phalanx articulation member comprising a substantially concave bearing surface. Accordingly, these devices can be used for total joint replacement when a metatarsal and a phalanx component are implanted, or for partial (hemi) replacement when only one of the metatarsal and phalanx component is implanted.

In various embodiments, the implantable devices replace all or a portion of a metatarsophalangeal joint and comprise: (i) a metatarsal component for surgical implantation into the distal end of a metatarsal bone, comprising a metatarsal articulation member comprising a substantially convex bearing surface; a base member adapted to be fixed within the metatarsal bone; and a locking member adapted to mechanically join the metatarsal articulation member to the base member; and (ii) a phalanx component for surgical implantation into the proximal end of a proximal phalanx bone, comprising a phalanx articulation member comprising a substantially concave bearing surface; a base member adapted to be fixed within the phalanx bone; and a locking member adapted to mechanically join the phalanx articulation member to the base member; wherein the metatarsal component and the phalanx component are adapted to cooperatively engage when implanted such that the metatarsal articulation member and the phalanx articulation member may move with respect to each other and collectively serve as a prosthetic metatarsophalangeal joint.

In various embodiments, the implantable devices replace all or a portion of a metatarsophalangeal joint and comprise: (i) a metatarsal component for surgical implantation into the distal end of a metatarsal bone, comprising a metatarsal articulation member comprising a substantially convex bearing surface; and a locking member comprising a screw thread adapted to fix the metatarsal component in the metatarsal bone; and (ii) a phalanx component for surgical implantation into the proximal end of a proximal phalanx bone, comprising a phalanx articulation member comprising a substantially concave bearing surface; and a locking member comprising a screw thread adapted to fix the phalanx component in the phalanx bone; wherein the metatarsal component and the phalanx component are adapted to cooperatively engage when implanted such that the metatarsal articulation member and the phalanx articulation member may move with respect to each other and collectively serve as a prosthetic metatarsophalangeal joint.

In various embodiments, the implantable devices replace all or a portion of a metatarsophalangeal joint and comprise: (i) a metatarsal component for surgical implantation into the distal end of a metatarsal bone, comprising a metatarsal articulation member comprising a substantially convex parabolic bearing surface terminating at equidistantly positioned ends; and (ii) a phalanx component for surgical implantation into the proximal end of a proximal phalanx bone, comprising a phalanx articulation member comprising a substantially concave bearing surface; wherein the metatarsal component and the phalanx component are adapted to cooperatively engage when implanted such that the metatarsal articulation member and the phalanx articulation member may move with respect to each other and collectively serve as a prosthetic metatarsophalangeal joint.

The provided devices may be comprised of any material suitable for implant devices. For example, materials that comply with ASTM F75-01, F90-01, F136-02a, and other applicable specifications. In some embodiments suitable materials of composition may be selected from ultra-high molecular weight polyethylene ("UHMWPE"), stainless steel (including but not limited to SS 316L), titanium, titanium alloys (including but not limited to Ti-6A1-4V), chromium-cobalt-molybdenum alloys, pyrocarbon, and combinations thereof. Properties of some suitable materials are shown in Table 1. In some embodiments, a device may comprise a coating for enhancing bone growth. For example, a suitable coating may be titanium plasma spray. In some embodiments, a device may be partially or completely formed from pyrocarbon. In some embodiments, the pyrocarbon is coated with titanium plasma spray. In some embodiments, UHMWPE is the material of composition used for the metatarsal bearing surface, the phalanx bearing surface, or both.

TABLE 1

| Material | Elastic Modulus | Tensile Strength | Density | Modulus of Shear | Yield Strength |
|---|---|---|---|---|---|
| UHMWPE | 1258 MPa | 45.8 MPa | 932 kg/m 3 | 11-13 MPa | 23.56 MPa |
| Stainless Steel 316L | 200 GPa | 485 MPa | 8027 kg/m 3 | 82 GPa | 170 MPa |
| Ti-6Al-4V | 113.8 GPa | 950 MPa | 4430 kg/m 3 | 44 GPa | 880 MPa |
| Pyrocarbon | 25 GPa | 420 MPa | 1700 kg/m 3 | — | 345 MPa |

Referring to FIGS. 2-10, illustrated are various examples of implantable devices of the invention which are designed to replace all or a portion of a metatarsophalangeal joint. Such devices comprise one or more of: (i) a metatarsal component for surgical implantation into the distal end of a metatarsal bone, comprising a metatarsal articulation member comprising a substantially convex bearing surface and a stem adapted to receive a portion of a locking member; a base member adapted to be fixed within the metatarsal bone, the base member comprising a cavity adapted to receive at least a portion of the stem and a portion of the locking member; and a locking member adapted to be received by the stem and cavity; wherein when the stem is received in the cavity and the locking member is received by the stem and cavity, the metatarsal articulation member is mechanically joined to the base member; and (ii) a phalanx component for surgical implantation into the proximal end of a proximal phalanx bone, comprising a phalanx articulation member comprising a substantially concave bearing surface and a stem adapted to receive a portion of a locking member; a base member adapted to be fixed within the phalanx bone, the base member comprising a cavity adapted to receive at least a portion of the stem and a portion of the locking member; and a locking member adapted to be received by the stem and cavity; wherein when the stem is received in the cavity and the locking member is received by the stem and cavity, the phalanx articulation member is mechanically joined to the base member.

In those embodiments wherein one of the components is implanted, the chosen component is adapted to cooperatively engage with and move with respect to either the proximal end of the proximal phalanx bone or the distal end of the metatarsal bone. In those embodiments wherein both of the components are implanted, the metatarsal component and the phalanx component are adapted to cooperatively engage such that the metatarsal articulation member and the phalanx articulation member move with respect to each other and collectively serve as a prosthetic metatarsophalangeal joint.

Figure 2:
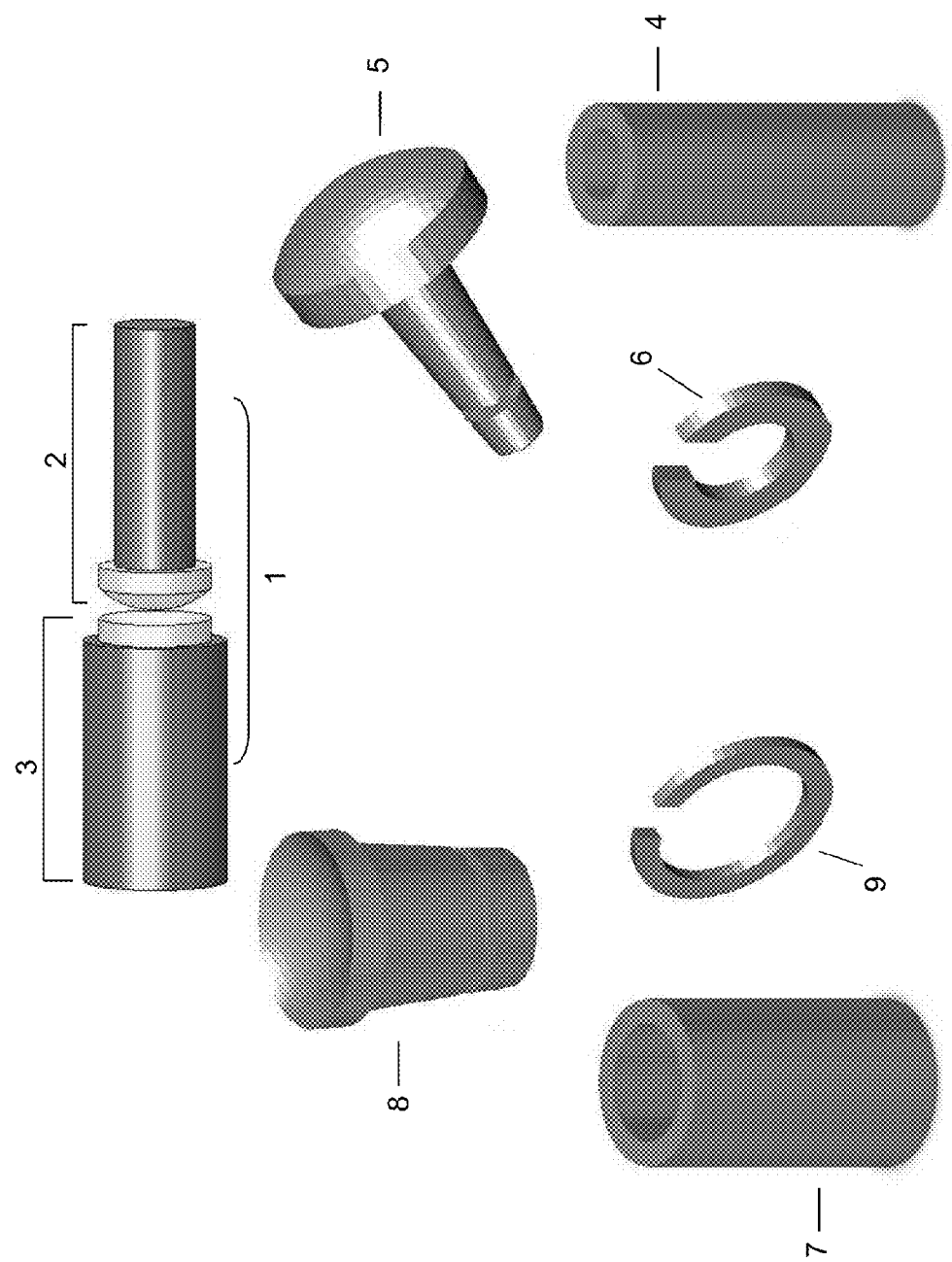
FIGS. 2-4 illustrate one example of an implantable two-component device and elements thereof.

Referring to FIG. 2, one example of a two-component implant device 1 comprises a metatarsal component 2 and a phalanx component 3. The metatarsal component 2 is designed to be implanted into the distal end of a resected metatarsal bone to replace all or a portion of the metatarsal head and function as the metatarsal component of the metatarsophalangeal joint. The metatarsal component 2 comprises a base member 4, a metatarsal articulation member 5, and a locking member 6. The base member 4 may be of any suitable length and dimension to allow for fixation within the metatarsal bone, and may be fixed by any medically suitable means. In some embodiments, the base member 4 is designed to be implanted in approximately one third of the length of the metatarsal bone. In some embodiments, it may be fixed with bone cement.

The phalanx component 3 is designed to be implanted into the proximal end of a resected proximal phalanx bone to replace all or a portion of the proximal end of the proximal phalanx and function as the phalanx component of the metatarsophalangeal joint. The phalanx component 3 comprises a base member 7, a phalanx articulation member 8, and a locking member 9. The base member 7 may be of any suitable length and dimension to allow for fixation within the phalanx bone, and may be fixed by any medically suitable means. In some embodiments, the phalanx component 3 is designed to be implanted in approximately half of the length of the phalanx bone. In embodiments, it may be fixed with bone cement.

In some embodiments, one or both of the metatarsal component 2 and the phalanx component 3 are implanted into the human foot to replace all or a portion of the metatarsophalangeal joint. In some embodiments, one or both components 2, 3 may be implanted in a primary resectional arthroplasty procedure, in a revision arthroplasty procedure performed to replace or compensate for a failed implant, or combinations thereof. In some embodiments, one or both components 2, 3 are implanted in a primary resectional arthroplasty procedure. In some embodiments, each component 2, 3 implanted may be selected from small, medium, or large sizes as necessary to approximate the anatomy of the subject. In some embodiments, the components 2, 3 may comprise one or more dimensions as set forth in Table 2. In some embodiments, each component 2, 3 and elements thereof may be customized to the anatomy of the subject.

TABLE 2

|  | Dimension (mm) |
|---|---|
| Metatarsal | |
| Base Member Length | 22-26 |
| Base Member Outer Diameter Top | 7-10 |
| Base Member Outer Diameter Bottom | 7-10 |
| Articulation Member Length (Excluding Head Portion) | 12-16 |
| Articulation Member Outer Diameter Top | 4-7 |
| Articulation Member Outer Diameter Bottom | 3-6 |
| Head Portion Diameter | 10-13 |
| Locking Member Outer Diameter | 4-7 |
| Locking Member Inner Diameter | 2-5 |
| Locking Member Thickness | 0.5 |
| Head Portion Height | 2 |
| Phalanx | |
| Base Member Length | 18-22 |
| Base Member Outer Diameter Top | 10-13 |
| Base Member Outer Diameter Bottom | 10-13 |
| Articulation Member Length (Excluding Head Portion) | 10-15 |
| Articulation Member Outer Diameter Top | 7-10 |
| Articulation Member Outer Diameter Bottom | 6-8 |
| Head Portion Diameter | 10-13 |
| Locking Member Outer Diameter | 7-10 |
| Locking Member Inner Diameter | 5-8 |
| Locking Member Thickness | 0.5 |
| Head Portion Depth | 2 |

Figure 3:
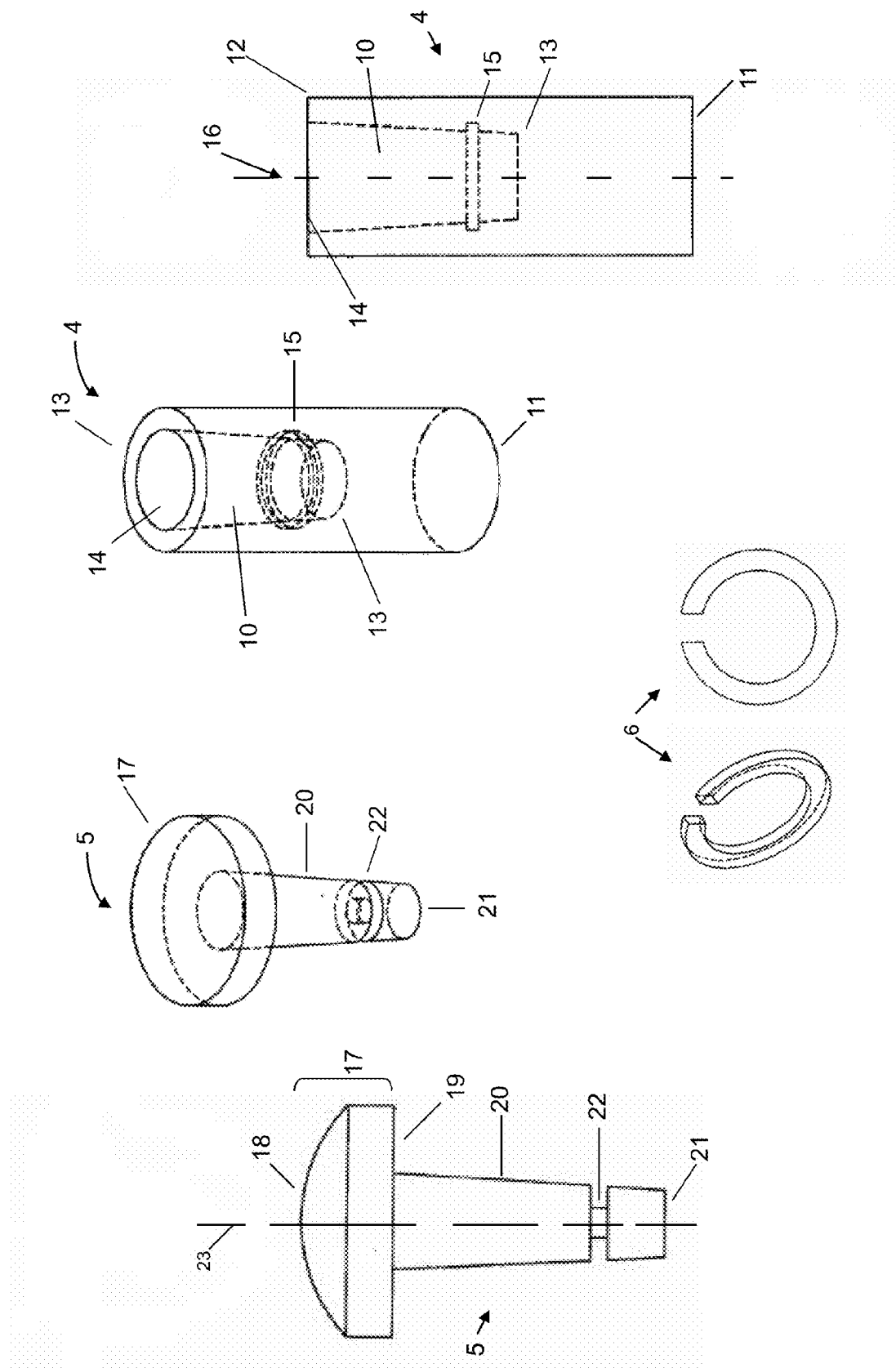

A further illustrated in FIG. 3, the base member 4 of the metatarsal component 2 is cylindrical and has a generally circular cross-section. However, it is also contemplated that a base member 4 may alternatively be non-cylindrical, have another suitable cross-section, or combinations thereof, provided that other elements of the metatarsal component 2 are also adapted to fit such alternatives. For example, a base member 4 may have a cross-section selected from generally elliptical, square, triangular, or other suitable shape. The base member 4 comprises a continuous first end 11, a non-continuous second end 12, and a cavity 10 for receiving a portion of the metatarsal articulation member 5. The cavity 10 comprises a first end 13 recessed within the base member 4, a second end 14 that is partially shared with the second end 12 of the base member 4, and a peripheral slot 15 for receiving a portion of the locking member 6. As shown, the cavity 10 is generally conical or tapered and has a generally circular cross-section. However, it is also contemplated that the cavity 10 may alternatively be non-conical or non-tapered, have another suitable cross-section, or combinations thereof, provided that other elements of the metatarsal component 2 are also adapted to fit such alternatives. For example, a cavity 10 may have a cross-section selected from generally elliptical, square, triangular, or other suitable shape. The slot 15 is integrated with and formed around all or a portion of the cavity 10 in a direction away from a longitudinal axis 16 of the base member 4. As shown, the slot 15 may be positioned at or proximate to the first end 13 of the cavity 10, but it is also contemplated that it may alternatively be positioned elsewhere along the cavity 10, provided that the metatarsal articulation member 5 is correspondingly adapted. Moreover, it is also contemplated that the first end 11 of the base member 4 may alternatively be non-continuous and partially shared with the first end 13 of the cavity 10.

The articulation member 5 of the metatarsal component 2 comprises a head portion 17, a stem 20, and an integral slot 22. The head portion 17 comprises a substantially convex bearing surface 18 and a proximal surface 19 opposite thereto. As shown, the proximal surface 19 is generally planar, but it is also contemplated that it could be non-planar. The bearing surface 18 is adapted to emulate the general shape and function of the head portion of the metatarsal bone within a metatarsophalangeal joint. The stem 20 protrudes from the center (not labeled) of the proximal surface 19, terminates at a proximal end 21, and is adapted to be received within the cavity 10 of the base member 4. When so received, the proximal surface 19 abuts the second end 12 of the base member 4. It is also contemplated that the proximal surface 19 could be spaced from the second end 12 when so received. As shown, the stem 20 is generally conical or tapered and has a generally circular cross-section. However, it is also contemplated that the stem 20 may alternatively be non-conical or non-tapered, have another suitable cross-section, or combinations thereof, provided that other elements of the metatarsal component 2 are also adapted to fit such alternatives. For example, a stem 20 may have a cross-section selected from generally elliptical, square, triangular, or other suitable shape. The slot 22 is integrated with and formed in a direction towards a longitudinal axis 23 of the metatarsal articulation member 5 around all or a portion of the stem 20, and it is adapted to receive a portion of the locking member 6. As shown, the slot 22 may be positioned at or proximate to the proximal end 21, but it is also contemplated that it may alternatively be positioned elsewhere along the stem 20, provided that the base member 4 is correspondingly adapted. The stem 20 and slot 22 are adapted to fit within the cavity 10 of the base member 4 such that both slots 15, 22 are aligned to each receive a portion and together receive the whole of the locking member 6.

The locking member 6 is a resilient spring member having at least a first and a second configuration (not shown) and is adapted to be received within both slots 15, 22 to mechanically join the metatarsal articulation member 5 with the base member 4. In some embodiments, the metatarsal articulation member 5 and the base member 4 are permanently joined, and as such are effectively a single component of the implantable device. As shown, the locking member 6 is non-continuous and has a generally circular cross-section. However, it is also contemplated that the locking member 6 may alternatively be continuous, have a different cross-section, or combinations thereof, provided that other elements (including, but not limited to the slots 15, 22) of the metatarsal component 2 are correspondingly adapted. For example, a locking member 6 could have a cross-section selected from generally elliptical, square, triangular, or other suitable cross-section. In some embodiments, the locking member 6 may comprise a resilient material suitable for surgical implants.

In some embodiments of assembly, the locking member 6 is flexed from a first to a second configuration upon insertion through the partially shared second ends 12, 14 of the base member 4 and cavity 10; remains in the second configuration as it is advanced along the cavity 10 towards the first end 13; and upon encountering the slot 15 flexes from the second to the first configuration as it is received within the slot 15. Alternatively, it is contemplated that the locking member 6 may flex from the second to an intermediate third configuration as it is received within the slot 15.

In some embodiments of assembly, a portion of the locking member 6 is received within the slot 22 of the metatarsal articulating member 5; the stem 20 of said articulating member 5 is inserted through the shared ends 12, 14 of the base member 4 and cavity 10 as the locking member 6 flexes from a first to a second configuration; the locking member 6 remains in the second configuration as it and the stem 20 are advanced along the cavity 10 towards the first end 13; and upon encountering the slot 15 of the base member 4, the locking member 6 flexes from the second to the first configuration as it is received within the slot 15. Alternatively, it is contemplated that the locking member 6 may flex from the second to an intermediate third configuration as it is received within the slot 15.

Figure 4:
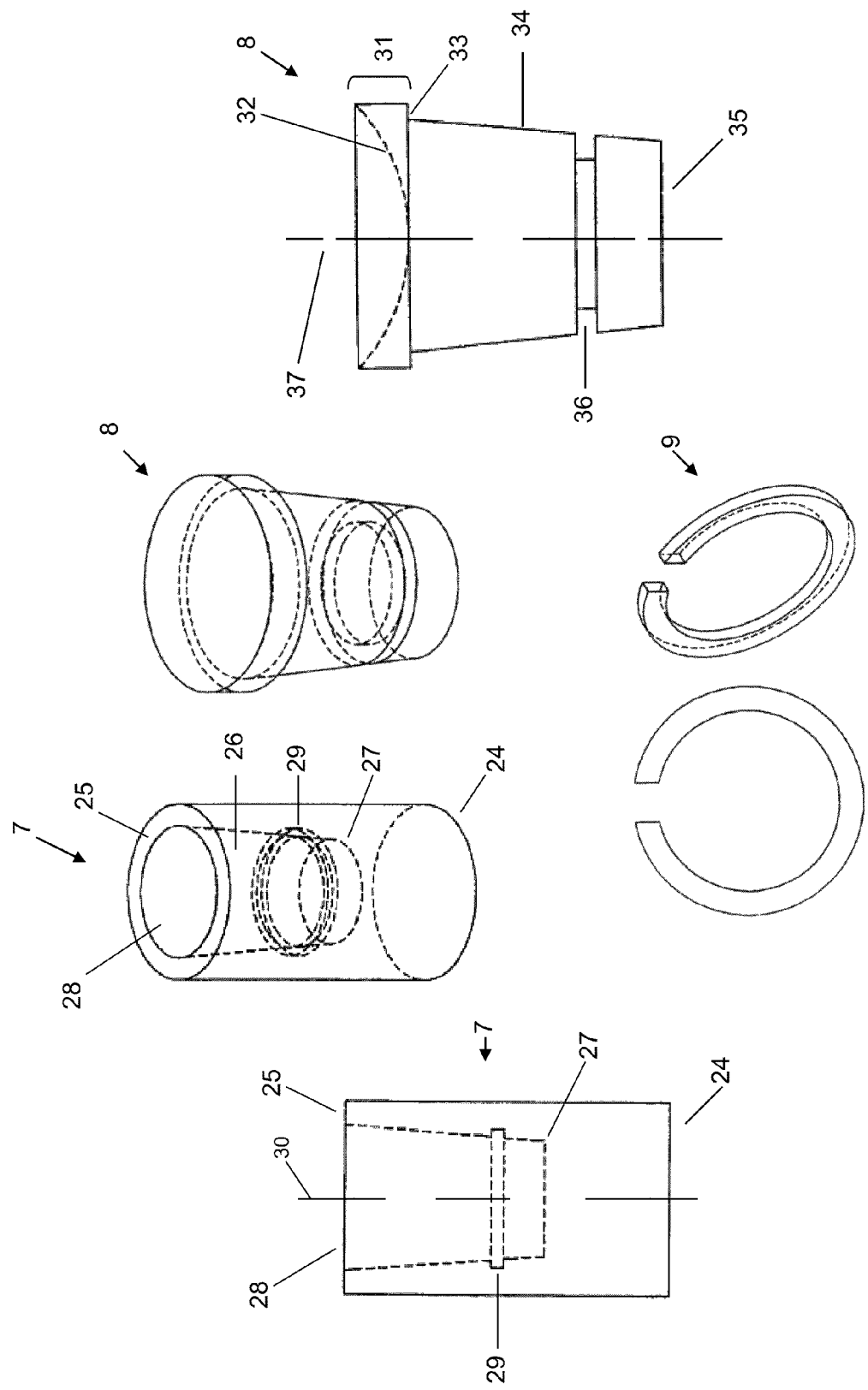

As further illustrated in FIG. 4, the base member 7 of the phalanx component 3 is cylindrical and has a generally circular cross-section. However, it is also contemplated that a base member 7 may alternatively be non-cylindrical, have another suitable cross-section, or combinations thereof, provided that other elements of the phalanx component 3 are also adapted to fit such alternatives. For example, a base member 7 may have a cross-section selected from generally elliptical, square, triangular, or other suitable shape. The base member 7 comprises a continuous first end 24, a non-continuous second end 25, and a cavity 26 for receiving a portion of the phalanx articulation member 8. The cavity 26 comprises a first end 27 recessed within the base member 7, a second end 28 that is partially shared with the second end 25 of the base member 7, and a peripheral slot 29 for receiving a portion of the locking member 9. As shown, the cavity 26 is generally conical or tapered and has a generally circular cross-section. However, it is also contemplated that the cavity 26 may alternatively be non-conical or non-tapered, have another suitable cross-section, or combinations thereof, provided that other elements of the phalanx component 3 are also adapted to fit such alternatives. For example, a cavity 26 may have a cross-section selected from generally elliptical, square, triangular, or other suitable shape. The slot 29 is integrated with and formed around all or a portion of the cavity 26 in a direction away from a longitudinal axis 30 of the base member 7. As shown, the slot 29 may be positioned at or proximate to the first end 27, but it is also contemplated that it may alternatively be positioned elsewhere along the cavity 26, provided that the phalanx articulation member 8 is correspondingly adapted. Moreover, it is also contemplated that the first end 24 of the base member 7 may alternatively be non-continuous and partially shared with the first end 27 of the cavity 26.

The articulation member 8 of the phalanx component 3 comprises a head portion 31, a stem 34, and an integral slot 36. The head portion 31 comprises a substantially concave bearing surface 32 and a distal surface 33 opposite thereto. As shown, the distal surface 33 is generally planar, but it is also contemplated that it could be non-planar. The bearing surface 32 is adapted to emulate the general shape and function of the proximal portion of the proximal phalanx bone within a meta-tarsophalangeal joint. The stem 34 protrudes from the center (not labeled) of the distal surface 33, terminates at a distal end 35, and is adapted to be received within the cavity 26 of the base member 7. When so received, the distal surface 33 abuts the second end 25 of the base member 7. It is also contemplated that the distal surface 33 could be spaced from the second end 25 when so received. As shown, the stem 34 is generally conical or tapered and has a generally circular cross-section. However, it is also contemplated that the stem 34 may alternatively be non-conical or non-tapered, have another suitable cross-section, or combinations thereof, provided that other elements of the phalanx component 3 are also adapted to fit such alternatives. For example, a stem 34 may have a cross-section selected from generally elliptical, square, triangular, or other suitable shape. The slot 36 is integrated with and formed around all or a portion of the stem 34 in a direction towards a longitudinal axis 37 of the phalanx articulation member 8, and it is adapted to receive a portion of the locking member 9. As shown, the slot 36 may be positioned at or proximate to the distal end 35, but it is also contemplated that it may alternatively be positioned elsewhere along the stem 34, provided that the base member 7 is correspondingly adapted. The stem 34 and slot 36 are adapted to fit within the cavity 26 of the base member 7 such that both slots 29, 36 are aligned to each receive a portion and together receive the whole of the locking member 9.

The locking member 9 is a resilient spring member having at least a first and a second configuration (not shown) and is adapted to be received within both slots 29, 36 to mechanically join the phalanx articulation member 8 with the base member 7. In some embodiments, the phalanx articulation member 8 and the base member 7 are permanently joined, and as such are effectively a single component of the implantable device. As shown, the locking member 9 is non-continuous and has a generally circular cross-section. However, it is also contemplated that the locking member 9 may alternatively be continuous, have a different cross-section, or combinations thereof, provided that other elements (including, but not limited to the slots 29, 36) of the phalanx component 3 are correspondingly adapted. For example, a locking member 9 could have a cross-section selected from generally elliptical, square, triangular, or other suitable cross-section. In some embodiments, the locking member 9 may comprise a resilient material suitable for surgical implants.

In some embodiments of assembly, the locking member 9 is flexed from a first to a second configuration upon insertion through the partially shared second ends 25, 28 of the base member 7 and cavity 26; remains in the second configuration as it is advanced along the cavity 26 towards the first end 27; and upon encountering the slot 29 flexes from the second to the first configuration as it is received within the slot 29. Alternatively, it is contemplated that the locking member 9 may flex from the second to an intermediate third configuration as it is received within the slot 29.

In some embodiments of assembly, a portion of the locking member 9 is received within the slot 36 of the phalanx articulating member 8, the stem 34 of said articulating member 8 is inserted through the shared ends 25, 28 of the base member 7 and cavity 26 as the locking member 9 flexes from a first to a second configuration; the locking member 9 remains in the second configuration as it and the stem 34 are advanced along the cavity 26 towards the first end 27; and upon encountering the slot 29 of the base member 7, the locking member 9 flexes from the second to the first configuration as it is received within the slot 29. Alternatively, it is contemplated that the locking member 9 may flex from the second to an intermediate third configuration as it is received within the slot 29.

Figure 5:
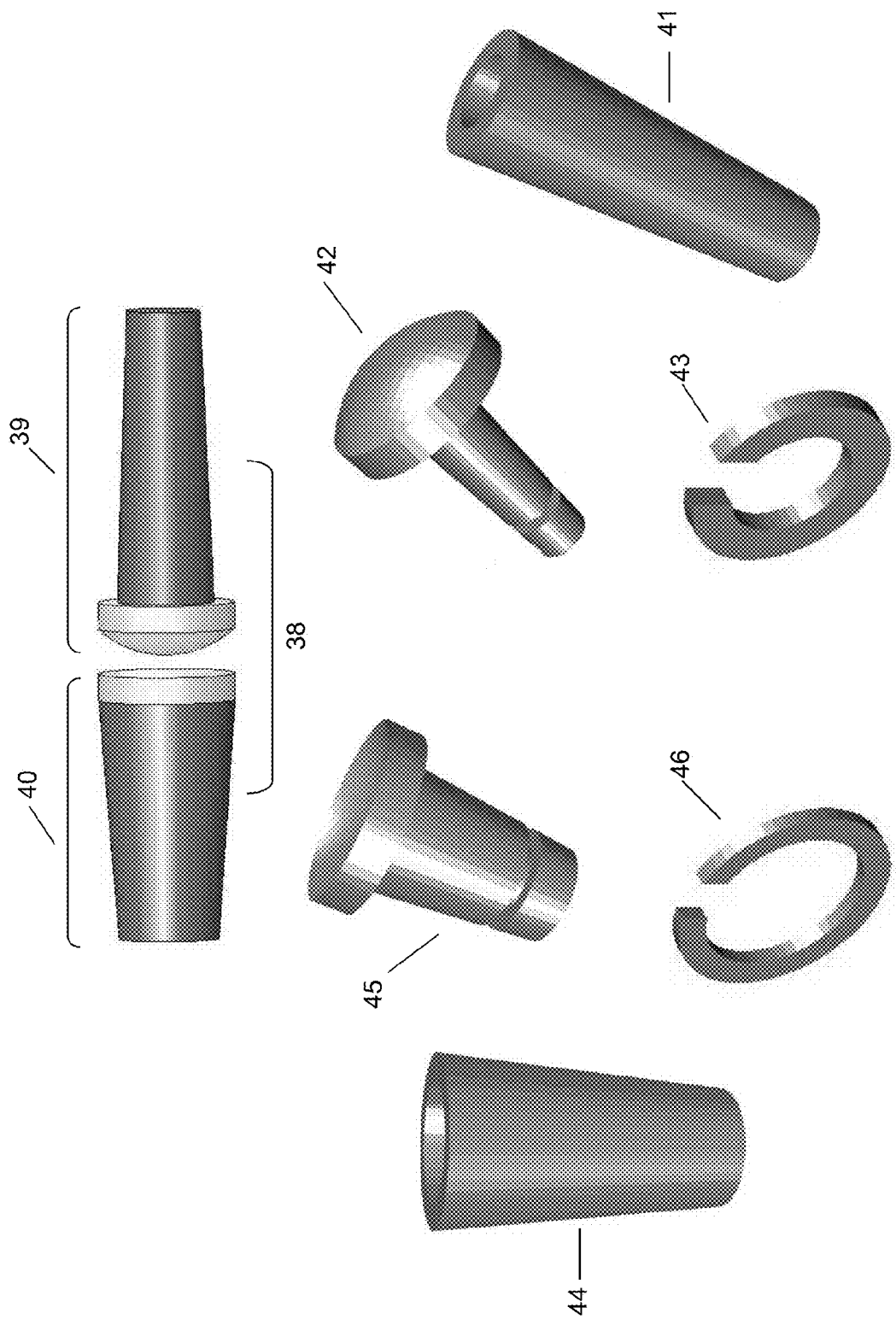
FIGS. 5-7 illustrate an additional example of an implantable two-component device and elements thereof.
Figure 6:
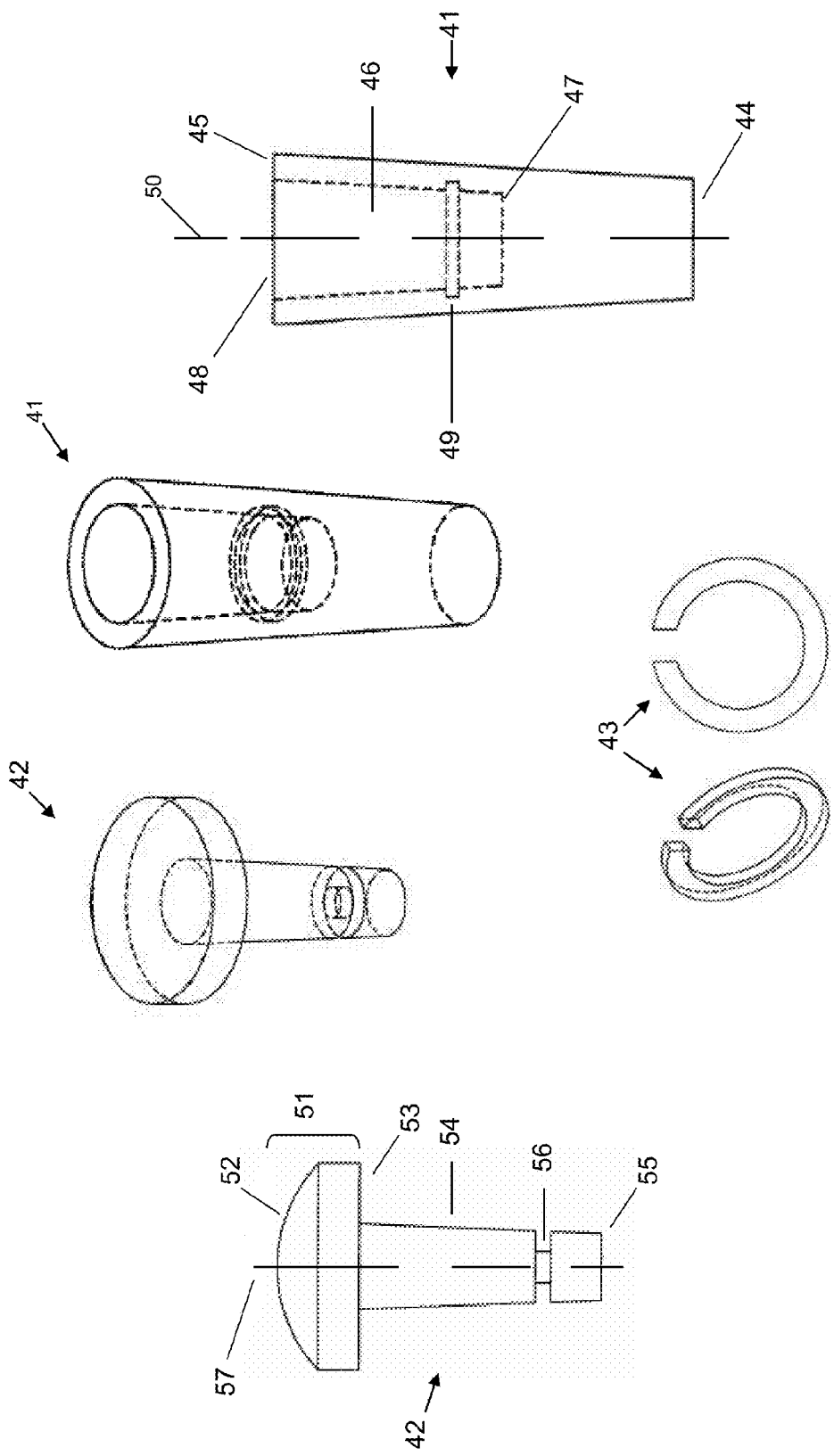
Figure 7:
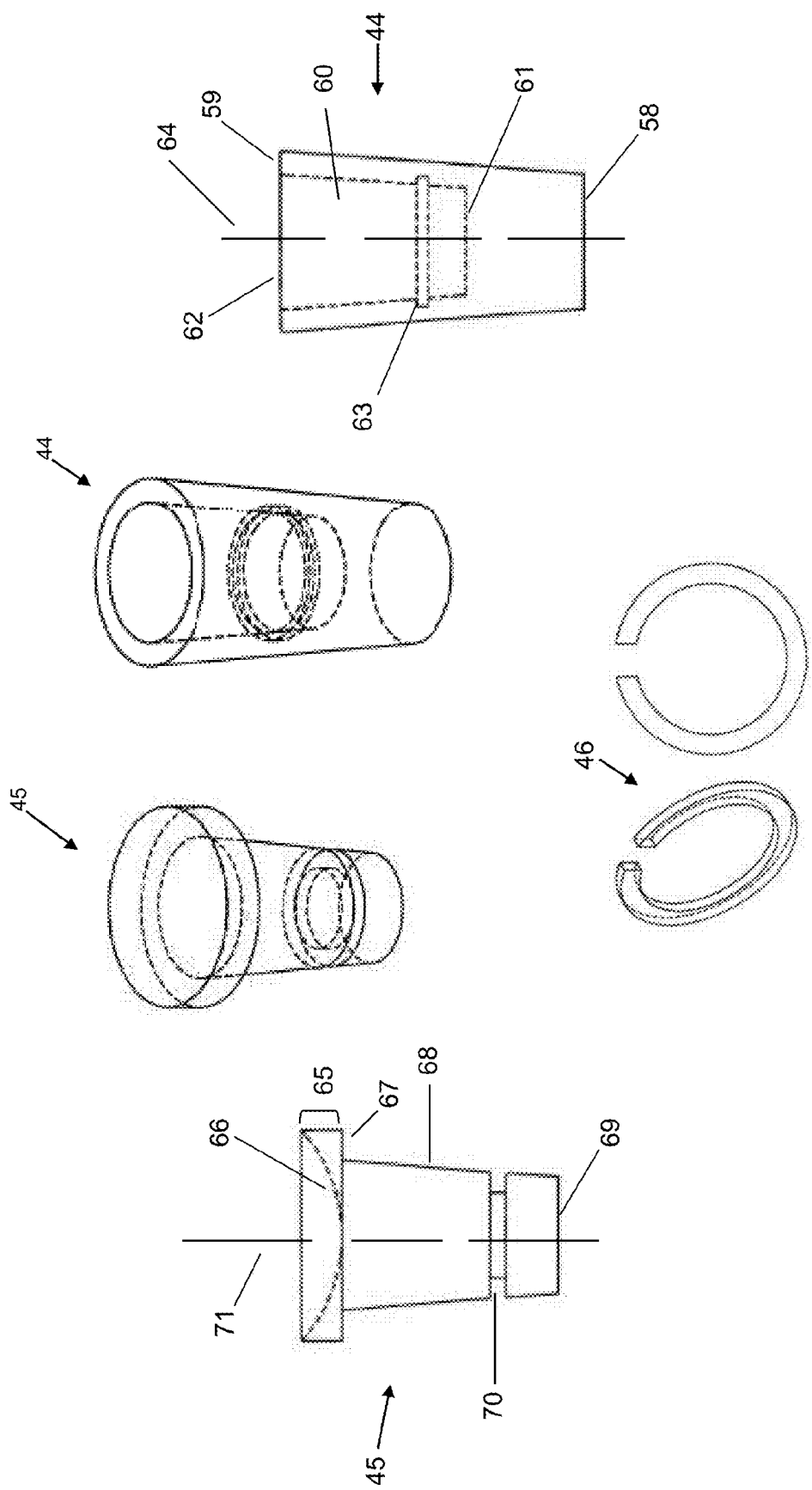

Referring to FIGS. 5-7, illustrated is another example of a two-component implant 38 that comprises a metatarsal component 39 and a phalanx component 40. The metatarsal component 39 is designed to be implanted into the distal end of a resected metatarsal bone to replace all or a portion of the metatarsal head and function as the metatarsal component of the metatarsophalangeal joint. The metatarsal component 39 comprises a base member 41, a metatarsal articulation member 42, and a locking member 43. The base member 41 may be of any suitable length and dimension to allow for fixation within the metatarsal bone, and may be fixed by any medically suitable means. In some embodiments, the base member 41 is designed to be implanted in approximately one third of the length of the metatarsal bone. In some embodiments, it may be fixed with bone cement.

The phalanx component 40 is designed to be implanted into the proximal end of a resected proximal phalanx bone to replace all or a portion of the proximal end of the proximal phalanx and function as the phalanx component of the metatarsophalangeal joint. The phalanx component 40 comprises a base member 44, a phalanx articulation member 45, and a locking member 46. The base member 44 may be of any suitable length and dimension to allow for fixation within the phalanx bone, and may be fixed by any medically suitable means. In some embodiments, the base member 44 is designed to be implanted in approximately half of the length of the phalanx bone. In some embodiments, it may be fixed with bone cement.

In some embodiments, one or both of the metatarsal component 39 and the phalanx component 40 are implanted into the human foot to replace all or a portion of the metatarsophalangeal joint. In some embodiments, one or both components 39, 40 may be implanted in a primary resectional arthroplasty procedure, in a revision arthroplasty procedure performed to replace or compensate for a failed implant, or combinations thereof. In some embodiments, one or both components 39, 40 are implanted in a revision arthroplasty procedure. In some embodiments, each component 39, 40 implanted may be selected from small, medium, or large sizes as necessary to approximate the anatomy of the subject. In some embodiments, the components 39, 40 may comprise one or more dimensions set forth in Table 3. In some embodiments, each component 39, 40 and elements thereof may be customized to the anatomy of the subject.

TABLE 3

| | Dimension (mm) |
|---|---|
| Metatarsal | |
| Base Member Length | 22-26 |
| Base Member Outer Diameter Top | 7-10 |
| Base Member Outer Diameter Bottom | 5-7 |
| Articulation Member Length (Excluding Head Portion) | 12-16 |
| Articulation Member Outer Diameter Top | 4-7 |
| Articulation Member Outer Diameter Bottom | 3-5 |
| Head Portion Diameter | 10-13 |
| Locking Member Outer Diameter | 4-7 |
| Locking Member Inner Diameter | 2-5 |
| Locking Member Thickness | 0.5 |
| Head Portion Height | 2 |
| Phalanx | |
| Base Member Length | 18-22 |
| Base Member Outer Diameter Top | 10-13 |
| Base Member Outer Diameter Bottom | 7-10 |
| Articulation Member Length (Excluding Head Portion) | 10-15 |
| Articulation Member Outer Diameter Top | 7-10 |
| Articulation Member Outer Diameter Bottom | 5-8 |
| Head Portion Diameter | 10-13 |
| Locking Member Outer Diameter | 7-10 |
| Locking Member Inner Diameter | 5-8 |
| Locking Member Thickness | 0.5 |
| Head Portion Depth | 2 |

As further illustrated in FIG. 6, the base member 41 of the metatarsal component 39 is conical or tapered and has a generally circular cross-section. However, it is also contemplated that a base member 41 may alternatively be non-conical or non-tapered, have another suitable cross-section, or combinations thereof, provided that other elements of the metatarsal component 39 are also adapted to fit such alternatives. For example, a base member 41 may have a cross-section selected from generally elliptical, square, triangular, or other suitable shape. The base member 41 comprises a continuous first end 44, a non-continuous second end 45, and a cavity 46 for receiving a portion of the metatarsal articulation member 42. The cavity 46 comprises a first end 47 recessed within the base member 41, a second end 48 that is partially shared with the second end 45 of the base member 41, and a peripheral slot 49 for receiving a portion of the locking member 43. As shown, the cavity 46 is generally conical or tapered and has a generally circular cross-section. However, it is also contemplated that the cavity 46 may alternatively be non-conical or non-tapered, have another suitable cross-section, or combinations thereof, provided that other elements of the metatarsal component 39 are also adapted to fit such alternatives. For example, a cavity 46 may have a cross-section selected from generally elliptical, square, triangular, or other suitable shape. The slot 49 is integrated with and formed around all or a portion of the cavity 46 in a direction away from a longitudinal axis 50 of the base member 41. As shown, the slot 49 may be positioned at or proximate to the first end 47, but it is also contemplated that it may alternatively be positioned elsewhere along the cavity 46, provided that the metatarsal articulation member 42 is correspondingly adapted. Moreover, it is also contemplated that the first end 44 of the base member 41 may alternatively be non-continuous and partially shared with the first end 47 of the cavity 46.

The articulation member 42 of the metatarsal component 39 comprises a head portion 51, a stem 54, and an integral slot 56. The head portion 51 comprises a substantially convex bearing surface 52 and a proximal surface 53 opposite thereto. As shown, the proximal surface 53 is generally planar, but it is also contemplated that it could be non-planar. The bearing surface 52 is adapted to emulate the general shape and function of the head portion of the metatarsal bone within a metatarsophalangeal joint. The stem 54 protrudes from the center (not labeled) of the proximal surface 53, terminates at a proximal end 55, and is adapted to be received within the cavity 46 of the base member 41. When so received, the proximal surface 53 abuts the second end 45 of the base member 41. It is also contemplated that the proximal surface 53 could be spaced from the second end 45 when so received. As shown, the stem 54 is generally conical or tapered and has a generally circular cross-section. However, it is also contemplated that the stem 54 may alternatively be non-conical or non-tapered, have another suitable cross-section, or combinations thereof, provided that other elements of the metatarsal component 39 are also adapted to fit such alternatives. For example, a stem 54 may have a cross-section selected from generally elliptical, square, triangular, or other suitable shape. The slot 56 is integrated with and formed around all or a portion of the stem 54 in a direction towards a longitudinal axis 57 of the metatarsal articulation member 42, and it is adapted to receive a portion of the locking member 43. As shown, the slot 56 may be positioned at or proximate to the proximal end 55, but it is also contemplated that it may alternatively be positioned elsewhere along the stem 54, provided that the base member 41 is correspondingly adapted. The stem 54 and slot 56 are adapted to fit within the cavity 46 of the base member 41 such that both slots 49, 56 are aligned to each receive a portion and together receive the whole of the locking member 43.

The locking member 43 is a resilient spring member having at least a first and a second configuration (not shown) and is adapted to be received within both slots 49, 56 to mechanically join the metatarsal articulation member 42 with the base member 41. In some embodiments, the metatarsal articulation member 42 and the base member 41 are permanently joined, and as such are effectively a single component of the implantable device. As shown, the locking member 43 is non-continuous and has a generally circular cross-section. However, it is also contemplated that the locking member 43 may alternatively be continuous, have an different cross-section, or combinations thereof, provided that other elements (including, but not limited to the slots 49, 56) of the metatarsal component 39 are correspondingly adapted. For example, a locking member 43 could have a cross-section selected from generally elliptical, square, triangular, or other suitable cross-section. In some embodiments, the locking member 43 may comprise a resilient material suitable for surgical implants.

In some embodiments of assembly, the locking member 43 is flexed from a first to a second configuration upon insertion through the partially shared second ends 45, 48 of the base member 41 and cavity 46; remains in the second configuration as it is advanced along the cavity 46 towards the first end 47; and upon encountering the slot 49 flexes from the second to the first configuration as it is received within the slot 49. Alternatively, it is contemplated that the locking member 43 may flex from the second to an intermediate third configuration as it is received within the slot 49.

In some embodiments of assembly, a portion of the locking member 43 is received within the slot 56 of the metatarsal articulating member 42; the stem 54 of said articulating member 42 is inserted through the shared ends 45, 48 of the base member 41 and cavity 46 as the locking member 43 flexes from a first to a second configuration; the locking member 43 remains in the second configuration as it and the stem 54 are advanced along the cavity 46 towards the first end 47; and upon encountering the slot 49 of the base member 41, the locking member 43 flexes from the second to the first configuration as it is received within the slot 49. Alternatively, it is contemplated that the locking member 43 may flex from the second to an intermediate third configuration as it is received within the slot 49.

A further illustrated in FIG. 7, the base member 44 of the phalanx component 40 is conical or tapered and has a generally circular cross-section. However, it is also contemplated that a base member 44 may alternatively be non-conical or non-tapered, have another suitable cross-section, or combinations thereof, provided that other elements of the phalanx component 40 are also adapted to fit such alternatives. For example, a base member 44 may have a cross-section selected from generally elliptical, square, triangular, or other suitable shape. The base member 44 comprises a continuous first end 58, a non-continuous second end 59, and a cavity 60 for receiving a portion of the phalanx articulation member 45. The cavity 60 comprises a first end 61 recessed within the base member 44, a second end 62 that is partially shared with the second end 59 of the base member 44, and a peripheral slot 63 for receiving a portion of the locking member 46. As shown, the cavity 60 is generally conical or tapered and has a generally circular cross-section. However, it is also contemplated that the cavity 60 may alternatively be non-conical or non-tapered, have another suitable cross-section, or combinations thereof, provided that other elements of the phalanx component 40 are also adapted to fit such alternatives. For example, a cavity 60 may have a cross-section selected from generally elliptical, square, triangular, or other suitable shape. The slot 63 is integrated with and formed around all or a portion of the cavity 60 in a direction away from a longitudinal axis 64 of the base member 44. As shown, the slot 63 may be positioned at or proximate to the first end 61, but it is also contemplated that it may alternatively be positioned elsewhere along the cavity 60, provided that the phalanx articulation member 45 is correspondingly adapted. Moreover, it is also contemplated that the first end 58 of the base member 44 may alternatively be non-continuous and partially shared with the first end 61 of the cavity 60.

The articulation member 45 of the phalanx component 40 comprises a head portion 65, a stem 68, and an integral slot

70. The head portion 65 comprises a substantially concave bearing surface 66 and a distal surface 67 opposite thereto. As shown, the distal surface 67 is generally planar, but it is also contemplated that it could be non-planar. The bearing surface 66 is adapted to emulate the general shape and function of the proximal portion of the proximal phalanx bone within a metatarsophalangeal joint. The stem 68 protrudes from the center (not labeled) of the distal surface 67, terminates at a distal end 69, and is adapted to be received within the cavity 60 of the base member 44. When so received, the distal surface 67 abuts the second end 59 of the base member 44. It is also contemplated that the distal surface 67 could be spaced from the second end 59 when so received. As shown, the stem 68 is generally conical or tapered and has a generally circular cross-section. However, it is also contemplated that the stem 68 may alternatively be non-conical or non-tapered, have another suitable cross-section, or combinations thereof, provided that other elements of the phalanx component 40 are also adapted to fit such alternatives. For example, a stem 68 may have a cross-section selected from generally elliptical, square, triangular, or other suitable shape. The slot 70 is integrated with and formed around all or a portion of the stem 68 in a direction towards a longitudinal axis 71 of the phalanx articulation member 45, and it is adapted to receive a portion of the locking member 46. As shown, the slot 70 may be positioned at or proximate to the distal end 69, but it is also contemplated that it may alternatively be positioned elsewhere along the stem 68, provided that the base member 44 is correspondingly adapted. The stem 68 and slot 70 are adapted to fit within the cavity 60 of the base member 44 such that both slots 63, 70 are aligned to each receive a portion and together receive the whole of the locking member 46.

The locking member 46 is a resilient spring member having at least a first and a second configuration (not shown) and is adapted to be received within both slots 63, 70 to mechanically join the phalanx articulation member 45 with the base member 44. In some embodiments, the phalanx articulation member 45 and the base member 44 are permanently joined, and as such are effectively a single component of the implantable device. As shown, the locking member 46 is non-continuous and has a generally circular cross-section. However, it is also contemplated that the locking member 46 may alternatively be continuous, have an different cross-section, or combinations thereof, provided that other elements (including, but not limited to the slots 63, 70) of the phalanx component 40 are correspondingly adapted. For example, a locking member 46 could have a cross-section selected from generally elliptical, square, triangular, or other suitable cross-section. In some embodiments, the locking member 46 may comprise a resilient material suitable for surgical implants.

In some embodiments of assembly, the locking member 46 is flexed from a first to a second configuration upon insertion through the partially shared second ends 59, 62 of the base member 44 and cavity 60; remains in the second configuration as it is advanced along the cavity 60 towards the first end 61; and upon encountering the slot 63 flexes from the second to the first configuration as it is received within the slot 63. Alternatively, it is contemplated that the locking member 46 may flex from the second to an intermediate third configuration as it is received within the slot 63.

In some embodiments of assembly, a portion of the locking member 46 is received within the slot 70 of the phalanx articulating member 45; the stem 68 of said articulating member 45 is inserted through the shared ends 59, 62 of the base member 44 and cavity 60 as the locking member 46 flexes from a first to a second configuration; the locking member 46 remains in the second configuration as it and the stem 68 are advanced along the cavity 60 towards the first end 61; and upon encountering the slot 63 of the base member 44, the locking member 46 flexes from the second to the first configuration as it is received within the slot 63. Alternatively, it is contemplated that the locking member 46 may flex from the second to an intermediate third configuration as it is received within the slot 63.

Figure 8:
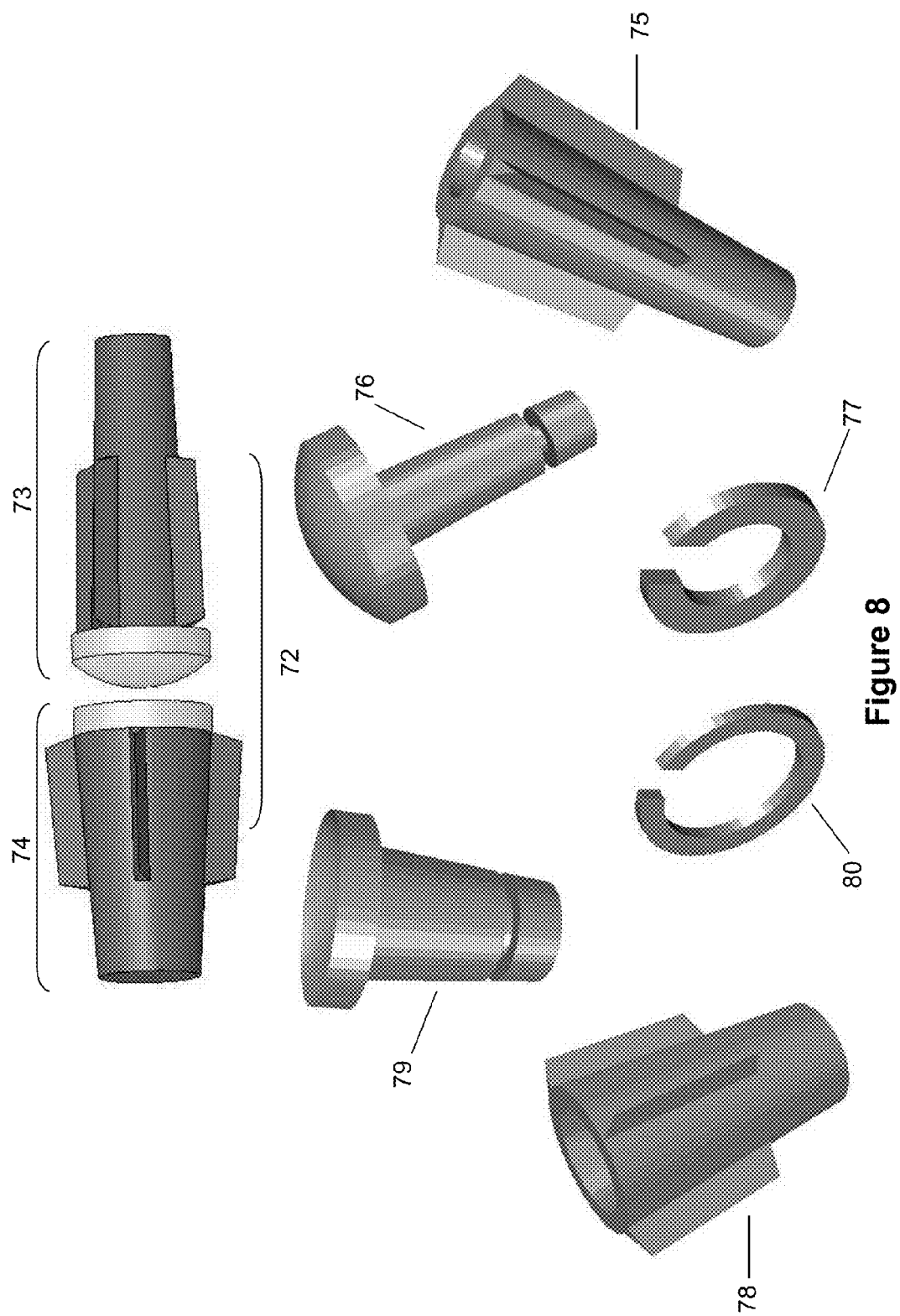
FIGS. 8-10 illustrate a further example of an implantable two-component device and elements thereof.
Figure 9:
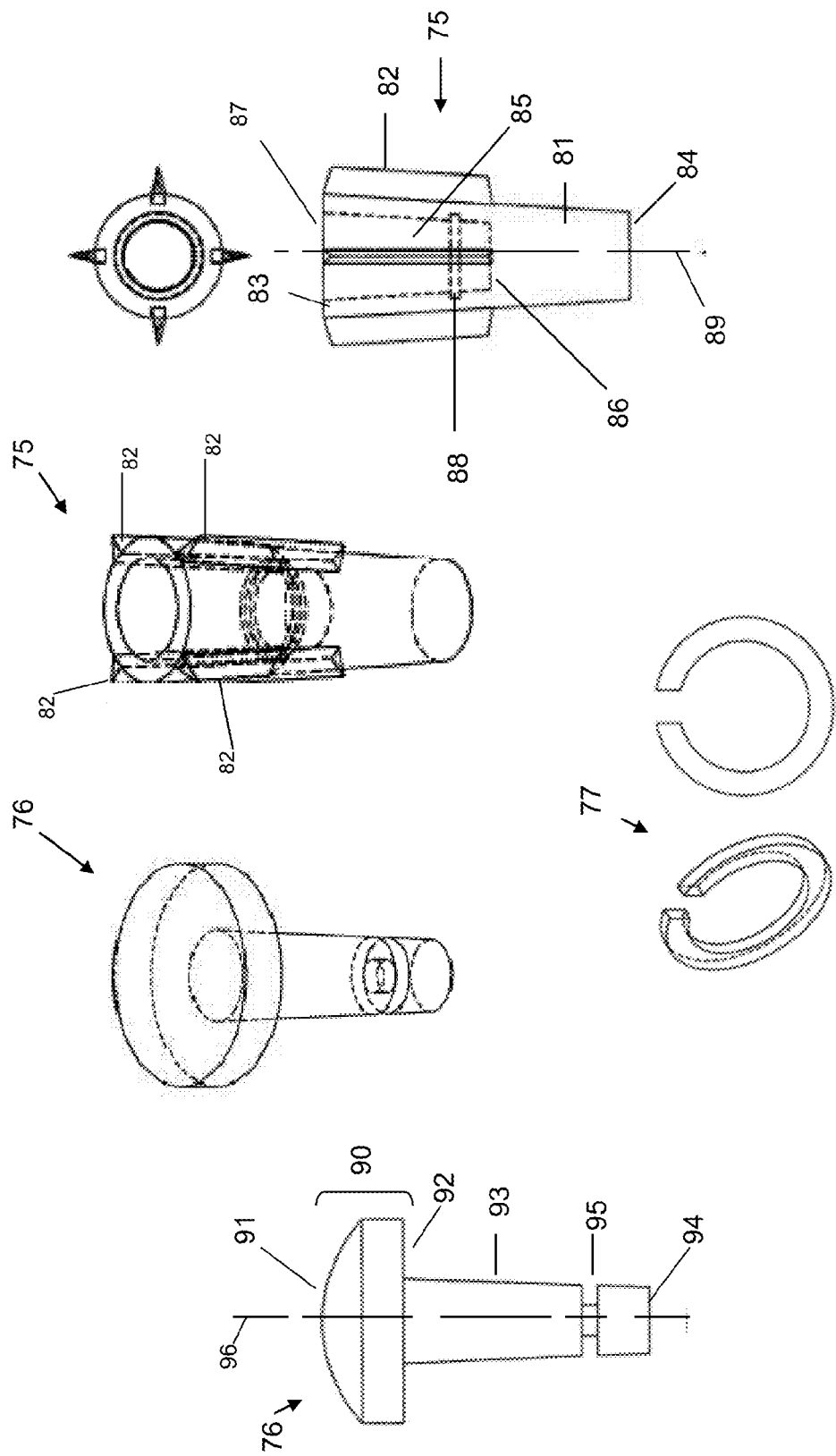
Figure 10:
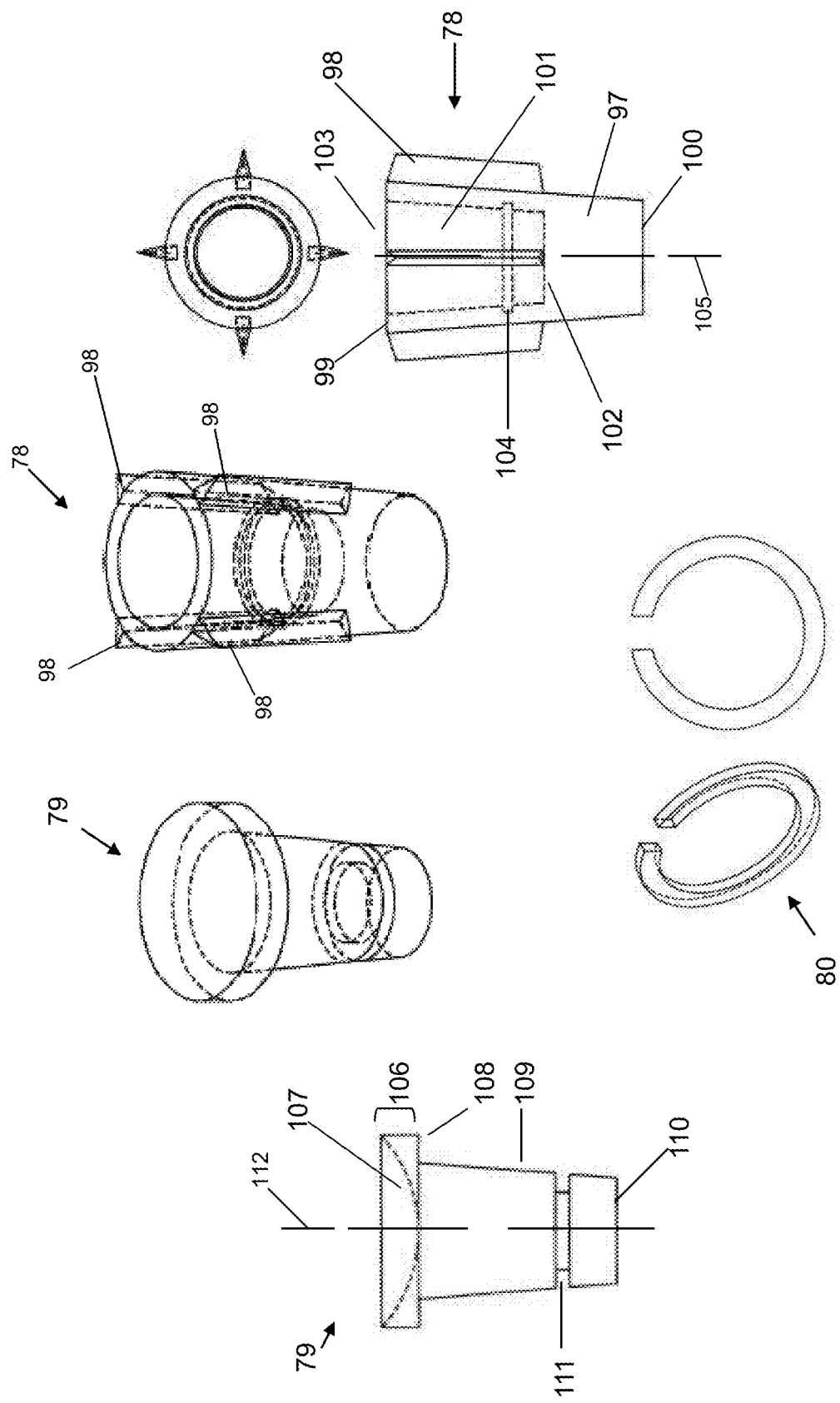

Referring to FIGS. 8-10, illustrated is another example of a two-component implant 72 that comprises a metatarsal component 73 and a phalanx component 74. The metatarsal component 73 is designed to be implanted into the distal end of a resected metatarsal bone to replace all or a portion of the metatarsal head and function as the metatarsal component of the metatarsophalangeal joint. The metatarsal component 73 comprises a base member 75, a metatarsal articulation member 76, and a locking member 77. The base member 75 may be of any suitable length and dimension to allow for fixation within the metatarsal bone, and may be fixed by any medically suitable means. In some embodiments, it is designed to be implanted in approximately one third of the length of the metatarsal bone. In some embodiments, the base member 75 is designed to be fixed by tension on the interior cavity of the resected bone.

The phalanx component 74 is designed to be implanted into the proximal end of a resected proximal phalanx bone to replace all or a portion of the proximal end of the proximal phalanx and function as the phalanx component of the metatarsophalangeal joint. The phalanx component 74 comprises a base member 78, a phalanx articulation member 79, and a locking member 80. The base member 78 may be of any suitable length and dimension to allow for fixation within the phalanx bone, and may be fixed by any medically suitable means. In some embodiments, it is designed to be implanted in approximately half of the length of the phalanx bone. In some embodiments, the base member 78 is designed to be fixed by tension on the interior cavity of the resected bone.

In some embodiments, one or both of the metatarsal component 73 and the phalanx component 74 are implanted into the human foot to replace all or a portion of the metatarsophalangeal joint. In some embodiments, one or both components 73, 74 may be implanted in a primary resectional arthroplasty procedure, in a revision arthroplasty procedure performed to replace or compensate for a failed implant, or combinations thereof. In some embodiments, one or both components 73, 74 are implanted in a revision arthroplasty procedure. In some embodiments, each component 73, 74 implanted may be selected from small, medium, or large sizes as necessary to approximate the anatomy of the subject. In some embodiments, the components 73, 74 may comprise one or more dimensions set forth in Table 3. In some embodiments, each component 73, 74 and elements thereof may be customized to the anatomy of the subject.

As further illustrated in FIG. 9, the base member 75 of the metatarsal component 73 comprises primary 81 and secondary 82 body portions. The primary body portion 81 is conical or tapered and has a generally circular cross-section. However, it is also contemplated that the primary body portion 81 may alternatively be non-conical or non-tapered, have another suitable cross-section, or combinations thereof, provided that other elements of the metatarsal component 73 are also adapted to fit such alternatives. For example, a primary body portion 81 may have a cross-section selected from generally elliptical, square, triangular, or other suitable shape. The secondary body portion 82 comprises one or more flanges peripherally positioned around the primary body portion 81. As shown, the secondary body portion 82 comprises four flanges equidistantly positioned around the periphery of the primary body portion 81. Each of said flanges has a generally triangular cross-section, a length approximately two-thirds that of the primary body portion 81, one end (not labeled) positioned at the second end 83 of the base member 75, and runs longitudinally along the primary body portion 81. However, it is contemplated that the secondary body portion 82 may have fewer or more flanges, that the flanges may have another suitable cross-section (for example, generally elliptical, square, or other suitable shape), that the flanges may have another suitable length, that the flanges may be suitably spaced or positioned in a different manner, and combinations thereof. In some embodiments, the secondary body portion 82 may be a resilient spring member adapted to be received within the interior cavity of a resected bone, wherein upon insertion into the cavity, the secondary body portion 82 flexes from a first to a second configuration (not shown) that exerts sufficient tension on the bone cavity to fix the base member 75. In some embodiments, the secondary body portion 82 may comprise a resilient material suitable for surgical implants.

The base member 75 comprises a continuous first end 84, a non-continuous second end 83, and a cavity 85 for receiving a portion of the metatarsal articulation member 76. The cavity 85 comprises a first end 86 recessed within the base member 75, a second end 87 that is partially shared with the second end 83 of the base member 75, and a peripheral slot 88 for receiving a portion of the locking member 77. As shown, the cavity 85 is generally conical or tapered and has a generally circular cross-section. However, it is also contemplated that the cavity 85 may alternatively be non-conical or non-tapered, have another suitable cross-section, or combinations thereof, provided that other elements of the metatarsal component 73 are also adapted to fit such alternatives. For example, a cavity 85 may have a cross-section selected from generally elliptical, square, triangular, or other suitable shape. The slot 88 is integrated with and formed around all or a portion of the cavity 85 in a direction away from a longitudinal axis 89 of the base member 75. As shown, the slot 88 may be positioned at or proximate to the first end 86, but it is also contemplated that it may alternatively be positioned elsewhere along the cavity 85, provided that the metatarsal articulation member 76 is correspondingly adapted. Moreover, it is also contemplated that the first end 84 of the base member 75 may alternatively be non-continuous and partially shared with the first end 86 of the cavity 85.

The articulation member 76 of the metatarsal component 73 comprises a head portion 90, a stem 93, and an integral slot 95. The head portion 90 comprises a substantially convex bearing surface 91 and a proximal surface 92 opposite thereto. As shown, the proximal surface 92 is generally planar, but it is also contemplated that it could be non-planar. The bearing surface 91 is adapted to emulate the general shape and function of the head portion of the metatarsal bone within a metatarsophalangeal joint. The stem 93 protrudes from the center (not labeled) of the proximal surface 92, terminates at a proximal end 94, and is adapted to be received within the cavity 85 of the base member 75. When so received, the proximal surface 92 abuts the second end 83 of the base member 75. It is also contemplated that the proximal surface 92 could be spaced from the second end 83 when so received. As shown, the stem 93 is generally conical or tapered and has a generally circular cross-section. However, it is also contemplated that the stem 93 may alternatively be non-conical or non-tapered, have another suitable cross-section, or combinations thereof, provided that other elements of the metatarsal component 73 are also adapted to fit such alternatives. For example, a stem 93 may have a cross-section selected from generally elliptical, square, triangular, or other suitable shape. The slot 95 is integrated with and formed in a direction towards a longitudinal axis 96 of the metatarsal articulation member 76 around all or a portion of the stem 93, and it is adapted to receive a portion of the locking member 77. As shown, the slot 95 may be positioned at or proximate to the proximal end 94, but it is also contemplated that it may alternatively be positioned elsewhere along the stem 93, provided that the base member 75 is correspondingly adapted. The stem 93 and slot 95 are adapted to fit within the cavity 85 of the base member 75 such that both slots 88, 95 are aligned to each receive a portion and together receive the whole of the locking member 77.

The locking member 77 is a resilient spring member having at least a first and a second configuration (not shown) and is adapted to be received within both slots 88, 95 to mechanically join the metatarsal articulation member 76 with the base member 75. In some embodiments, the metatarsal articulation member 76 and the base member 75 are permanently joined, and as such are effectively a single component of the implantable device. As shown, the locking member 77 is non-continuous and has a generally circular cross-section. However, it is also contemplated that the locking member 77 may alternatively be continuous, have a different cross-section, or combinations thereof, provided that other elements (including, but not limited to the slots 88, 95) of the metatarsal component 76 are correspondingly adapted. For example, a locking member 77 could have a cross-section selected from generally elliptical, square, triangular, or other suitable cross-section. In some embodiments, the locking member 77 may comprise a resilient material suitable for surgical implants.

In some embodiments of assembly, the locking member 77 is flexed from a first to a second configuration upon insertion through the partially shared second ends 83, 87 of the base member 75 and cavity 85; remains in the second configuration as it is advanced along the cavity 85 towards the first end 86; and upon encountering the slot 88 flexes from the second to the first configuration as it is received within the slot 88. Alternatively, it is contemplated that the locking member 77 may flex from the second to an intermediate third configuration as it is received within the slot 88.

In some embodiments of assembly, a portion of the locking member 77 is received within the slot 95 of the metatarsal articulating member 76; the stem 93 of said articulating member 76 is inserted through the shared ends 83, 87 of the base member 75 and cavity 85 as the locking member 77 flexes from a first to a second configuration; the locking member 77 remains in the second configuration as it and the stem 93 are advanced along the cavity 85 towards the first end 86; and upon encountering the slot 88 of the base member 75, the locking member 77 flexes from the second to the first configuration as it is received within the slot 88. Alternatively, it is contemplated that the locking member 77 may flex from the second to an intermediate third configuration as it is received within the slot 88.

As further illustrated in FIG. 10, the base member 78 of the phalanx component 74 comprises primary 97 and secondary body 98 portions. The primary body portion 97 is conical or tapered and has a generally circular cross-section. However, it is also contemplated that the primary body portion 97 may alternatively be non-conical or non-tapered, have another suitable cross-section, or combinations thereof, provided that other elements of the phalanx component 74 are also adapted to fit such alternatives. For example, a primary body portion 97 may have a cross-section selected from generally elliptical, square, triangular, or other suitable shape. The secondary body portion 98 comprises one or more flanges peripherally positioned around the primary body portion 97. As shown, the secondary body portion 98 comprises four flanges equidistantly positioned around the periphery of the primary body portion 97. Each of said flanges has a generally triangular cross-section, a length approximately two-thirds that of the primary body portion 97, one end (not labeled) positioned at the second end 99 of the base member 78, and runs longitudinally along the primary body portion 97. However, it is contemplated that the secondary body portion 98 may have fewer or more flanges, that the flanges may have another suitable cross-section (for example, generally elliptical, square, or other suitable shape), that the flanges may have another suitable length, that the flanges may be suitably spaced or positioned in a different manner, and combinations thereof. In some embodiments, the secondary body portion 98 may be a resilient spring member adapted to be received within the interior cavity of a resected bone, wherein upon insertion into the cavity, the secondary body portion 98 flexes from a first to a second configuration (not shown) that exerts sufficient tension on the bone cavity to fix the base member 78. In some embodiments, the secondary body portion 98 may comprise a resilient material suitable for surgical implants.

The base member 78 comprises a continuous first end 100, a non-continuous second end 99, and a cavity 101 for receiving a portion of the phalanx articulation member 79. The cavity 101 comprises a first end 102 recessed within the base member 78, a second end 103 that is partially shared with the second end 99 of the base member 78, and a peripheral slot 104 for receiving a portion of the locking member 80. As shown, the cavity 101 is generally conical or tapered and has a generally circular cross-section. However, it is also contemplated that the cavity 101 may alternatively be non-conical or non-tapered, have another suitable cross-section, or combinations thereof, provided that other elements of the phalanx component 74 are also adapted to fit such alternatives. For example, a cavity 101 may have a cross-section selected from generally elliptical, square, triangular, or other suitable shape. The slot 104 is integrated with and formed around all or a portion of the cavity 101 in a direction away from a longitudinal axis 105 of the base member 78. As shown, the slot 104 may be positioned at or proximate to the first end 102, but it is also contemplated that it may alternatively be positioned elsewhere along the cavity 101, provided that the phalanx articulation member 79 is correspondingly adapted. Moreover, it is also contemplated that the first end 100 of the base member 78 may alternatively be non-continuous and partially shared with the first end 102 of the cavity 101.

The articulation member 79 of the phalanx component 74 comprises a head portion 106, a stem 109, and an integral slot 111. The head portion 106 comprises a substantially concave bearing surface 107 and a distal surface 108 opposite thereto. As shown, the distal surface 108 is generally planar, but it is also contemplated that it could be non-planar. The bearing surface 107 is adapted to emulate the general shape and function of the proximal portion of the proximal phalanx bone within a metatarsophalangeal joint. The stem 109 protrudes from the center (not labeled) of the distal surface 108, terminates at a distal end 110, and is adapted to be received within the cavity 101 of the base member 78. When so received, the distal surface 108 abuts the second end 99 of the base member 78. It is also contemplated that the distal surface 108 could be spaced from the second end 99 when so received. As shown, the stem 109 is generally conical or tapered and has a generally circular cross-section. However, it is also contemplated that the stem 109 may alternatively be non-conical or non-tapered, have another suitable cross-section, or combinations thereof, provided that other elements of the phalanx component 74 are also adapted to fit such alternatives. For example, a stem 109 may have a cross-section selected from generally elliptical, square, triangular, or other suitable shape. The slot 111 is integrated with and formed around all or a portion of the stem 109 in a direction towards a longitudinal axis 112 of the phalanx articulation member 79, and it is adapted to receive a portion of the locking member 80. As shown, the slot 111 may be positioned at or proximate to the distal end 110, but it is also contemplated that it may alternatively be positioned elsewhere along the stem 109, provided that the base member 78 is correspondingly adapted. The stem 109 and slot 111 are adapted to fit within the cavity 101 of the base member 78 such that both slots 104, 111 are aligned to each receive a portion and together receive the whole of the locking member 80.

The locking member 80 is a resilient spring member having at least a first and a second configuration (not shown) and is adapted to be received within both slots 104, 111 to mechanically join the phalanx articulation member 79 with the base member 78. In some embodiments, the phalanx articulation member 79 and the base member 78 are permanently joined, and as such are effectively a single component of the implantable device. As shown, the locking member 80 is non-continuous and has a generally circular cross-section. However, it is also contemplated that the locking member 80 may alternatively be continuous, have an different cross-section, or combinations thereof, provided that other elements (including, but not limited to the slots 104, 111) of the phalanx component 74 are correspondingly adapted. For example, a locking member 80 could have a cross-section selected from generally elliptical, square, triangular, or other suitable cross-section. In some embodiments, the locking member 80 may comprise a resilient material suitable for surgical implants.

In some embodiments of assembly, the locking member 80 is flexed from a first to a second configuration upon insertion through the partially shared second ends 99, 103 of the base member 78 and cavity 101; remains in the second configuration as it is advanced along the cavity 101 towards the first end 102; and upon encountering the slot 104 flexes from the second to the first configuration as it is received within the slot 104. Alternatively, it is contemplated that the locking member 80 may flex from the second to an intermediate third configuration as it is received within the slot 104.

In some embodiments of assembly, a portion of the locking member 80 is received within the slot 111 of the phalanx articulating member 79; the stem 109 of said articulating member 79 is inserted through the shared ends 99, 103 of the base member 78 and cavity 101 as the locking member 80 flexes from a first to a second configuration; the locking member 80 remains in the second configuration as it and the stem 109 are advanced along the cavity 101 towards the first end 102; and upon encountering the slot 104 of the base member 78, the locking member 80 flexes from the second to the first configuration as it is received within the slot 104. Alternatively, it is contemplated that the locking member 80 may flex from the second to an intermediate third configuration as it is received within the slot 104.

Referring to FIGS. 11-19, illustrated are various examples of implantable devices of the invention which are designed to replace all or a portion of a metatarsophalangeal joint. Such devices comprise one or more of: (i) a metatarsal component for surgical implantation into the distal end of a metatarsal bone, comprising a metatarsal articulation member comprising a substantially convex bearing surface and a locking member; and a base member adapted to be fixed within the metatarsal bone, the base member comprising a cavity adapted to receive the locking member; wherein when the locking member is received by the cavity, the metatarsal articulation member is mechanically joined to the base member; and (ii) a phalanx component for surgical implantation into the proximal end of a proximal phalanx bone, comprising a phalanx articulation member comprising a substantially concave bearing surface and a locking member; and a base member adapted to be fixed within the phalanx bone, the base member comprising a cavity adapted to receive the locking member; wherein when the locking member is received by the cavity, the phalanx articulation member is mechanically joined to the base member.

In those embodiment wherein one of the components is implanted, the chosen component is adapted to cooperatively engage with and move with respect to either the proximal end of the proximal phalanx bone or the distal end of the metatarsal bone. In those embodiments wherein both of the components are implanted, the metatarsal component and the phalanx component are adapted to cooperatively engage such that the metatarsal articulation member and the phalanx articulation member move with respect to each other and collectively serve as a prosthetic metatarsophalangeal joint.

Figure 11:
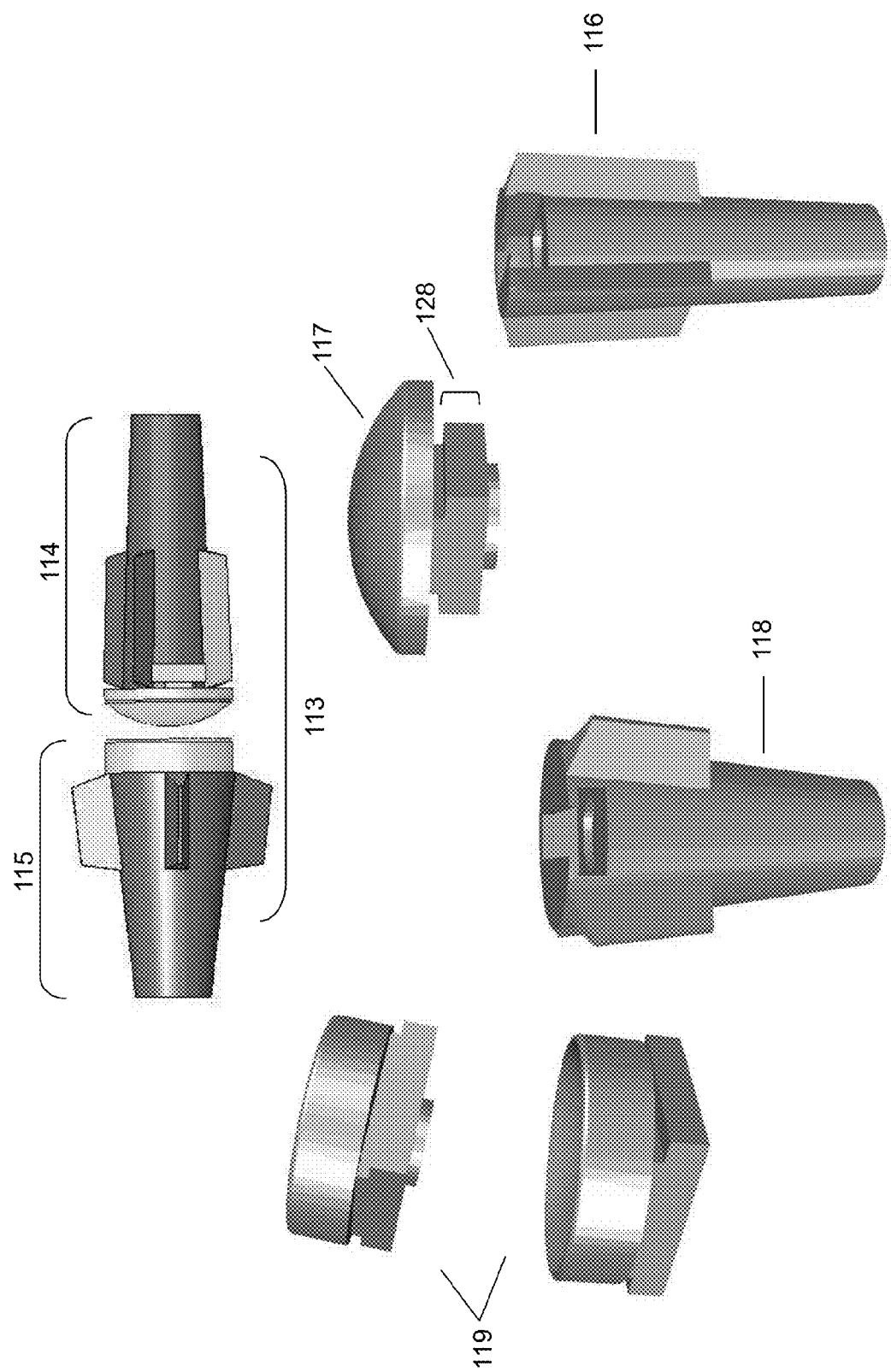
FIGS. 11-13 also illustrate one example of an implantable two-component device and elements thereof.

Referring to FIG. 11, illustrated is one example of a two-component implant device 113 comprising a metatarsal component 114 and a phalanx component 115. The metatarsal component 114 is designed to be implanted into the distal end of a resected metatarsal bone to replace all or a portion of the metatarsal head and function as the metatarsal component of the metatarsophalangeal joint. The metatarsal component 114 comprises a base member 116 and a metatarsal articulation member 117. The base member 116 may be of any suitable length and dimension to allow for fixation within the metatarsal bone, and may be fixed by any medically suitable means. In some embodiments, the base member 116 is designed to be implanted in approximately one third of the length of the metatarsal bone. In some embodiments, it is designed to be fixed by tension on the interior cavity of the resected bone.

The phalanx component 115 is designed to be implanted into the proximal end of a resected proximal phalanx bone to replace all or a portion of the proximal end of the proximal phalanx and function as the phalanx component of the metatarsophalangeal joint. The phalanx component 115 comprises a base member 118 and a phalanx articulation member 119. The base member 118 may be of any suitable length and dimension to allow for fixation within the phalanx bone, and may be fixed by any medically suitable means. In some embodiments, the base member 118 is designed to be implanted in approximately half of the length of the phalanx bone. In some embodiments, it is designed to be fixed by tension on the interior cavity of the resected bone.

In some embodiments, one or both of the metatarsal component 114 and the phalanx component 115 are implanted into the human foot to replace all or a portion of the metatarsophalangeal joint. In some embodiments, one or both components 114, 115 may be implanted in a primary resectional arthroplasty procedure, in a revision arthroplasty procedure performed to replace or compensate for a failed implant, or combinations thereof. In some embodiments, one or both components 114, 115 are implanted in a revision arthroplasty procedure. In some embodiments, each component 114, 115 implanted may be selected from small, medium, or large sizes as necessary to approximate the anatomy of the subject. In some embodiments, the components 114, 115 may comprise one or more dimensions set forth in Table 4. In some embodiments, each component 114, 115 and elements thereof may be customized to the anatomy of the subject.

TABLE 4

|  | Dimension (mm) |
|---|---|
| Metatarsal |  |
| Base Member Length | 22-26 |
| Base Member Outer Diameter Top | 7-10 |
| Base Member Outer Diameter Bottom | 5-7 |
| Cavity Length | 5-7 |
| Cavity Width | 4-5 |
| Slot Depression Diameter | 4 |
| Slot Depression Depth | 0.5 |
| Head Portion Diameter | 10-13 |
| Head Portion Height | 2 |
| Phalanx |  |
| Base Member Length | 18-22 |
| Base Member Outer Diameter Top | 10-13 |
| Base Member Outer Diameter Bottom | 6-7 |
| Cavity Length | 8-11 |
| Cavity Width | 4-5 |
| Slot Depression Diameter | 5 |
| Slot Depression Depth | 0.5 |
| Head Portion Diameter | 10-13 |
| Head Portion Depth | 2 |

Figure 12:
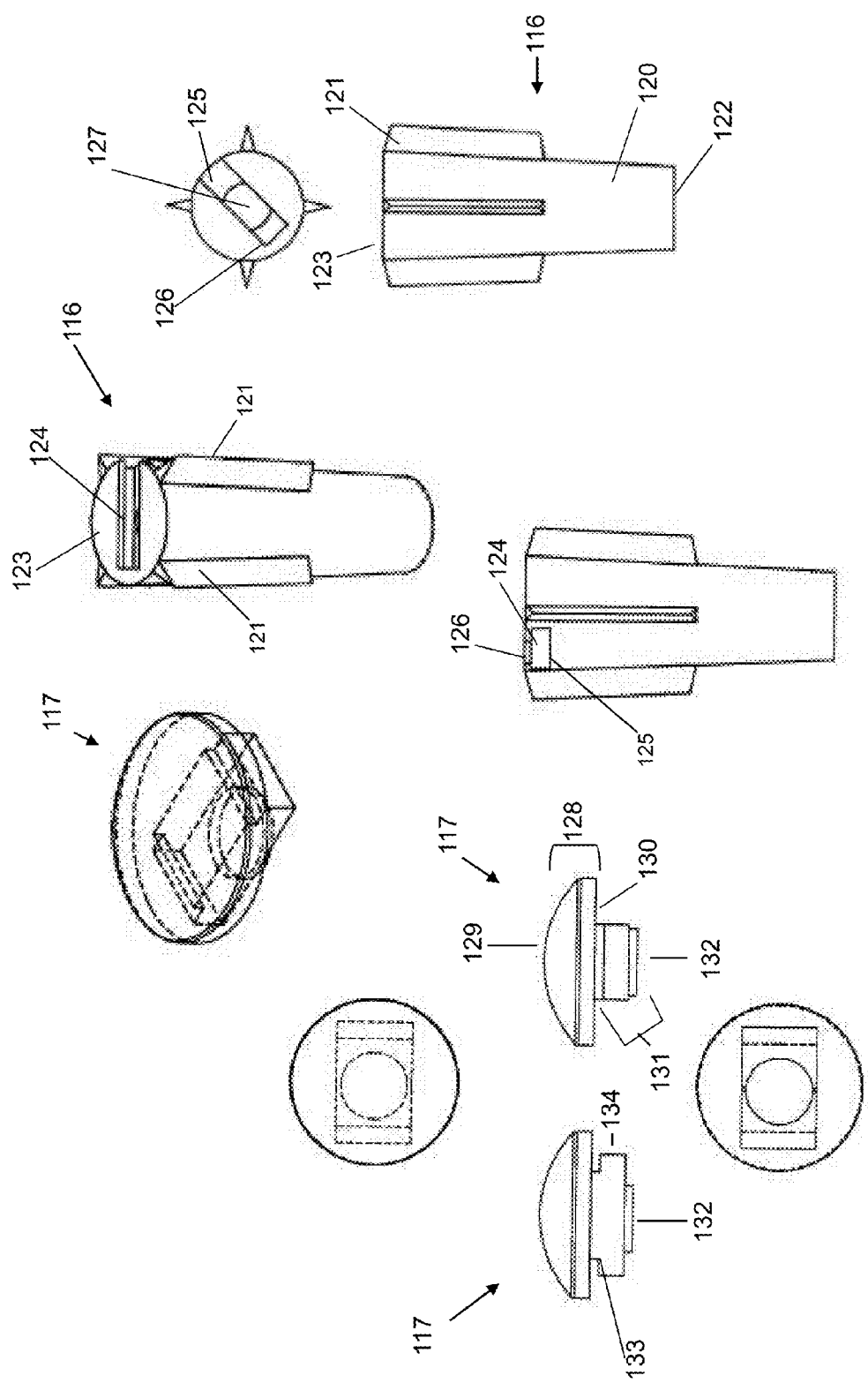

A further illustrated in FIG. 12, the base member 116 of the metatarsal component 114 comprises primary 120 and secondary 121 body portions. The primary body portion 120 is conical or tapered and has a generally circular cross-section. However, it is also contemplated that the primary body portion 120 may alternatively be non-conical or non-tapered, have another suitable cross-section, or combinations thereof, provided that other elements of the metatarsal component 114 are also adapted to fit such alternatives. For example, a primary body portion 120 may have a cross-section selected from generally elliptical, square, triangular, or other suitable shape. The secondary body portion 121 comprises one or more flanges peripherally positioned around the primary body portion 120. As shown, the secondary body portion 121 comprises four flanges equidistantly positioned around the periphery of the primary body portion 120. Each of said flanges has a generally triangular cross-section, a length approximately half that of the primary body portion 120, one end (not labeled) positioned at the second end 123 of the base member 116, and runs longitudinally along the primary body portion 120. However, it is contemplated that the secondary body portion 121 may have fewer or more flanges, that the flanges may have another suitable cross-section (for example, generally elliptical, square, or other suitable shape), that the flanges may have another suitable length, that the flanges may be suitably spaced or positioned in a different manner, and combinations thereof. In some embodiments, the secondary body portion 121 may be a resilient spring member adapted to be received within the interior cavity of a resected bone, wherein upon insertion into the cavity, the secondary body portion 121 flexes from a first to a second configuration (not shown) that exerts sufficient tension on the cavity to fix the base member 116. In some embodiments, the secondary body portion 121 may comprise a resilient material suitable for surgical implants.

The base member 116 comprises a continuous first end 122, a non-continuous second end 123, and a cavity 124 for receiving a portion of the metatarsal articulation member 117. The cavity 124 comprises a first end 125 recessed within the base member 116, a second end 126 that is partially shared with the second end 123 of the base member 116, and a slot 127 for receiving a portion of a locking member 131. As shown, the cavity 124 has a generally rectangular cross-section. However, it is also contemplated that the cavity 124 may alternatively have another suitable cross-section, provided that other elements of the metatarsal component 114 are also adapted to fit such alternatives. For example, a cavity 124 may have a cross-section selected from generally elliptical, square, or other suitable shape. As shown, the second end 126 of the cavity 124 is generally rectangular in shape. However, it is also contemplated that it may have another suitable shape, provided that other elements of the metatarsal component 114 are also adapted to fit such alternatives. The slot 127 is integrated with the first end 125 and formed in a direction towards the first end 122 of the base member 116. As shown, the slot 127 may be positioned at or proximate to the center (not shown) of the first end 125, but it is also contemplated that it may alternatively be positioned elsewhere on the first end 125, provided that the metatarsal articulation member 117 is correspondingly adapted.

The articulation member 117 of the metatarsal component 114 comprises a head portion 128 and a locking member 131. The head portion 128 comprises a substantially convex bearing surface 129 and a proximal surface 130 opposite thereto. As shown, the proximal surface 130 is generally planar, but it is also contemplated that it could be non-planar. The bearing surface 129 is adapted to emulate the general shape and function of the head portion of the metatarsal bone within a metatarsophalangeal joint. The locking member 131 protrudes proximally from the center (not labeled) of the proximal surface 130, terminates at a proximal end 132, and is adapted to be received within the cavity 124 of the base member 116. When so received, the proximal surface 130 abuts the second end 123 of the base member 116, and the proximal end 132 is locked within the slot 127.

The locking member 131 comprises a neck portion 133 abutting the proximal surface 130 of the metatarsal articulation member 117, a body portion 134 positioned between the neck portion 133 and the proximal end 132, and the proximal end 132. As shown, each of the neck portion 133 and body portion 134 has a generally rectangular cross-section, wherein the rectangular cross-section of the neck portion 133 has at least one of length, width, and height that is smaller than that of the rectangular cross-section of the body portion 134. It is, however, contemplated that the neck portion 133 and body portion 134 of a locking member 131 may have another suitable cross-section, dimension, or combination thereof, provided that other elements of the metatarsal component 114 are also adapted to fit such alternatives. For example, the neck portion 133 and body portion 134 could alternatively have a cross-section selected from generally elliptical, circular, square, or other suitable shape.

As shown, the proximal end 132 has a generally circular cross-section. However, it is also contemplated that the proximal end 132 may alternatively have another suitable cross-section, provided that other elements of the metatarsal component 114 are also adapted to fit such alternatives. For example, a proximal end 132 may have a cross-section selected from generally elliptical, square, triangular, or other suitable shape. The proximal end 132 is adapted to fit within the slot 127 of the cavity 124 of the base member 116.

In some embodiments, at least one of the locking member 131 and the second ends 123, 126 is suitably resilient such that the locking member 131 may be received within the cavity 124 and the proximal end 132 received within the slot 127 to mechanically join the metatarsal articulation member 117 with the base member 116. In some embodiments, one or more of the locking member 131 and second ends 123, 126 may comprise a resilient material suitable for surgical implants.

In some embodiments, the metatarsal articulation member 117 and the base member 116 are permanently joined, and as such are effectively a single component of the implantable device. In some embodiments of assembly, the second ends 123, 126 may be flexed from a first to a second configuration upon insertion of the locking member 131 into the cavity 124; remain in the second configuration as the locking member 131 is advanced within the cavity 124; and upon the proximal end 132 encountering the slot 127 flexes from the second to the first configuration as the proximal end 132 is received within the slot 127. Alternatively, it is contemplated that the second ends 123, 126 may flex from the second to an intermediate third configuration as the proximal end 132 is received within the slot 127.

Figure 13:
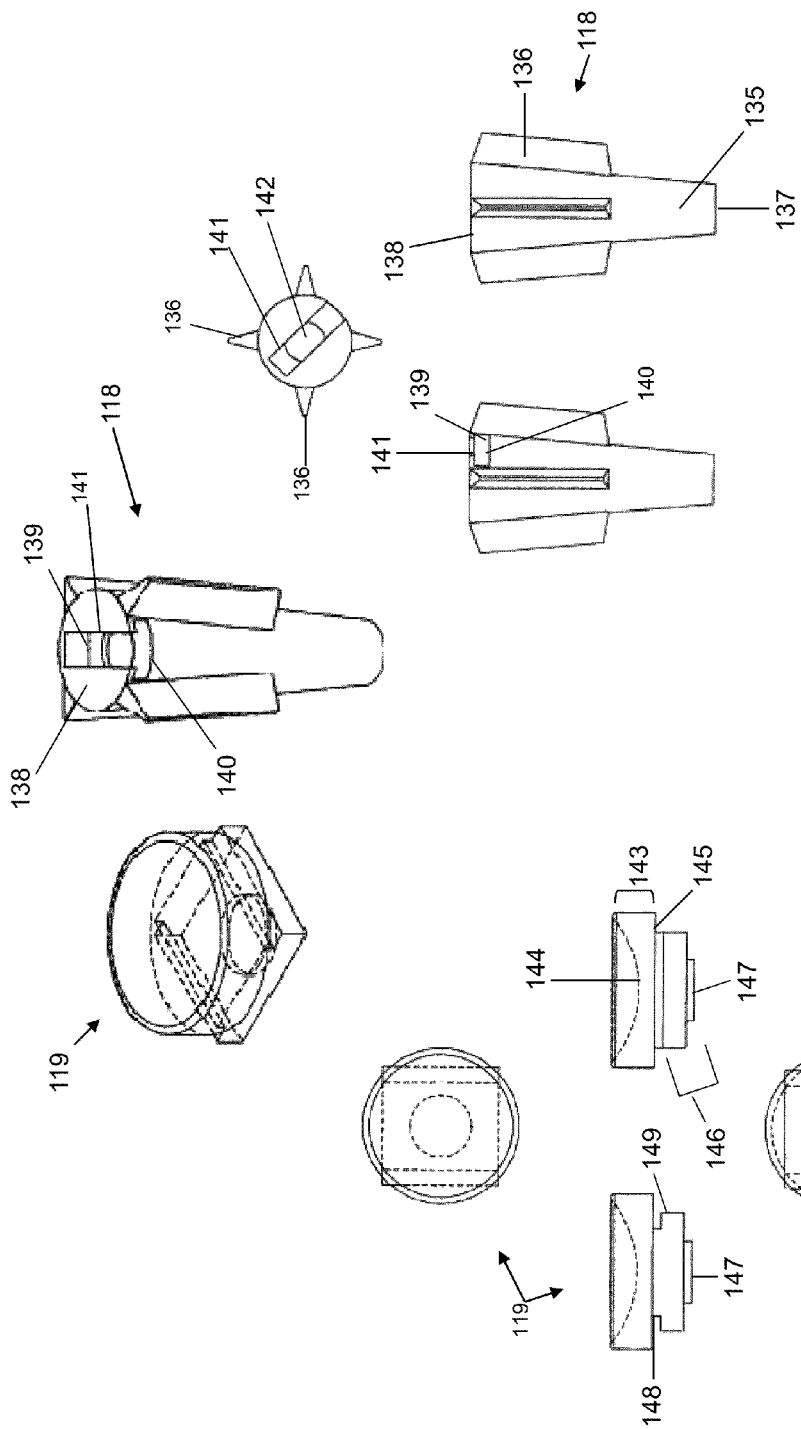

As further illustrated in FIG. 13, the base member 118 of the phalanx component 115 comprises primary 135 and secondary 136 body portions. The primary body portion 135 is conical or tapered and has a generally circular cross-section. However, it is also contemplated that the primary body portion 135 may alternatively be non-conical or non-tapered, have another suitable cross-section, or combinations thereof, provided that other elements of the phalanx component 115 are also adapted to fit such alternatives. For example, a primary body portion 135 may have a cross-section selected from generally elliptical, square, triangular, or other suitable shape. The secondary body portion 136 comprises one or more flanges peripherally positioned around the primary body portion 135. As shown, the secondary body portion 136 comprises four flanges equidistantly positioned around the periphery of the primary body portion 135. Each of said flanges has a generally triangular cross-section, a length approximately half that of the primary body portion 135, one end (not labeled) positioned at the second end 138 of the base member 118, and runs longitudinally along the primary body portion 135. However, it is contemplated that the secondary body portion 136 may have fewer or more flanges, that the flanges may have another suitable cross-section (for example, generally elliptical, square, or other suitable shape), that the flanges may have another suitable length, that the flanges may be suitably spaced or positioned in a different manner, and combinations thereof. In some embodiments, the secondary body portion 136 may be a resilient spring member adapted to be received within the interior cavity of a resected bone, wherein upon insertion into the cavity, the secondary body portion 136 flexes from a first to a second configuration (not shown) that exerts sufficient tension on the bone cavity to fix the base member 118. In some embodiments, the secondary body portion 136 may comprise a resilient material suitable for surgical implants.

The base member 118 comprises a continuous first end 137, a non-continuous second end 138, and a cavity 139 for receiving a portion of the phalanx articulation member 119. The cavity 139 comprises a first end 140 recessed within the base member 118, a second end 141 that is partially shared with the second end 138 of the base member 118, and a slot 142 for receiving a portion of a locking member 146. As shown, the cavity 139 has a generally rectangular cross-section. However, it is also contemplated that the cavity 139 may alternatively have another suitable cross-section, provided that other elements of the phalanx component 115 are also adapted to fit such alternatives. For example, a cavity 139 may have a cross-section selected from generally elliptical, square, or other suitable shape. As shown, the second end 140 of the cavity 139 is generally rectangular in shape. However, it is also contemplated that it may have another suitable shape, provided that other elements of the phalanx component 115 are also adapted to fit such alternatives. The slot 142 is integrated with the first end 140 and formed in a direction towards the first end 137 of the base member 118. As shown, the slot 142 may be positioned at or proximate to the center (not shown) of the first end 140, but it is also contemplated that it may alternatively be positioned elsewhere on the first end 140, provided that the phalanx articulation member 119 is correspondingly adapted.

The articulation member 119 of the phalanx component 115 comprises a head portion 143 and a locking member 146. The head portion 143 comprises a substantially concave bearing surface 144 and a distal surface 145 opposite thereto. As shown, the distal surface 145 is generally planar, but it is also contemplated that it could be non-planar. The bearing surface 144 is adapted to emulate the general shape and function of the proximal portion of the proximal phalanx bone within a metatarsophalangeal joint. The locking member 146 protrudes distally from the center (not labeled) of the distal surface 145, terminates at a distal end 147, and is adapted to be received within the cavity 139 of the base member 118. When so received, the distal surface 145 abuts the second end 138 of the base member 118, and the distal end 147 is locked within the slot 142.

The locking member 146 comprises a neck portion 148 abutting the distal surface 145 of the phalanx articulation member 119, a body portion 149 positioned between the neck portion 148 and the distal end 147, and the distal end 147. As shown, each of the neck portion 148 and body portion 149 has a generally rectangular cross-section, wherein the rectangular cross-section of the neck portion 148 has at least one of length, width, and height that is smaller than that of the rectangular cross-section of the body portion 149. It is, however, contemplated that the neck portion 148 and body portion 149 of a locking member 146 may have another suitable cross-section, dimension, or combination thereof, provided that other elements of the phalanx component 115 are also adapted to fit such alternatives. For example, the neck portion 148 and body portion 149 could alternatively have a cross-section selected from generally elliptical, circular, square, or other suitable shape.

As shown, the distal end 147 has a generally circular cross-section. However, it is also contemplated that the distal end 147 may alternatively have another suitable cross-section, provided that other elements of the phalanx component 115 are also adapted to fit such alternatives. For example, the distal end 147 may have a cross-section selected from generally elliptical, square, triangular, or other suitable shape. The distal end 147 is adapted to fit within the slot 142 of the cavity 139 of the base member 118.

In some embodiments, at least one of the locking member 146 and the second ends 138, 141 is suitably flexible such that the locking member 146 may be received within the cavity 139 and the distal end 147 received within the slot 142 to mechanically join the phalanx articulation member 119 with the base member 118. In some embodiments, one or more of the locking member 146, and the second ends 138, 141 may comprise a resilient material suitable for surgical implants.

In some embodiments, the phalanx articulation member 119 and the base member 118 are permanently joined, and as such are effectively a single component of the implantable device. In some embodiments of operation, the second ends 138, 141 may be flexed from a first to a second configuration upon insertion of the locking member 146 into the cavity 139, remain in the second configuration as the locking member 146 is advanced within the cavity 139, and upon the distal end 147 encountering the slot 142 flexes from the second to the first configuration as the distal end 147 is received within the slot 142. Alternatively, it is contemplated that the second ends 138, 141 may flex from the second to an intermediate third configuration as the distal end 147 is received within the slot 142.

Figure 14:
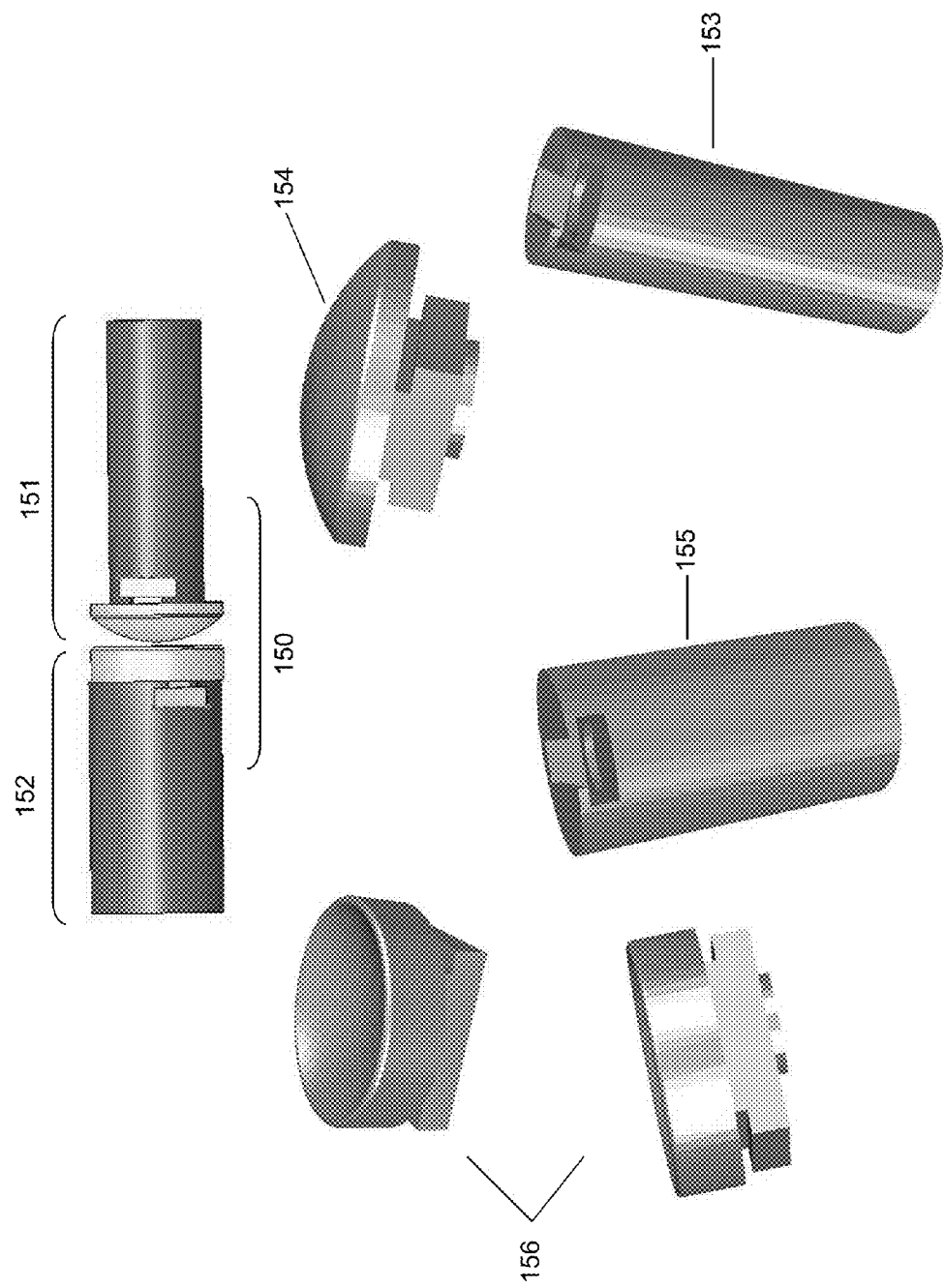
Figure 15:
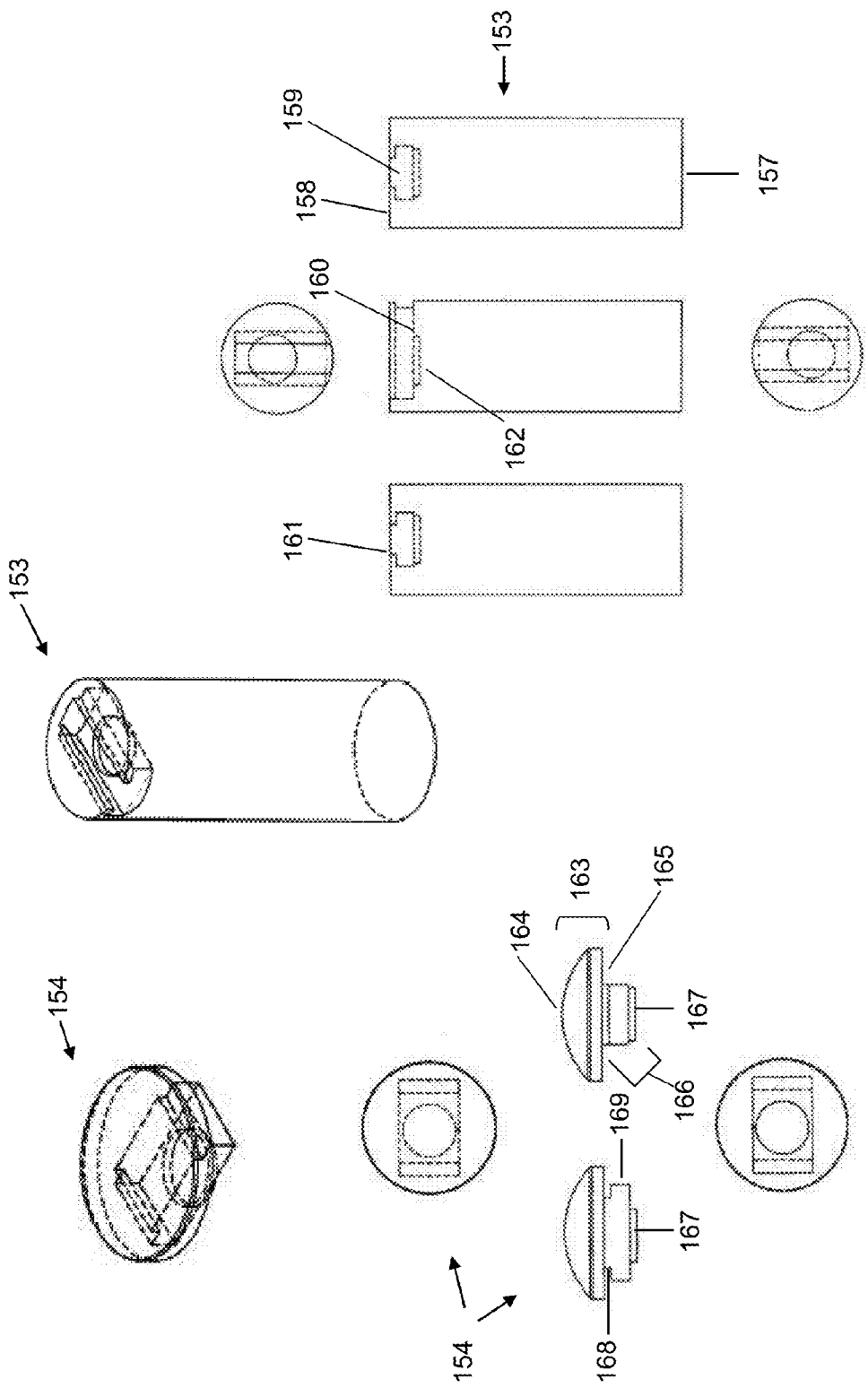

Referring to FIGS. 14-16, illustrated is another example of a two-component implant 150 comprising a metatarsal component 151 and a phalanx component 152. The metatarsal component 151 is designed to be implanted into the distal end of a resected metatarsal bone to replace all or a portion of the metatarsal head and function as the metatarsal component of the metatarsophalangeal joint. The metatarsal component 151 comprises a base member 153 and a metatarsal articulation member 154. The base member 153 may be of any suitable length and dimension to allow for fixation within the metatarsal bone, and may be fixed by any medically suitable means. In some embodiments, the base member 153 is designed to be implanted in approximately one third of the length of the metatarsal bone. In some embodiments, it may be fixed with bone cement.

The phalanx component 152 is designed to be implanted into the proximal end of a resected proximal phalanx bone to replace all or a portion of the proximal end of the proximal phalanx and function as the phalanx component of the metatarsophalangeal joint. The phalanx component 152 comprises a base member 155 and a phalanx articulation member 156. The base member 155 may be of any suitable length and dimension to allow for fixation within the phalanx bone, and may be fixed by any medically suitable means. In some embodiments, the base member 155 is designed to be implanted in approximately half of the length of the phalanx bone. In some embodiments, it may be fixed with bone cement.

In some embodiments, one or both of the metatarsal component 151 and the phalanx component 152 are implanted into the human foot to replace all or a portion of the metatarsophalangeal joint. In some embodiments, one or both components 151, 152 may be implanted in a primary resectional arthroplasty procedure, in a revision arthroplasty procedure performed to replace or compensate for a failed implant, or combinations thereof. In some embodiments, one or both components 151, 152 are implanted in a primary resectional arthroplasty procedure. In some embodiments, each component 151, 152 implanted may be selected from small, medium, or large sizes as necessary to approximate the anatomy of the subject. In some embodiments, the components 151, 152 may comprise one or more dimensions set forth in Table 5. In some embodiments, each component 151, 152 and elements thereof may be customized to the anatomy of the subject.

TABLE 5

|  | Dimension (mm) |
|---|---|
| Metatarsal | |
| Base Member Length | 22-26 |
| Base Member Outer Diameter Top | 7-10 |
| Base Member Outer Diameter Bottom | 7-10 |
| Cavity Length | 5-8 |
| Cavity Width | 4-5 |
| Slot Depression Diameter | 5 |
| Slot Depression Depth | 0.5 |
| Head Portion Diameter | 10-13 |
| Head Portion Height | 2 |
| Phalanx | |
| Base Member Length | 18-22 |
| Base Member Outer Diameter Top | 10-13 |
| Base Member Outer Diameter Bottom | 10-13 |

TABLE 5-continued

|  | Dimension (mm) |
| --- | --- |
| Cavity Length | 8-11 |
| Cavity Width | 4-5 |
| Slot Depression Diameter | 5 |
| Slot Depression Depth | 0.5 |
| Head Portion Diameter | 10-13 |
| Head Portion Depth | 2 |

A further illustrated in FIG. 15, the base member 153 of the metatarsal component 151 is cylindrical and has a generally circular cross-section. However, it is also contemplated that the base member 153 may alternatively be non-cylindrical, have another suitable cross-section, or combinations thereof, provided that other elements of the metatarsal component 151 are also adapted to fit such alternatives. For example, a base member 153 may have a cross-section selected from generally elliptical, square, triangular, or other suitable shape. The base member 153 comprises a continuous first end 157, a non-continuous second end 158, and a cavity 159 for receiving a portion of the metatarsal articulation member 154. The cavity 159 comprises a first end 160 recessed within the base member 153, a second end 161 that is partially shared with the second end 158 of the base member 153, and a slot 162 for receiving a portion of a locking member 166. As shown, the cavity 159 has a generally rectangular cross-section. However, it is also contemplated that the cavity 159 may alternatively have another suitable cross-section, provided that other elements of the metatarsal component 151 are also adapted to fit such alternatives. For example, a cavity 159 may have a cross-section selected from generally elliptical, square, or other suitable shape.

As shown, the second end 160 of the cavity 159 is generally rectangular in shape. However, it is also contemplated that it may have another suitable shape, provided that other elements of the metatarsal component 151 are also adapted to fit such alternatives. The slot 162 is integrated with the first end 160 and formed in a direction towards the first end 157 of the base member 153. As shown, the slot 162 may be positioned at or proximate to the center (not shown) of the first end 160, but it is also contemplated that it may alternatively be positioned elsewhere on the first end 160, provided that the metatarsal articulation member 154 is correspondingly adapted.

The articulation member 154 of the metatarsal component 151 comprises a head portion 163 and a locking member 166. The head portion 163 comprises a substantially convex bearing surface 164 and a proximal surface 165 opposite thereto. As shown, the proximal surface 165 is generally planar, but it is also contemplated that it could be non-planar. The bearing surface 164 is adapted to emulate the general shape and function of the head portion of the metatarsal bone within a metatarsophalangeal joint. The locking member 166 protrudes proximally from the center (not labeled) of the proximal surface 165, terminates at a proximal end 167, and is adapted to be received within the cavity 159 of the base member 153. When so received, the proximal surface 165 abuts the second end 158 of the base member 153, and the proximal end 167 is locked within the slot 162.

The locking member 166 comprises a neck portion 168 abutting the proximal surface 165 of the metatarsal articulation member 154, a body portion 169 positioned between the neck portion 168 and the proximal end 167, and the proximal end 167. As shown, each of the neck portion 168 and body portion 169 has a generally rectangular cross-section, wherein the rectangular cross-section of the neck portion 168 has at least one of length, width, and height that is smaller than that of the rectangular cross-section of the body portion 169. It is, however, contemplated that the neck portion 168 and body portion 169 of a locking member 166 may have another suitable cross-section, dimension, or combination thereof, provided that other elements of the metatarsal component 151 are also adapted to fit such alternatives. For example, the neck portion 168 and body portion 169 could alternatively have a cross-section selected from generally elliptical, circular, square, or other suitable shape.

As shown, the proximal end 167 has a generally circular cross-section. However, it is also contemplated that the proximal end 167 may alternatively have another suitable cross-section, provided that other elements of the metatarsal component 151 are also adapted to fit such alternatives. For example, a proximal end 167 may have a cross-section selected from generally elliptical, square, triangular, or other suitable shape. The proximal end 167 is adapted to fit within the slot 162 of the cavity 159 of the base member 153.

In some embodiments, at least one of the locking member 166 and the second ends 158, 161 is suitably flexible such that the locking member 166 may be received within the cavity 159 and the proximal end 167 received within the slot 162 to mechanically join the metatarsal articulation member 154 with the base member 153. In some embodiments, one or more of the locking member 166 and the second ends 158, 161 may comprise a resilient material suitable for surgical implants. In some embodiments, the metatarsal articulation member 154 and the base member 153 are permanently joined, and as such are effectively a single component of the implantable device. In some embodiments of assembly, the second ends 158, 161 may be flexed from a first to a second configuration upon insertion of the locking member 166 into the cavity 159; remain in the second configuration as the locking member 166 is advanced within the cavity 159; and upon the proximal end 167 encountering the slot 162 flexes from the second to the first configuration as the proximal end 167 is received within the slot 162. Alternatively, it is contemplated that the second ends 158, 161 may flex from the second to an intermediate third configuration as the proximal end 167 is received within the slot 162.

A further illustrated in FIG. 16, the base member 155 of the phalanx component 152 is cylindrical and has a generally circular cross-section. However, it is also contemplated that the base member 155 may alternatively be non-cylindrical, have another suitable cross-section, or combinations thereof, provided that other elements of the phalanx component 152 are also adapted to fit such alternatives. For example, a base member 155 may have a cross-section selected from generally elliptical, square, triangular, or other suitable shape. The base member 155 comprises a continuous first end 170, a non-continuous second end 171, and a cavity 172 for receiving a portion of the phalanx articulation member 156. The cavity 172 comprises a first end 173 recessed within the base member 155, a second end 174 that is partially shared with the second end 171 of the base member 155, and a slot 175 for receiving a portion of a locking member 179. As shown, the cavity 172 has a generally rectangular cross-section. However, it is also contemplated that the cavity 172 may alternatively have another suitable cross-section, provided that other elements of the phalanx component 152 are also adapted to fit such alternatives. For example, a cavity 172 may have a cross-section selected from generally elliptical, square, or other suitable shape. As shown, the second end 174 of the cavity 172 is generally rectangular in shape. However, it is also contemplated that it may have another suitable shape, provided that other elements of the phalanx component 152 are also adapted to fit such alternatives. The slot 175 is integrated with the first end 173 and formed in a direction towards the first end 170 of the base member 155. As shown, the slot 175 may be positioned at or proximate to the center (not shown) of the first end 173, but it is also contemplated that it may alternatively be positioned elsewhere on the first end 173, provided that the phalanx articulation member 156 is correspondingly adapted.

The articulation member 156 of the phalanx component 152 comprises a head portion 176 and a locking member 179. The head portion 176 comprises a substantially concave bearing surface 177 and a distal surface 178 opposite thereto. As shown, the distal surface 178 is generally planar, but it is also contemplated that it could be non-planar. The bearing surface 177 is adapted to emulate the general shape and function of the proximal portion of the proximal phalanx bone within a metatarsophalangeal joint. The locking member 179 protrudes distally from the center (not labeled) of the distal surface 178, terminates at a distal end 180, and is adapted to be received within the cavity 172 of the base member 155. When so received, the distal surface 178 abuts the second end 171 of the base member 155, and the distal end 180 is locked within the slot 175.

The locking member 179 comprises a neck portion 181 abutting the distal surface 178 of the phalanx articulation member 156, a body portion 182 positioned between the neck portion 181 and the distal end 180, and the distal end 180. As shown, each of the neck portion 181 and body portion 182 has a generally rectangular cross-section, wherein the rectangular cross-section of the neck portion 181 has at least one of length, width, and height that is smaller than that of the rectangular cross-section of the body portion 182. It is, however, contemplated that the neck portion 181 and body portion 182 of a locking member 179 may have another suitable cross-section, dimension, or combination thereof, provided that other elements of the phalanx component 152 are also adapted to fit such alternatives. For example, the neck portion 181 and body portion 182 could alternatively have a cross-section selected from generally elliptical, circular, square, or other suitable shape.

As shown, the distal end 180 has a generally circular cross-section. However, it is also contemplated that the distal end 180 may alternatively have another suitable cross-section, provided that other elements of the phalanx component 152 are also adapted to fit such alternatives. For example, a distal end 180 may have a cross-section selected from generally elliptical, square, triangular, or other suitable shape. The distal end 180 is adapted to fit within the slot 175 of the cavity 172 of the base member 155.

In some embodiments, at least one of the locking member 179 and the second ends 171, 174 is suitably flexible such that the locking member 179 may be received within the cavity 172 and the distal end 180 received within the slot 172 to mechanically join the phalanx articulation member 156 with the base member 155. In some embodiments, one or more of the locking member 179 and the second ends 171, 174 may comprise a resilient material suitable for surgical implants. In some embodiments, the phalanx articulation member 156 and the base member 155 are permanently joined, and as such are effectively a single component of the implantable device. In some embodiments of assembly, the second ends 171, 174 may be flexed from a first to a second configuration upon insertion of the locking member 179 into the cavity 172; remain in the second configuration as the locking member 179 is advanced within the cavity 172; and upon the distal end 180 encountering the slot 175 flexes from the second to the first configuration as the distal end 180 is received within the slot 175. Alternatively, it is contemplated that the second ends 171, 174 may flex from the second to an intermediate third configuration as the distal end 180 is received within the slot 175.

Figure 17:
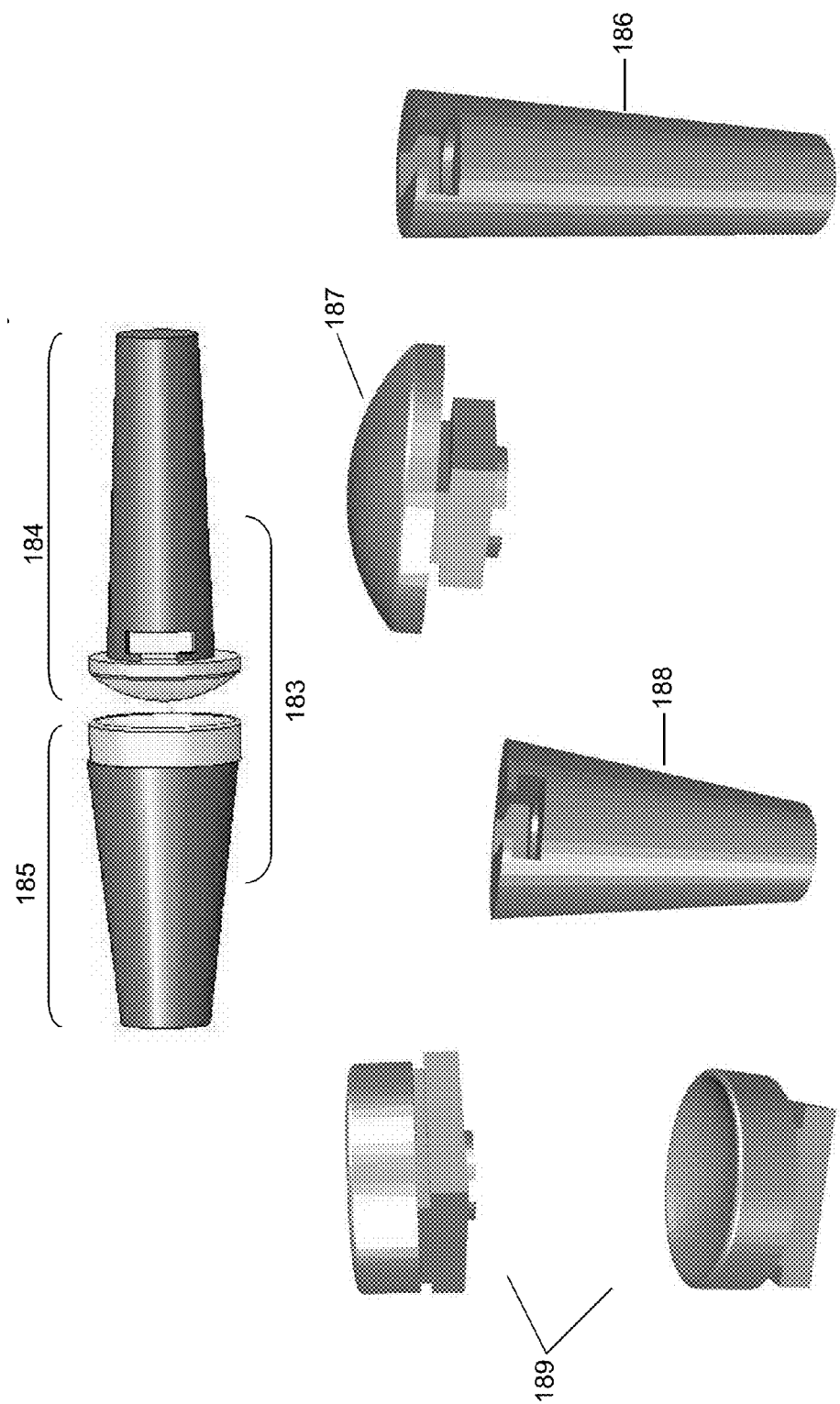
FIGS. 17-19 illustrate a further example of an implantable two-component device and elements thereof.
Figure 18:
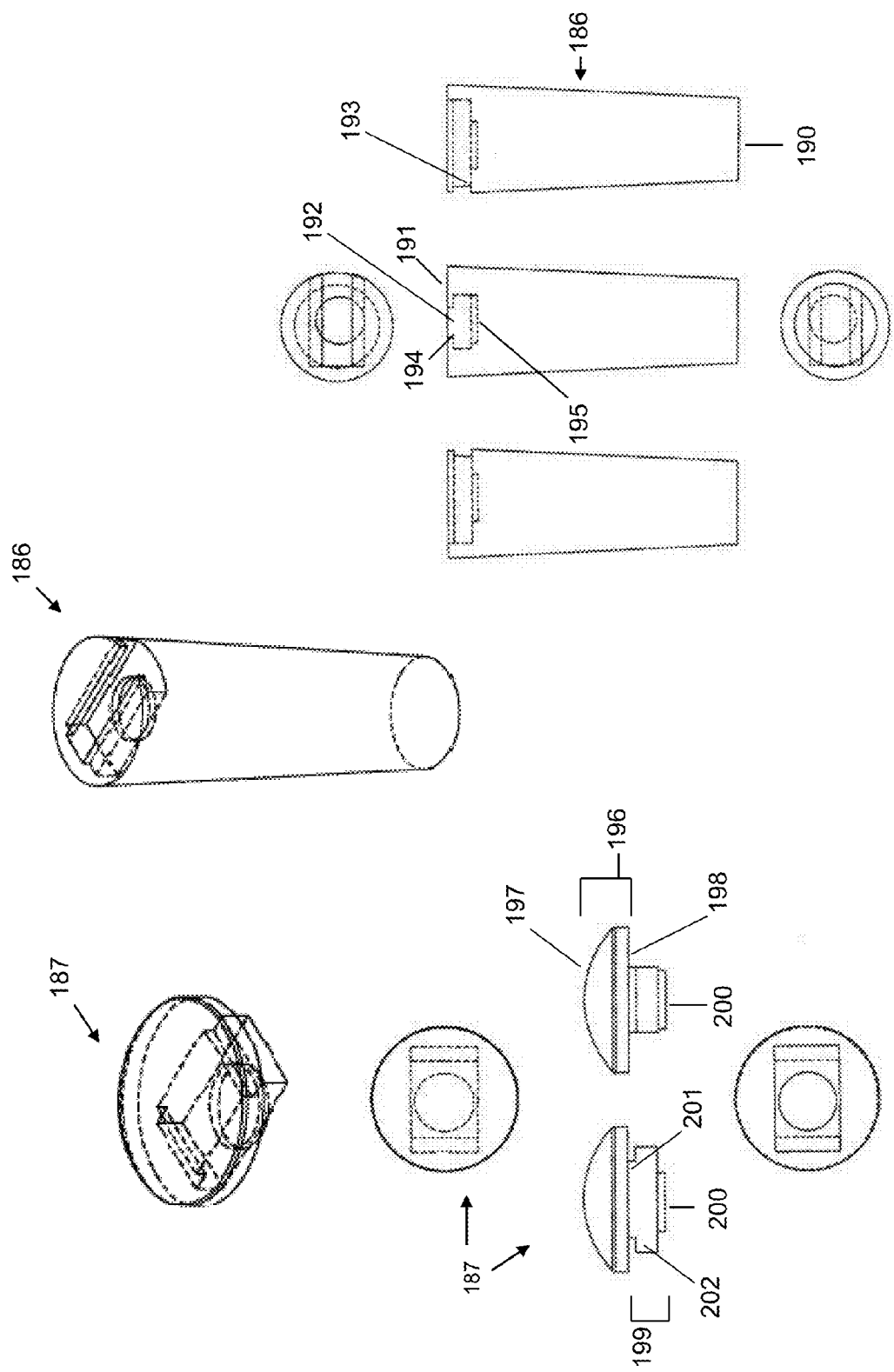
Figure 19:
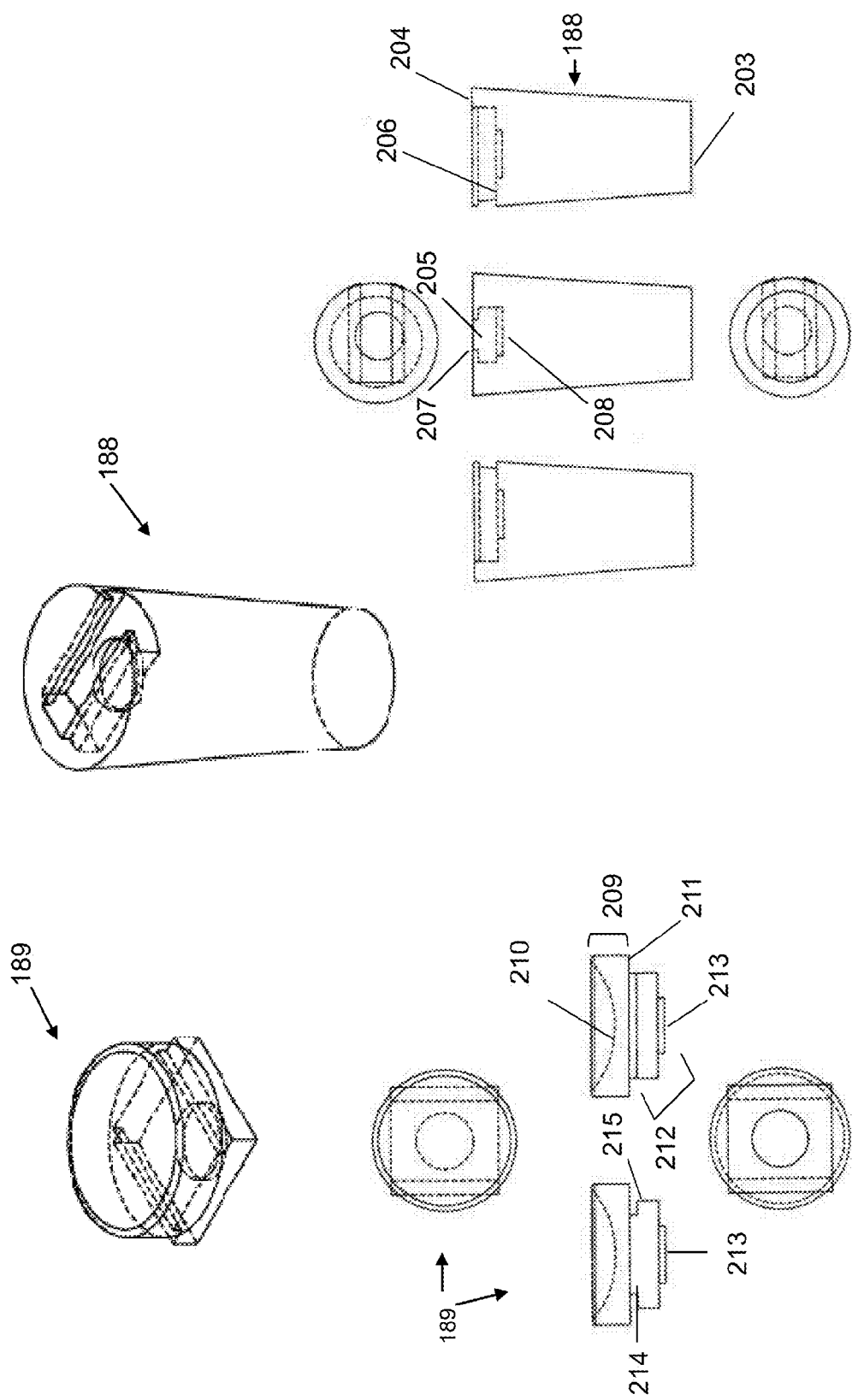

Referring to FIGS. 17-19, illustrated is another example of a two-component device 183 comprising a metatarsal component 184 and a phalanx component 185. The metatarsal component 184 is designed to be implanted into the distal end of a resected metatarsal bone to replace all or a portion of the metatarsal head and function as the metatarsal component of the metatarsophalangeal joint. The metatarsal component 184 comprises a base member 186 and a metatarsal articulation member 187. The base member 186 may be of any suitable length and dimension to allow for fixation within the metatarsal bone, and may be fixed by any medically suitable means. In some embodiments, the base member 186 is designed to be implanted in approximately one third of the length of the metatarsal bone. In some embodiments, it may be fixed with bone cement.

The phalanx component 185 is designed to be implanted into the proximal end of a resected proximal phalanx bone to replace all or a portion of the proximal end of the proximal phalanx and function as the phalanx component of the metatarsophalangeal joint. The phalanx component 185 comprises a base member 188 and a phalanx articulation member 189. The base member 188 may be of any suitable length and dimension to allow for fixation within the phalanx bone, and may be fixed by any medically suitable means. In some embodiments, the base member 188 is designed to be implanted in approximately half of the length of the phalanx bone. In some embodiments, it may be fixed with bone cement.

In some embodiments, one or both of the metatarsal component 184 and the phalanx component 185 are implanted into the human foot to replace all or a portion of the metatarsophalangeal joint. In some embodiments, one or both components 184, 185 may be implanted in a primary resectional arthroplasty procedure, in a revision arthroplasty procedure performed to replace or compensate for a failed implant, or combinations thereof. In some embodiments, one or both components 184, 185 are implanted in a revision arthroplasty procedure. In some embodiments, each component 184, 185 implanted may be selected from small, medium, or large sizes as necessary to approximate the anatomy of the subject. In some embodiments, the components 184, 185 may comprise one or more dimensions set forth in Table 4. In some embodiments, each component 184, 185 and elements thereof may be customized to the anatomy of the subject.

A further illustrated in FIG. 18, the base member 186 of the metatarsal component 184 is conical or tapered and has a generally circular cross-section. However, it is also contemplated that the base member 186 may alternatively be non-conical or non-tapered, have another suitable cross-section, or combinations thereof, provided that other elements of the metatarsal component 184 are also adapted to fit such alternatives. For example, a base member 186 may have a cross-section selected from generally elliptical, square, triangular, or other suitable shape. The base member 186 comprises a continuous first end 190, a non-continuous second end 191, and a cavity 192 for receiving a portion of the metatarsal articulation member 187. The cavity 192 comprises a first end 193 recessed within the base member 186, a second end 194 that is partially shared with the second end 191 of the base member 186, and a slot 195 for receiving a portion of a locking member 199. As shown, the cavity 192 has a generally rectangular cross-section. However, it is also contemplated that the cavity 192 may alternatively have another suitable cross-section, provided that other elements of the metatarsal component 184 are also adapted to fit such alternatives. For example, a cavity 192 may have a cross-section selected from generally elliptical, square, or other suitable shape.

As shown, the second end 194 of the cavity 192 is generally rectangular in shape. However, it is also contemplated that it may have another suitable shape, provided that other elements of the metatarsal component 184 are also adapted to fit such alternatives. The slot 195 is integrated with the first end 193 and formed in a direction towards the first end 190 of the base member 186. As shown, the slot 195 may be positioned at or proximate to the center (not shown) of the first end 193, but it is also contemplated that it may alternatively be positioned elsewhere on the first end 193, provided that the metatarsal articulation member 187 is correspondingly adapted.

The articulation member 187 of the metatarsal component 184 comprises a head portion 196 and a locking member 199. The head portion 196 comprises a substantially convex bearing surface 197 and a proximal surface 198 opposite thereto. As shown, the proximal surface 198 is generally planar, but it is also contemplated that it could be non-planar. The bearing surface 197 is adapted to emulate the general shape and function of the head portion of the metatarsal bone within a metatarsophalangeal joint. The locking member 199 protrudes proximally from the center (not labeled) of the proximal surface 198, terminates at a proximal end 200, and is adapted to be received within the cavity 192 of the base member 186. When so received, the proximal surface 198 abuts the second end 191 of the base member 186, and the proximal end 200 is locked within the slot 195.

The locking member 199 comprises a neck portion 201 abutting the proximal surface 198 of the metatarsal articulation member 187, a body portion 202 positioned between the neck portion 201 and the proximal end 200, and the proximal end 200. As shown, each of the neck portion 201 and body portion 202 has a generally rectangular cross-section, wherein the rectangular cross-section of the neck portion 201 has at least one of length, width, and height that is smaller than that of the rectangular cross-section of the body portion 202. It is, however, contemplated that the neck portion 201 and body portion 202 of a locking member 199 may have another suitable cross-section, dimension, or combination thereof, provided that other elements of the metatarsal component 184 are also adapted to fit such alternatives. For example, the neck portion 201 and body portion 202 could alternatively have a cross-section selected from generally elliptical, circular, square, or other suitable shape.

As shown, the proximal end 200 has a generally circular cross-section. However, it is also contemplated that the proximal end 200 may alternatively have another suitable cross-section, provided that other elements of the metatarsal component 184 are also adapted to fit such alternatives. For example, a proximal end 200 may have a cross-section selected from generally elliptical, square, triangular, or other suitable shape. The proximal end 200 is adapted to fit within the slot 195 of the cavity 192 of the base member 186.

In some embodiments, at least one of the locking member 199 and the second ends 191, 194 is suitably flexible such that the locking member 199 may be received within the cavity 192 and the proximal end 200 received within the slot 195 to mechanically join the metatarsal articulation member 187 with the base member 186. In some embodiments, one or more of the locking member 199 and the second ends 191, 194 may comprise a resilient material suitable for surgical implants. In some embodiments, the metatarsal articulation member 187 and the base member 186 are permanently joined, and as such are effectively a single component of the implantable device. In some embodiments of assembly, the second ends 191, 194 may be flexed from a first to a second configuration upon insertion of the locking member 199 into the cavity 192; remain in the second configuration as the locking member 199 is advanced within the cavity 192; and upon the proximal end 200 encountering the slot 195 flexes from the second to the first configuration as the proximal end 200 is received within the slot 195. Alternatively, it is contemplated that the second ends 191, 194 may flex from the second to an intermediate third configuration as the proximal end 200 is received within the slot 195.

A further illustrated in FIG. 19, the base member 188 of the phalanx component 185 is conical or tapered and has a generally circular cross-section. However, it is also contemplated that the base member 188 may alternatively be non-conical or non-tapered, have another suitable cross-section, or combinations thereof, provided that other elements of the phalanx component 185 are also adapted to fit such alternatives. For example, a base member 188 may have a cross-section selected from generally elliptical, square, triangular, or other suitable shape. The base member 188 comprises a continuous first end 203, a non-continuous second end 204, and a cavity 205 for receiving a portion of the phalanx articulation member 189. The cavity 205 comprises a first end 206 recessed within the base member 188, a second end 207 that is partially shared with the second end 204 of the base member 188, and a slot 208 for receiving a portion of a locking member 212. As shown, the cavity 205 has a generally rectangular cross-section. However, it is also contemplated that the cavity 205 may alternatively have another suitable cross-section, provided that other elements of the phalanx component 185 are also adapted to fit such alternatives. For example, a cavity 205 may have a cross-section selected from generally elliptical, square, or other suitable shape. As shown, the second end 207 of the cavity 205 is generally rectangular in shape. However, it is also contemplated that it may have another suitable shape, provided that other elements of the phalanx component 185 are also adapted to fit such alternatives. The slot 208 is integrated with the first end 206 and formed in a direction towards the first end 203 of the base member 188. As shown, the slot 208 may be positioned at or proximate to the center (not shown) of the first end 206, but it is also contemplated that it may alternatively be positioned elsewhere on the first end 206, provided that the phalanx articulation member 189 is correspondingly adapted.

The articulation member 189 of the phalanx component 185 comprises a head portion 209 and a locking member 212. The head portion 209 comprises a substantially concave bearing surface 210 and a distal surface 211 opposite thereto. As shown, the distal surface 211 is generally planar, but it is also contemplated that it could be non-planar. The bearing surface 210 is adapted to emulate the general shape and function of the proximal portion of the proximal phalanx bone within a metatarsophalangeal joint. The locking member 212 protrudes distally from the center (not labeled) of the distal surface 211, terminates at a distal end 213, and is adapted to be received within the cavity 205 of the base member 188. When so received, the distal surface 211 abuts the second end 204 of the base member 188, and the distal end 213 is locked within the slot 208.

The locking member 212 comprises a neck portion 214 abutting the distal surface 211 of the phalanx articulation member 189, a body portion 215 positioned between the neck portion 214 and the distal end 213, and the distal end 213. As shown, each of the neck portion 214 and body portion 215 has a generally rectangular cross-section, wherein the rectangular cross-section of the neck portion 214 has at least one of length, width, and height that is smaller than that of the rectangular cross-section of the body portion 215. It is, however, contemplated that the neck portion 214 and body portion 215 of a locking member 212 may have another suitable cross-section, dimension, or combination thereof, provided that other elements of the phalanx component 185 are also adapted to fit such alternatives. For example, the neck portion 214 and body portion 215 could alternatively have a cross-section selected from generally elliptical, circular, square, or other suitable shape.

As shown, the distal end 213 has a generally circular cross-section. However, it is also contemplated that the distal end 213 may alternatively have another suitable cross-section, provided that other elements of the phalanx component 185 are also adapted to fit such alternatives. For example, a distal end 213 may have a cross-section selected from generally elliptical, square, triangular, or other suitable shape. The distal end 213 is adapted to fit within the slot 208 of the cavity 205 of the base member 188.

In some embodiments, at least one of the locking member 212 and the second ends 204, 207 is suitably flexible such that the locking member 212 may be received within the cavity 205 and the distal end 213 received within the slot 208 to mechanically join the phalanx articulation member 189 with the base member 188. In some embodiments, one or more of the locking member 212 and the second ends 204, 207 may comprise a resilient material suitable for surgical implants. In some embodiments, the phalanx articulation member 189 and the base member 188 are permanently joined, and as such are effectively a single component of the implantable device. In some embodiments of operation, the second ends 204, 207 may be flexed from a first to a second configuration upon insertion of the locking member 212 into the cavity 205; remain in the second configuration as the locking member 212 is advanced within the cavity 205; and upon the distal end 213 encountering the slot 208 flexes from the second to the first configuration as the distal end 213 is received within the slot 208. Alternatively, it is contemplated that the second ends 204, 207 may flex from the second to an intermediate third configuration as the distal end 213 is received within the slot 208.

Referring to FIGS. 20-25, illustrated are various examples of implantable devices of the invention which are designed to replace all or a portion of a metatarsophalangeal joint. Such devices comprise one or more of: (i) a metatarsal component for surgical implantation into the distal end of a metatarsal bone, comprising a metatarsal articulation member comprising a substantially convex bearing surface and a cavity adapted to receive at least a portion of a locking member; a base member adapted to be fixed within the metatarsal bone; a locking member adapted to be at least partially received by the cavity; wherein when the locking member is received within the cavity, the metatarsal articulation member is mechanically joined to the base member; and (ii) a phalanx component for surgical implantation into the proximal end of a proximal phalanx bone, comprising a phalanx articulation member comprising a substantially convex bearing surface and a cavity adapted to receive at least a portion of a locking member; a base member adapted to be fixed within the phalanx bone; a locking member adapted to be at least partially received by the cavity; wherein when the locking member is received within the cavity, the phalanx articulation member is mechanically joined to the base member.

In those embodiments wherein one of the components is implanted, the chosen component is adapted to cooperatively engage with and move with respect to either the proximal end of the proximal phalanx bone or the distal end of the metatarsal bone. In those embodiments wherein both of the components are implanted, the metatarsal component and the phalanx component are adapted to cooperatively engage such that the metatarsal articulation member and the phalanx articulation member move with respect to each other and collectively serve as a prosthetic metatarsophalangeal joint.

Figure 20:
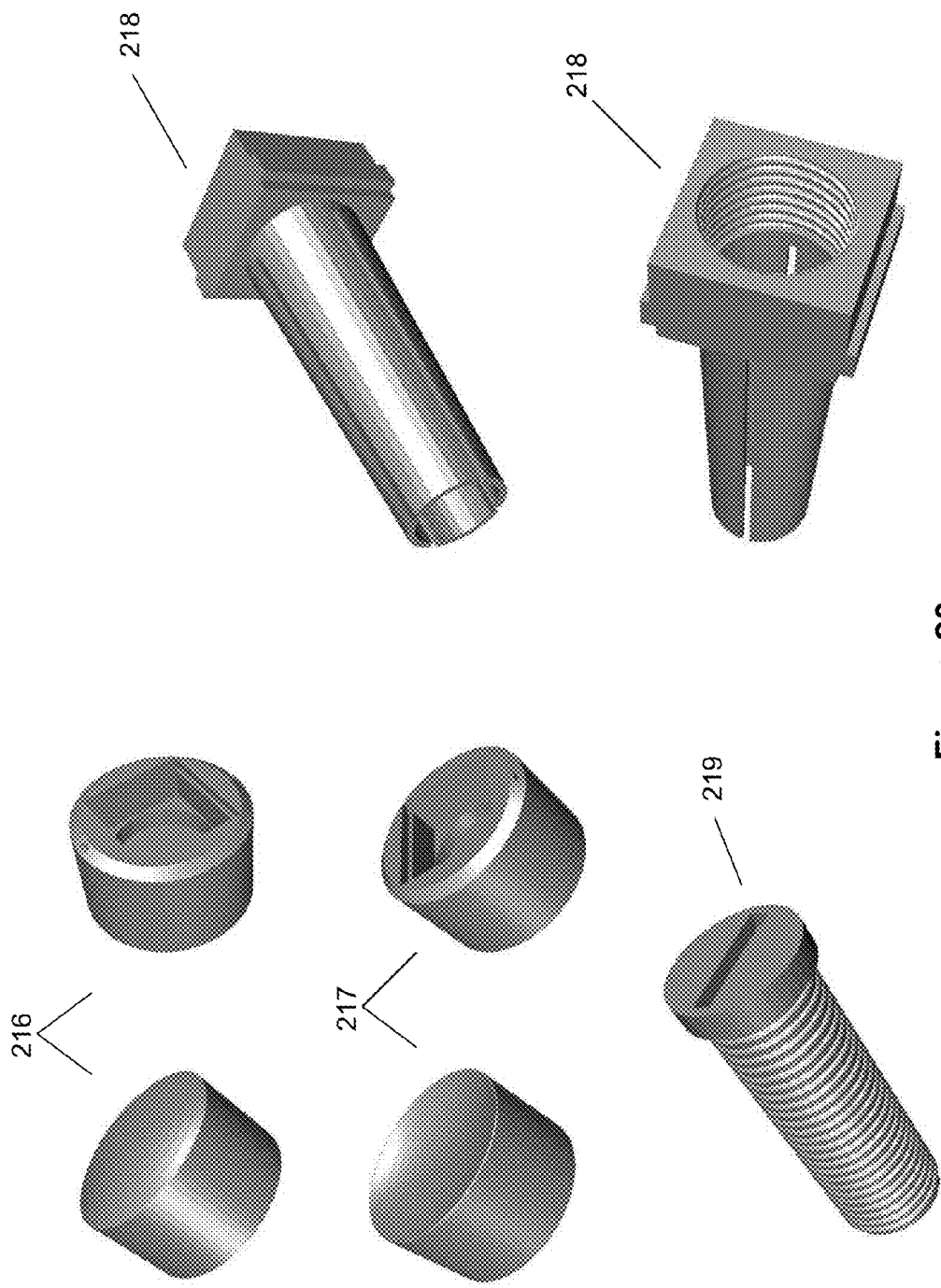
FIGS. 20-22 also illustrate an example of an implantable two-component device and elements thereof.

Referring to FIG. 20, illustrated is one example of a device comprising a metatarsal articulation member 216, a phalanx articulation member 217, a base member 218, and a screw member 219. The base member 218 is designed to be implanted into the distal end of a resected metatarsal bone, the proximal end of a resected proximal phalanx bone, or both. The base member 218 may be of any suitable length and dimension to allow for fixation within the metatarsal and phalanx bones, and may be fixed by any medically suitable means. In some embodiments, the base member 218 is designed to be implanted in approximately one third of the length of the metatarsal bone or half of the length of the phalanx bone. In some embodiments, it is designed to be fixed by tension on the interior cavity of the resected bone. When the metatarsal-implanted base member 218 is mechanically joined to the metatarsal articulation member 216, the device is designed to replace all or a portion of the metatarsal head and function as the metatarsal component of the metatarsophalangeal joint. When the phalanx-implanted base member 218 is mechanically joined to the phalanx articulation member 217, the device is designed to replace all or a portion of the proximal end of the proximal phalanx and function as the phalanx component of the metatarsophalangeal joint.

In some embodiments, the device may be implanted into one or both of the metatarsal and phalanx bones in a primary resectional arthroplasty procedure, in a revision arthroplasty procedure performed to replace or compensate for a failed implant, or combinations thereof. In some embodiments, implantation is by a revision arthroplasty procedure. In some embodiments, each device implanted may be selected from small, medium, or large sizes as necessary to approximate the anatomy of the subject. In some embodiments, the devices may comprise one or more dimensions set forth in Table 6. In some embodiments, each device and elements thereof may be customized to the anatomy of the subject.

TABLE 6

| Metatarsal and Phalanx | Dimension (mm) |
| --- | --- |
| Base Member Length Metatarsal | 22-26 |
| Base Member Length Phalange | 18-22 |
| Base Member Head Portion Height | 5-6 |
| Base Member Head Portion Without Flange | 9-10 |
| Base Member Head Portion and Flange Width | 10-11 |
| Screw Length Metatarsal | 22-26 |
| Screw Length Phalange | 18-22 |
| Screw Head Height | 2 |
| Screw Head Diameter | 9-10 |
| Articulation Member Height (Excluding Bearing Surface) | 10 |
| Articulation Member Bearing Surface Diameter | 16-22 |
| Bearing Surface Depth | 2 |
| Bearing Surface Height | 2 |

Figure 21:
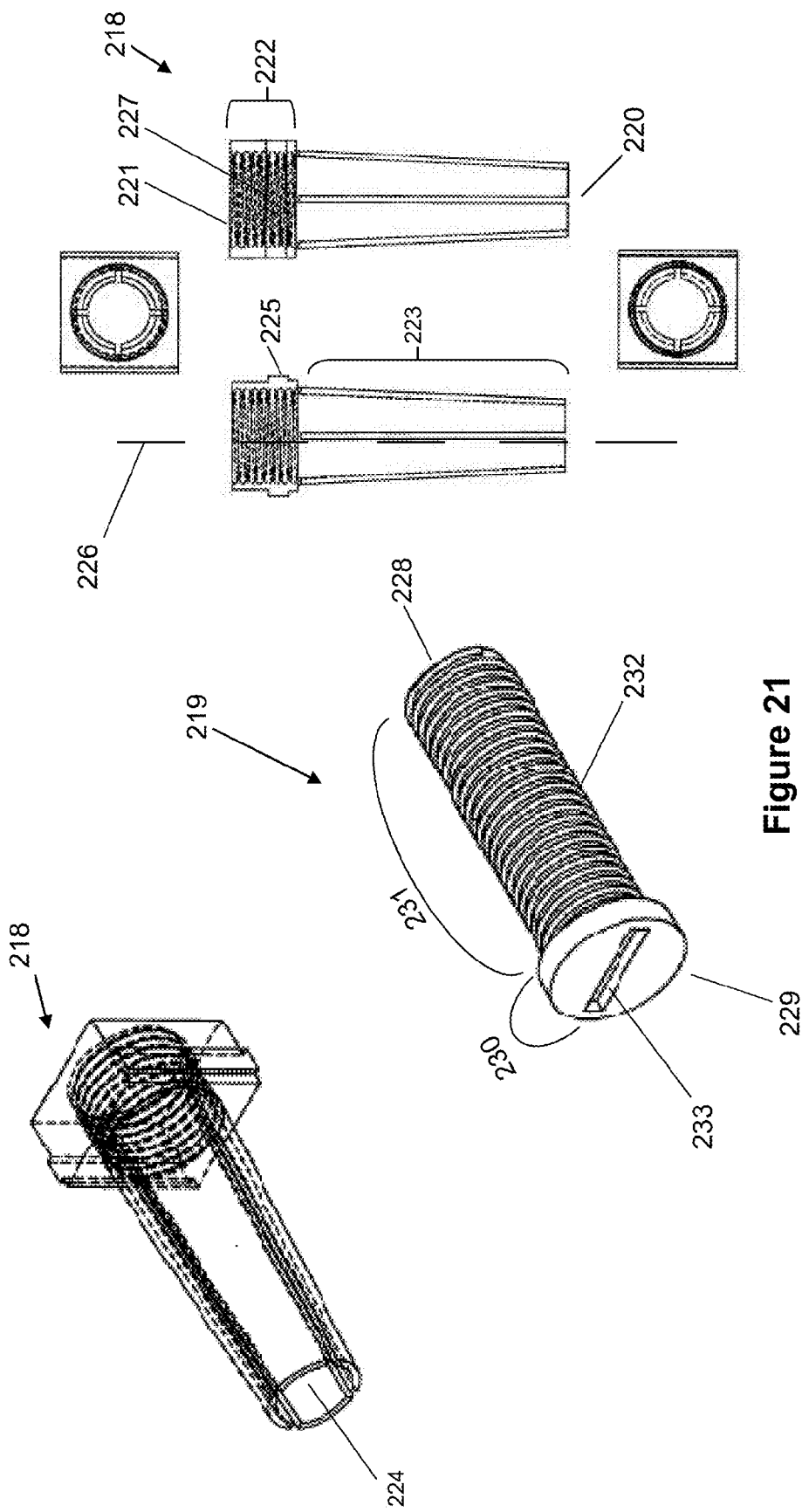

A further illustrated in FIG. 21, the base member 218 comprises a first end 220, a second end 221 comprising a head portion 222, a body portion 223, and a cavity 224 for receiving the screw member 219. As shown, the first 220 and second 221 ends are non-continuous. The cavity 224 is continuous through the base member 218 from the first end 220 to the second end 221. As shown, the cavity 224 and body portion 223 are conical or tapered and have a generally non-continuous cross-section with a generally circular shape. It is, however, contemplated that the cavity 224 and body portion 223 could alternatively be non-conical or non-tapered, have another suitable cross-section, or combinations thereof, provided that other elements of the device are also adapted to fit such alternatives. For example, a cross-section could be selected from generally elliptical, square, or other suitable shape. In some embodiments, the body portion 223 may be a resilient member adapted to be received within the interior cavity of a resected bone, wherein the body portion 223 expands in response to the screw member 219 being received and advanced within the cavity 224 and exerts sufficient tension on the bone cavity to fix the base member 218 therein. In some embodiments, the body portion 223 may comprise a resilient material suitable for surgical implants.

The head portion 222 has a generally rectangular cross-section. However, it is also contemplated that a head portion 222 could alternatively have another suitable cross-section, provided that other elements of the device are also adapted to fit such alternatives. For example, a head portion 222 could have a cross-section selected from generally elliptical, square, or other suitable shape. The head portion 222 comprises a locking member 225. In some embodiments, the locking member 225 comprises a pair of flanges, each opposably positioned on the exterior of the head portion 222. As shown, the flanges are positioned at or proximate to the body portion 223, are perpendicular to a longitudinal axis 226, and have a generally rectangular cross-section with at least one of length, width, or height that is the same as that of the cross-section of the head portion 222. It is also contemplated that the head portion 222 could comprise a locking member 225 with more than one pair of flanges, that the flanges could be alternatively positioned, that the flanges could have a different cross-section or dimension, or combinations thereof, provided that other elements of the device are also adapted to fit such alternatives. In some embodiments, the flanges are a locking member 225 adapted to mechanically join the metatarsal articulation member 216 or the phalanx articulation member 217 to the base member 218. The head portion 222 further comprises an interior (female) screw thread 227 along the portion of the cavity 224 formed within the head portion 222, said screw thread 227 adapted to receive a portion of the screw member 219.

As shown, the screw member 219 comprises a first end 228, a second end 229 comprising a head portion 230, and a body portion 231 comprising an external (male) screw thread 232. The screw thread 232 is adapted to be at least partially received by the interior screw thread 227 of the base member 218. The screw member 219 is generally cylindrical and has a generally circular cross-section. However, it is also contemplated that the screw member 219 could alternatively be non-cylindrical, have an different cross-section, or combinations thereof, provided that other elements of the device are correspondingly adapted. For example, a screw member 219 could be tapered or conical or have a helical cross-section. The head portion 230 of the screw member 219 has a cross-section larger than that of the body portion 231. Additionally, the head portion 230 comprises a slot 233 centrally positioned on the second end 229. As shown, the slot 233 has a generally rectangular cross-section. However, it is also contemplated that the slot 233 could alternatively have another suitable cross-section. The screw member 219 is adapted to be received within the cavity 224 of the base member 218. When the screw member 219 is so received, the head portion 230 abuts the second end 221 of the base member 218. When so received, the combination of the screw member 219 and base member 218 is adapted be at least partially received by the metatarsal articulation member 216, the phalanx articulation member 217, or both and mechanically joined by the locking member 225.

Figure 22:
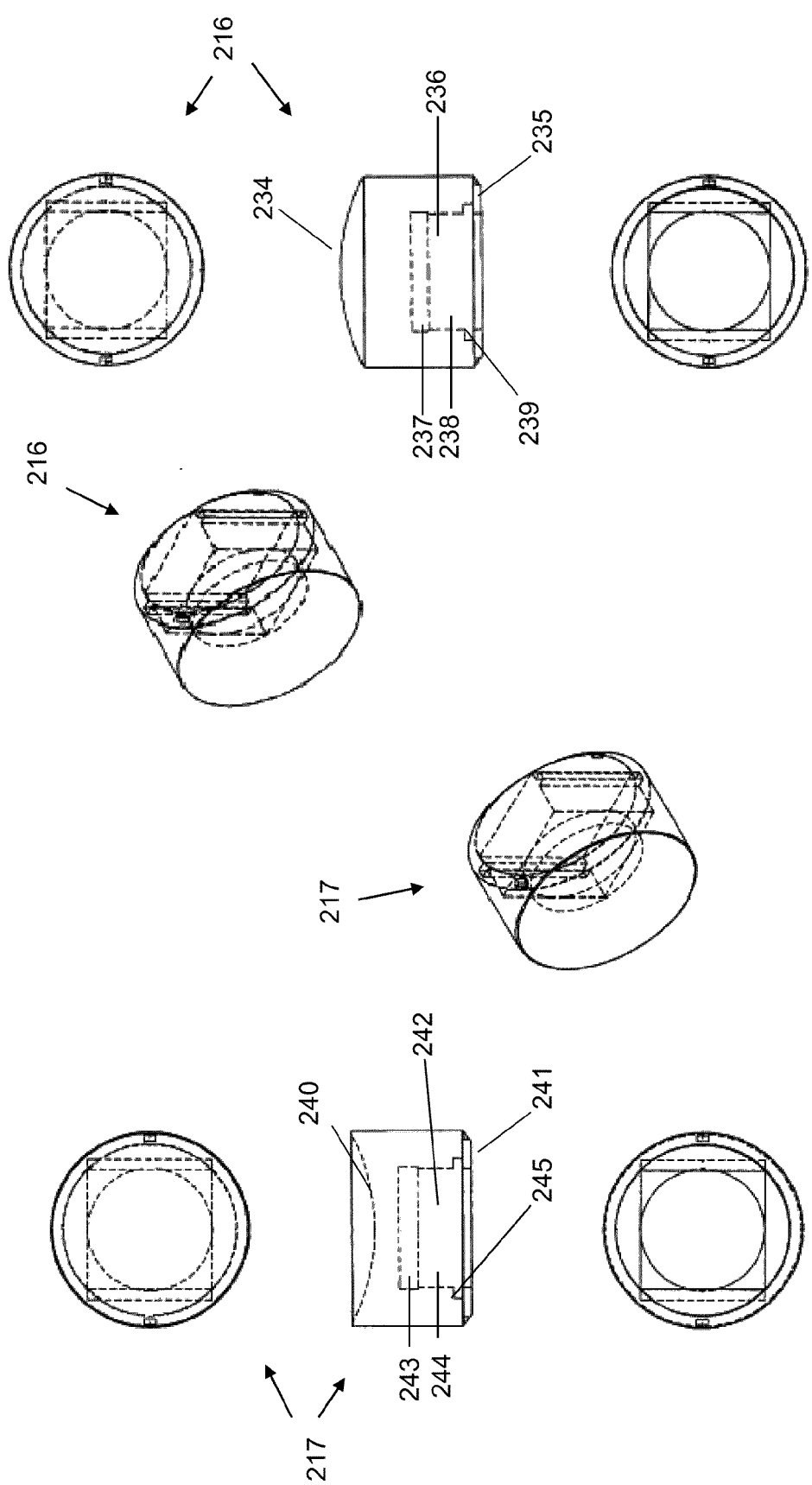

As further illustrated in FIG. 22, the metatarsal articulation member 216 comprises a substantially convex bearing surface 234 and a proximal surface 235 opposite thereto. As shown, the proximal surface 235 is generally planar, but it is also contemplated that it could be non-planar. The bearing surface 234 is adapted to emulate the general shape and function of the head portion of the metatarsal bone within a metatarsophalangeal joint. The metatarsal articulation member 216 also comprises a cavity 236 depressed from the center (not labeled) of the proximal surface 235 and that is adapted to receive at least a portion of the combination of the screw member 219 and base member 218. In some embodiments, the cavity 236 is adapted to receive at least a portion of the head portion 222 of the base member 218 and at least a portion of the head portion 230 of the screw member 219 when the screw member 219 is received within the cavity 223 of the base member 218. The cavity 236 of the metatarsal articulation member 216 comprises a distal portion 237 for receiving at least a portion of the head portion 230 of the screw member 219, a middle portion 238 for receiving the second end 221 and at least a portion of the head portion 222 of the base member 218, and a proximal portion 239 for receiving at least a portion of the flanges of the locking member 225. The distal portion 237 of the cavity 236 has a cross-section that matches that of the head portion 230 of the screw member 219. As shown, the distal portion 237 has a circular cross-section. The middle portion 238 of the cavity 236 has a cross-section that matches that of the second end 221 and at least a portion of the head portion 222 of the base member 218. As shown, the middle portion 238 has a rectangular cross-section. The proximal portion 239 of the cavity 236 comprises at least two opposing slots adapted to receive at least a portion of the opposing flanges of the locking member 225. As shown, the slots of the proximal portion 239 have a rectangular cross-section.

As also illustrated in FIG. 22, the phalanx articulation member 217 comprises a substantially concave bearing surface 240 and a distal surface 241 opposite thereto. As shown, the distal surface 241 is generally planar, but it is also contemplated that it could be non-planar. The bearing surface 240 is adapted to emulate the general shape and function of the proximal portion of the proximal phalanx bone within a metatarsophalangeal joint. The phalanx articulation member 217 also comprises a cavity 242 depressed from the center (not labeled) of the distal surface 241 and that is adapted to receive at least a portion of the combination of the screw member 219 and base member 218. In some embodiments, the cavity 242 is adapted to receive at least a portion of the head portion 222 of the base member 218 and at least a portion of the head portion 230 of the screw member 219 when the screw member 219 is received within the cavity 223 of the base member 218. The cavity 242 of the phalanx articulation member 217 comprises a proximal portion 243 for receiving at least a portion of the head portion 230 of the screw member 219, a middle portion 244 for receiving the second end 221 and at least a portion of the head portion 222 of the base member 218, and a distal portion 245 for receiving at least a portion of the flanges of the locking member 225. The proximal portion 243 of the cavity 242 has a cross-section that matches that of the head portion 230 of the screw member 219. As shown, the distal portion 243 has a circular cross-section. The middle portion 244 of the cavity 242 has a cross-section that matches that of the second end 221 and at least a portion of the head portion 222 of the base member 218. As shown, the middle portion 244 has a rectangular cross-section. The distal portion 245 of the cavity 242 comprises at least two opposing slots adapted to receive at least a portion of the opposing flanges of the locking member 225. As shown, the slots of the distal portion 245 have a rectangular cross-section.

In some embodiments, at least a portion of the metatarsal articulation member 216, at least a portion of the flanges of the locking member 225, or combinations thereof are suitably flexible such that the flanges 225 may be received within the proximal portion 239 of the cavity 236 of the articulation member 216 to mechanically join the articulation member 216 with the base member 218. In some embodiments, at least a portion of the phalanx articulation member 217, at least a portion of the flanges of the locking member 225, or combinations thereof are suitably flexible such that the flanges may be received within the distal portion 245 of the cavity 242 of the articulation member 217 to mechanically join the articulation member 217 with the base member 218.

In some embodiments of assembly, at least the first end 220 and body portion 223 of the base member 218 are first implanted within the resected portion of the bone. Then the first end 228 of the screw member 219 is inserted in and, using a tool that fits the slot 233 of the screw member 219, screwed through the second end 221 and head portion 222 of the base member 218, thereby causing the body portion 223 of the base member 218 to expand with sufficient force to fix the base member 218 and screw member 219 within the bone. When so fixed, the head portion 230 of the screw member 219 abuts the second end 221 of the base member 218. Next, either the metatarsal articulation member 216 or the phalanx articulation member 217 is placed over the combined locking head portion 230, base second end 221, and base head portion 222 in an orientation allowing the flanges of the locking member 225 to be received within the slots 239 or 245 of the chosen articulation member 216 or 217. Finally, sufficient force is applied to the chosen articulation member 216 or 217 to cause at least a portion of the articulation member 216 or 217, the locking member 225, or combinations thereof to resiliently flex from a first to a second position to allow the flanges to be received within the slots 239 or 245, and then from a second to a first position as the flanges are received within the slots 239 or 245. Alternatively, it is contemplated that at least a portion of the articulation member 216 or 217, the locking member 225, or combinations thereof may resiliently flex from the second to an intermediate third configuration as the flanges are received within the slots 239 or 245. When the flanges are received within the slots 239 or 245, the chosen articulation member 216 or 217 is mechanically joined to the base member 218. In some embodiments, the chosen articulation member 216 or 217 is permanently joined to the base member 218.

Figure 23:
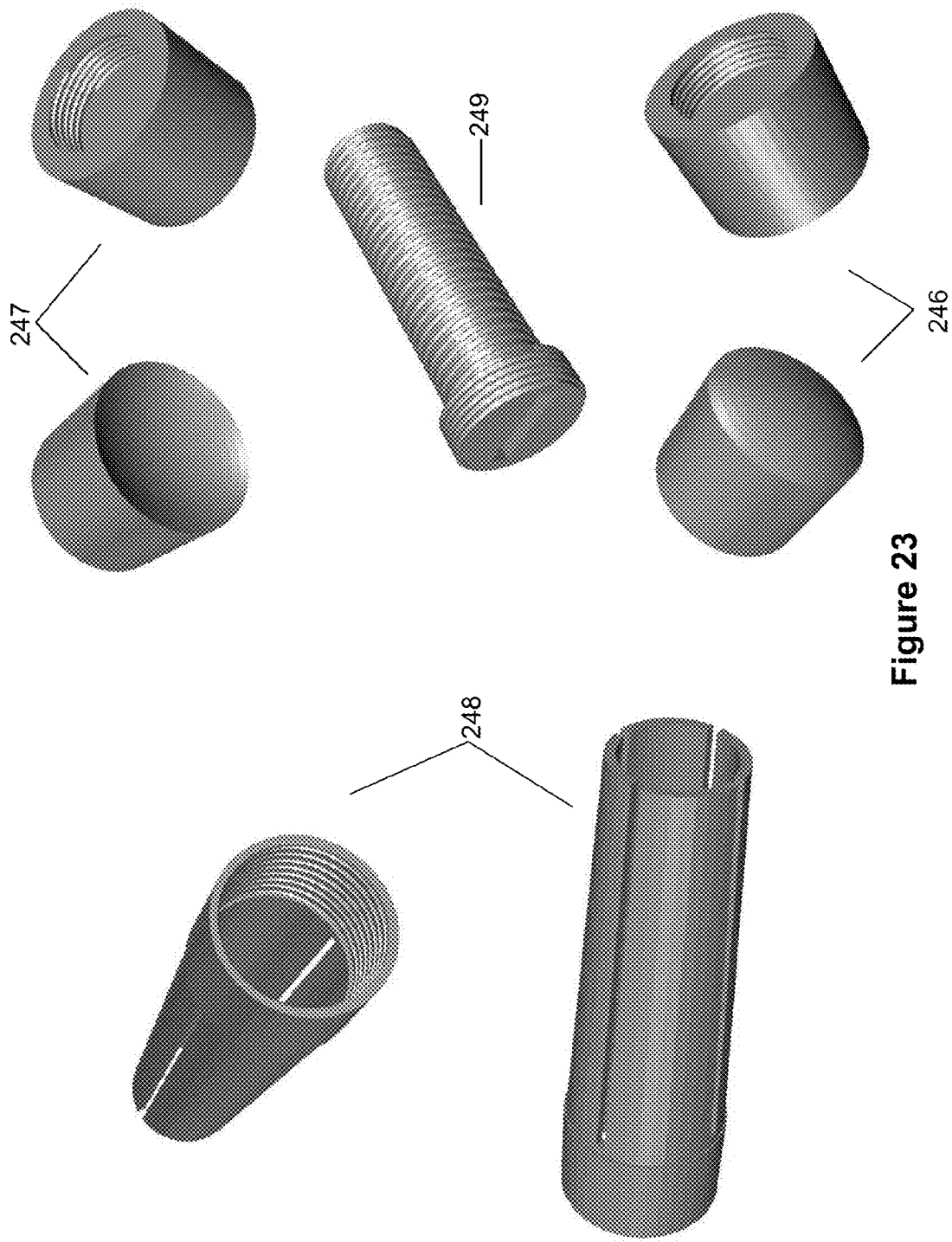
FIGS. 23-25 illustrate an additional example of an implantable two-component device and elements thereof.
Figure 24:
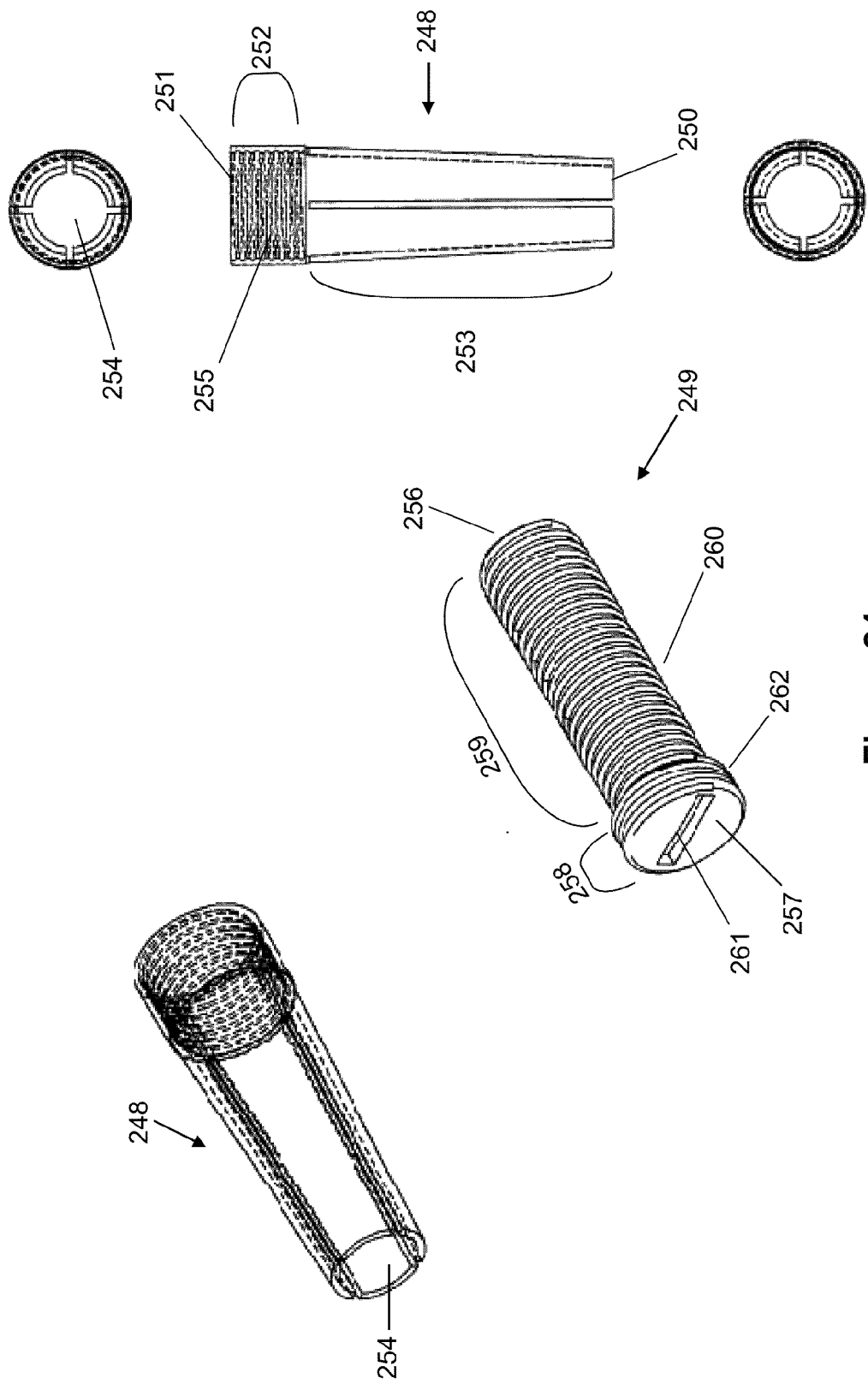
Figure 25:
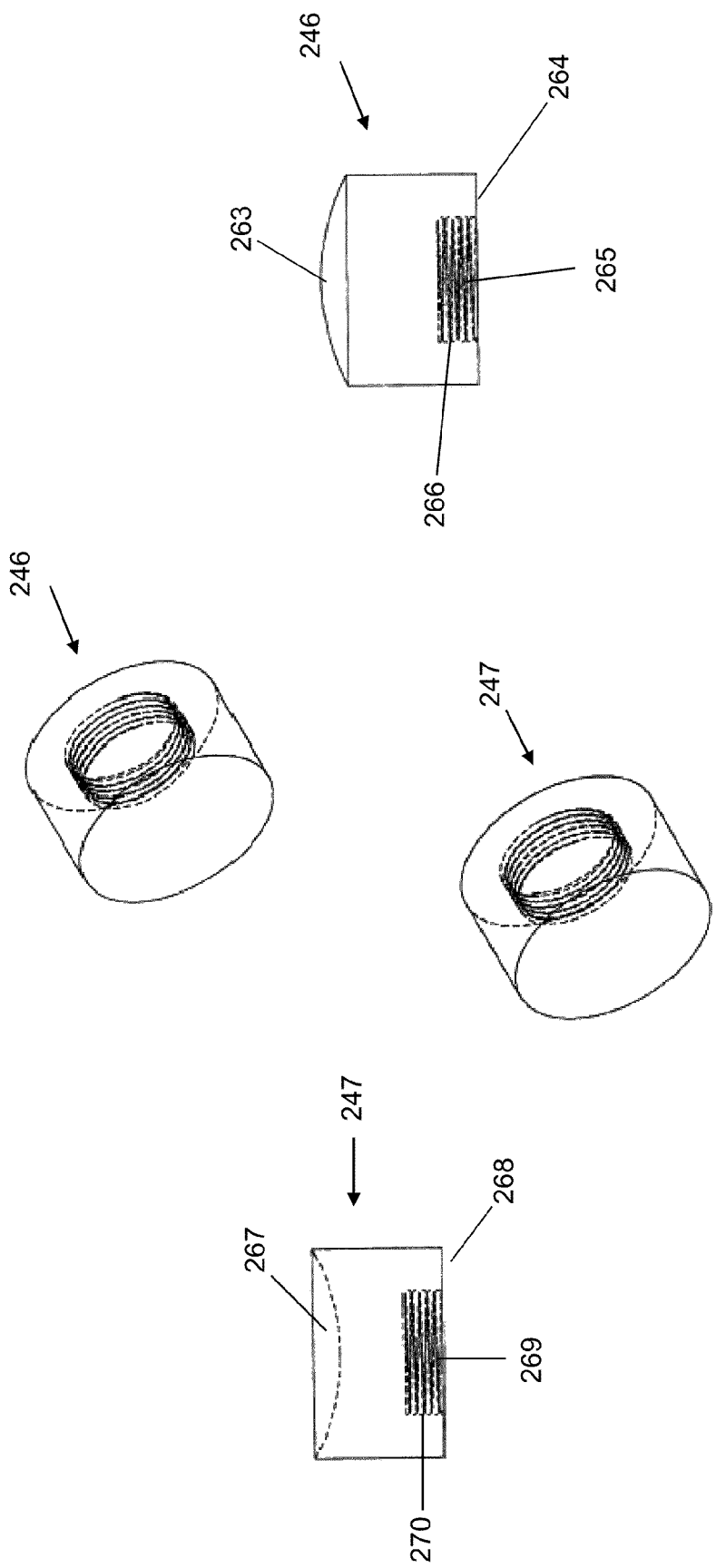

Referring to FIGS. 23-25, illustrated is one example of a device comprising a metatarsal articulation member 246, a phalanx articulation member 247, a base member 248, and a locking member 249. The device may be utilized as a single (hemi) component implant or as a two-component (total) implant. The base member 248 is designed to be implanted into the distal end of a resected metatarsal bone, the proximal end of a resected proximal phalanx bone, or both. The base member 248 may be of any suitable length and dimension to allow for fixation within the metatarsal and phalanx bones, and may be fixed by any medically suitable means. In some embodiments, the base member 248 is designed to be implanted in approximately one third of the length of the metatarsal bone or half of the length of the phalanx bone. In some embodiments, it is designed to be fixed by tension on the interior cavity of the resected bone. When the metatarsal-implanted base member 248 is mechanically joined to the metatarsal articulation member 246 with the locking member 249, the device is designed to replace all or a portion of the metatarsal head and function as the metatarsal component of the metatarsophalangeal joint. When the phalanx-implanted base member 248 is mechanically joined to the phalanx articulation member 247 with the locking member 249, the device is designed to replace all or a portion of the proximal end of the proximal phalanx and function as the phalanx component of the metatarsophalangeal joint.

In some embodiments, the device may be implanted into one or both of the metatarsal and phalanx bones in a primary resectional arthroplasty procedure, in a revision arthroplasty procedure performed to replace or compensate for a failed implant, or combinations thereof. In some embodiments, implantation is by a revision arthroplasty procedure. In some embodiments, each device implanted may be selected from small, medium, or large sizes as necessary to approximate the anatomy of the subject. In some embodiments, the devices may comprise one or more dimensions set forth in Table 7. In some embodiments, each device and elements thereof may be customized to the anatomy of the subject.

TABLE 7

| Metatarsal and Phalanx | Dimension (mm) |
| --- | --- |
| Base Member Length Metatarsal | 22-26 |
| Base Member Length Phalange | 18-22 |
| Locking Member Length Metatarsal | 22-26 |
| Locking Member Length Phalange | 18-22 |
| Locking Member Head Height | 2 |
| Locking Member Head Diameter | 9-10 |
| Articulation Member Height (Excluding Bearing Surface) | 10 |
| Articulation Member Dome Diameter | 16-22 |
| Phalanx Bearing Surface Depth | 2 |
| Metatarsal Bearing Surface Height | 2 |

A further illustrated in FIG. 24, the base member 248 comprises a first end 250, a second end 251 comprising a head portion 252, a body portion 253, and a cavity 254 for receiving the locking member 249. As shown, the first 250 and second 251 ends are non-continuous. The cavity 254 is continuous through the base member 248 from the first end 250 to the second end 251. As shown, the cavity 254 and body portion 253 are conical or tapered and have a generally non-continuous cross-section with a generally circular shape. It is, however, contemplated that the cavity 254 and body portion 253 could alternatively be non-conical or non-tapered, have another suitable cross-section, or combinations thereof, provided that other elements of the device are also adapted to fit such alternatives. For example, a cross-section could be selected from generally elliptical, square, or other suitable shape. In some embodiments, the body portion 253 may be a resilient member adapted to be received within the interior cavity of a resected bone, wherein the body portion 253 expands in response to the locking member 249 being received and advanced through the cavity 254 and exerts sufficient tension on the cavity of the bone to fix the base member 248 therein. In some embodiments, the body portion 253 may comprise a resilient material suitable for surgical implants.

The head portion 252 has a generally circular cross-section. However, it is also contemplated that a head portion 252 could alternatively have another suitable cross-section, provided that other elements of the device are also adapted to fit such alternatives. For example, a head portion 252 could have a cross-section selected from generally elliptical, square, or other suitable shape. The head portion 252 also comprises an interior (female) screw thread 255 along the portion of the cavity 254 formed within the head portion 252, said screw thread 255 adapted to receive a portion of the locking member 249.

As shown, the locking member 249 is a screw member comprising a first end 256, a second end 257 comprising a head portion 258, and a body portion 259 comprising an external (male) screw thread 260. The screw thread 260 is adapted to be at least partially received by the interior screw thread 255 of the base member 248. The locking member 249 is generally cylindrical and has a generally circular cross-section. However, it is also contemplated that the locking member 249 could alternatively be non-cylindrical, have a different cross-section, or combinations thereof, provided that other elements of the device are correspondingly adapted. For example, a locking member 249 could be tapered or conical or have a helical cross-section. The head portion 258 of the locking member 249 has a cross-section larger than that of the body portion 259. Additionally, the head portion 258 comprises a slot 261 centrally positioned on the second end 257 and an external (male) screw thread 262. The screw thread 262 is adapted to be at least partially received by a portion of the metatarsal articulation member 246, phalanx articulation member 247, or both. As shown, the slot 261 has a generally rectangular cross-section. However, it is also contemplated that the slot 261 could alternatively have another suitable cross-section. The locking member 249 is adapted to be received within the cavity 254 of the base member 248. When the locking member 249 is so received, the head portion 258 abuts the second end 251 of the base member 248. It is also contemplated that the head portion 258 could be spaced from the second end 251 when so received. The combination of the locking member 249 and base member 248 is adapted be at least partially received by the metatarsal articulation member 246, the phalanx articulation member 247, or both.

As further illustrated in FIG. 25, the metatarsal articulation member 246 comprises a substantially convex bearing surface 263 and a proximal surface 264 opposite thereto. As shown, the proximal surface 264 is generally planar, but it is also contemplated that it could be non-planar. The bearing surface 263 is adapted to emulate the general shape and function of the head portion of the metatarsal bone within a metatarsophalangeal joint. The metatarsal articulation member 246 also comprises a cavity 265 depressed from the center (not labeled) of the proximal surface 264. The cavity 265 comprises an interior (female) screw thread 266 adapted to receive at least a portion of the external screw thread 262 of the head portion 258 of the locking member 249. In some embodiments, all of the head portion 258 may be received within the cavity 265. The cavity 265 has a cross-section that matches that of the head portion 258 of the locking member 249. As shown, the cavity 265 has a circular cross-section.

As additionally illustrated in FIG. 25, the phalanx articulation member 247 comprises a substantially concave bearing surface 267 and a distal surface 268 opposite thereto. As shown, the distal surface 268 is generally planar, but it is also contemplated that it could be non-planar. The bearing surface 267 is adapted to emulate the general shape and function of the proximal portion of the proximal phalanx bone within a metatarsophalangeal joint. The phalanx articulation member 247 also comprises a cavity 269 depressed from the center (not labeled) of the distal surface 268. The cavity 269 comprises an interior (female) screw thread 270 adapted to receive at least a portion of the external screw thread 262 of the head portion 258 of the locking member 249. In some embodiments, all of the head portion 258 may be received within the cavity 269. The cavity 269 has a cross-section that matches that of the head portion 258 of the locking member 249. As shown, the cavity 269 has a circular cross-section.

In some embodiments of assembly, at least the first end 250 and body portion 253 of the base member 248 are first implanted within the resected portion of the bone. Then the first end 256 of the locking member 249 is inserted in and, using a tool that fits the slot 261 of the locking member 249, screwed through the second end 251 and head portion 252 of the base member 248, thereby causing the body portion 253 of the base member 248 to expand with sufficient force to fix the base member 248 and locking member 249 within the bone cavity. When so fixed, the head portion 258 of the locking member 249 abuts or is proximate to the second end 251 of the base member 248. Next, either the metatarsal articulation member 246 or the phalanx articulation member 247 is placed over the head portion 258 of the locking member 249 such that the head portion 258 may be received within the cavity 265 or 269 of the chosen articulation member 246 or 247. Finally, the chosen articulation member 246 or 247 is screwed onto the head portion 258 of the locking member 249 to mechanically join the articulation member chosen 246 or 247 with the base member 248.

Figure 26:
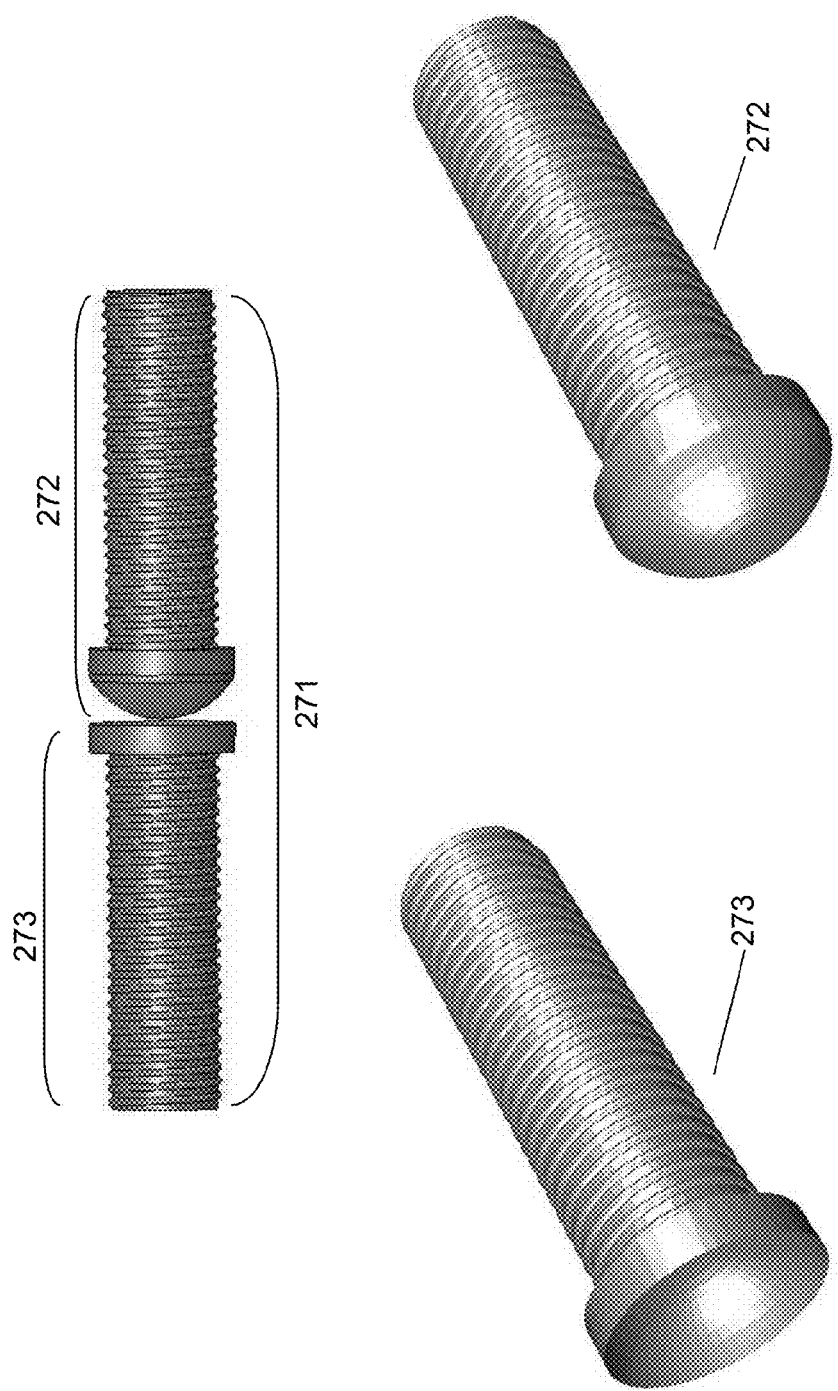
FIGS. 26-27 illustrate a further example of an implantable two-component device and elements thereof.
Figure 27:
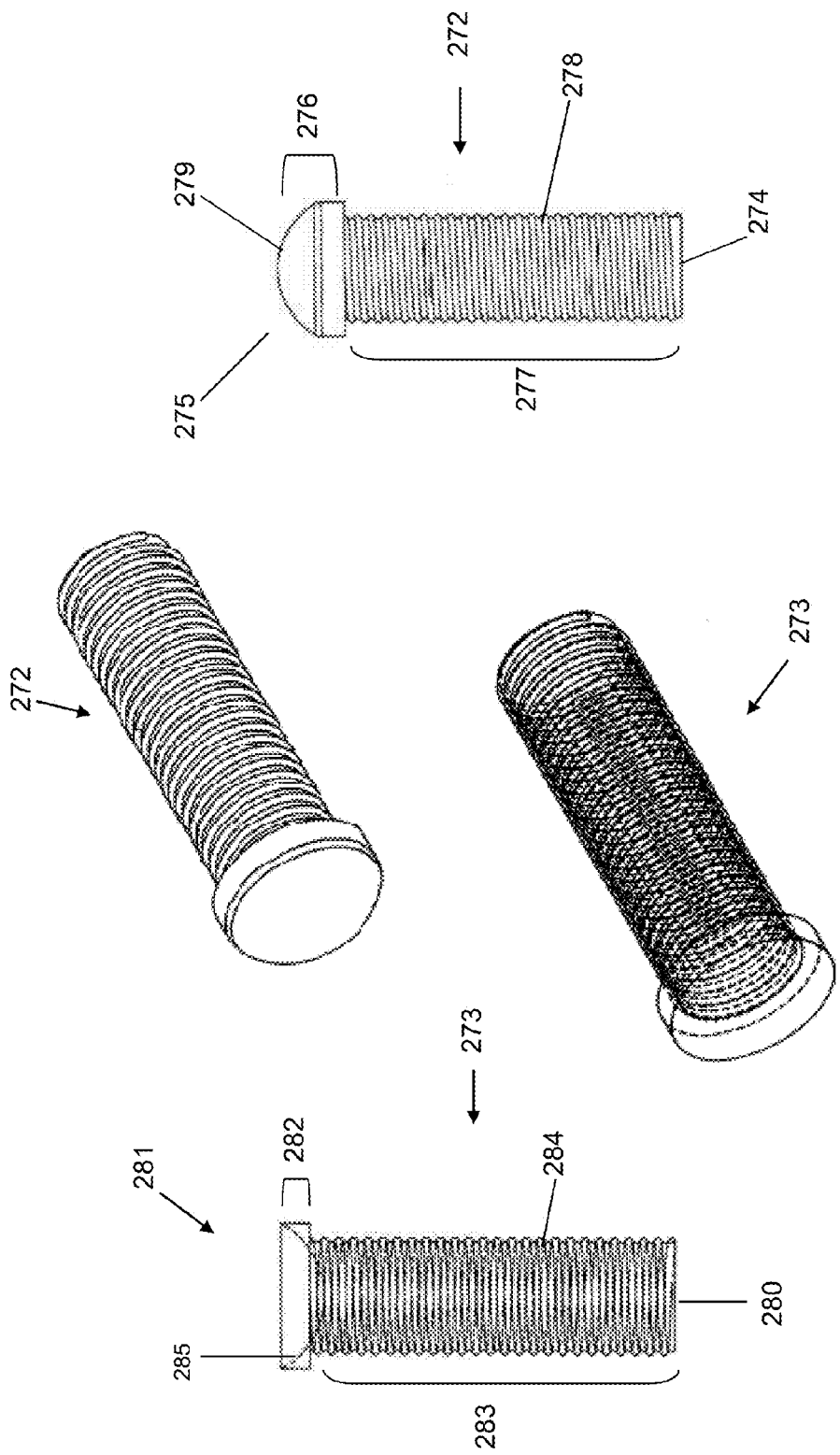

Referring to FIGS. 26-27, illustrated is an example of an implantable device of the invention which is designed to replace all or a portion of a metatarsophalangeal joint. Such device comprises one or more of: (i) a metatarsal component for surgical implantation into the distal end of a metatarsal bone, comprising a metatarsal articulation member comprising a substantially convex bearing surface; and a locking member comprising a screw thread adapted to fix the metatarsal component in the metatarsal bone; and (ii) a phalanx component for surgical implantation into the proximal end of a proximal phalanx bone, comprising a phalanx articulation member comprising a substantially concave bearing surface; and a locking member comprising a screw thread adapted to fix the phalanx component in the phalanx bone.

In those embodiments wherein one of the components is implanted, the chosen component is adapted to cooperatively engage with and move with respect to either the proximal end of the proximal phalanx bone or the distal end of the metatarsal bone. In those embodiments wherein both of the components are implanted, the metatarsal component and the phalanx component are adapted to cooperatively engage such that the metatarsal articulation member and the phalanx articulation member move with respect to each other and collectively serve as a prosthetic metatarsophalangeal joint.

As illustrated in FIG. 26, the two-component device 271 comprises a metatarsal component 272 designed to be implanted into the distal end of a resected metatarsal bone, and a phalanx component 273 designed to be implanted into the proximal end of a resected proximal phalanx bone. The metatarsal component 272 may be of any suitable length and dimension to allow for fixation within the metatarsal bone, and may be fixed by any medically suitable means. In some embodiments, the metatarsal component 272 is designed to be implanted in approximately one third of the length of the metatarsal bone. The phalanx component 273 may be of any suitable length and dimension to allow for fixation within the phalanx bone, and may be fixed by any medically suitable means. In some embodiments, the phalanx component 273 is designed to be implanted in approximately half of the length of the phalanx bone.

In some embodiments, the components 272, 273 may be implanted into one or both of the metatarsal and phalanx bones in a primary resectional arthroplasty procedure, in a revision arthroplasty procedure performed to replace or compensate for a failed implant, or combinations thereof. In some embodiments, implantation is by a primary arthroplasty procedure. In some embodiments, each device implanted may be selected from small, medium, or large sizes as necessary to approximate the anatomy of the subject. In some embodiments, the components 272, 273 may comprise one or more dimensions set forth in Table 8. In some embodiments, each device and elements thereof may be customized to the anatomy of the subject.

TABLE 8

| Metatarsal and Phalanx | Dimension (mm) |
| --- | --- |
| Total Length Metatarsal | 22-26 |
| Total Length Phalange | 18-22 |
| Locking Member Length Metatarsal | 22-26 |
| Locking Member Length Phalange | 18-22 |
| Locking Member Head Height | 2 |
| Screw Head Diameter | 10-13 |
| Articulation Member Height (Excluding Bearing Surface) | 10 |
| Phalanx Bearing Surface Depth | 3 |
| Metatarsal Bearing Surface Height | 3 |

As further illustrated in FIG. 27, the metatarsal component 272 comprises a first end 274, a second end 275 comprising a metatarsal articulation member 276, and a locking member 277 comprising an external (male) screw thread 278. The screw thread 278 is adapted to be at least partially received within, and fix the metatarsal component 272 to, a resected distal end of a metatarsal bone. The locking member 277 is generally cylindrical and has a generally circular cross-section. However, it is also contemplated that the locking member 277 could alternatively be non-cylindrical, have a different cross-section, or combinations thereof. For example, a locking member 277 could be tapered or conical or have a helical cross-section. The articulation member 276 of the metatarsal component 272 has a cross-section larger than that of the locking member 277. Additionally, the metatarsal articulation member 276 comprises a substantially convex bearing surface 279. The bearing surface 279 is adapted to emulate the general shape and, when implanted into the resected metatarsal bone, function of the head portion of the metatarsal bone within a metatarsophalangeal joint.

As additionally illustrated in FIG. 27, the phalanx component 273 comprises a first end 280, a second end 281 comprising a phalanx articulation member 282, and a locking member 283 comprising an external (male) screw thread 284. The screw thread 284 is adapted to be at least partially received within, and fix the phalanx component 273 to, a resected proximal end of a proximal phalanx bone. The locking member 283 is generally cylindrical and has a generally circular cross-section. However, it is also contemplated that the locking member 283 could alternatively be non-cylindrical, have a different cross-section, or combinations thereof. For example, a locking member 283 could be tapered or conical or have a helical cross-section. The articulation member 282 of the phalanx component 273 has a cross-section larger than that of the locking member 283. Additionally, the phalanx articulation member 282 comprises a substantially concave bearing surface 285. The bearing surface 285 is adapted to emulate the general shape and, when implanted into the resected proximal phalanx bone, function of the proximal portion of the proximal phalanx bone within a metatarsophalangeal joint.

In some embodiments of operation, at least the first end 274 and locking member 277 of the metatarsal component 272 are inserted in and screwed into the distal end of a resected metatarsal bone. In some embodiments, at least all of the locking member 277 is screwed into the metatarsal bone. In some embodiments, all of the locking member 277 and at least a portion of the metatarsal articulation member 276 are implanted into the metatarsal bone. In some embodiments, a portion ("screw head") of the metatarsal articulation member 276 proximate to the locking member 277 may be received within the resected bone. In some embodiments of operation, at least the first end 280 and locking member 283 of the phalanx component 273 are inserted in and screwed into the proximal end of a resected proximal phalanx bone. In some embodiments, at least all of the locking member 283 is screwed into the proximal phalanx bone. In some embodiments, all of the locking member 283 and at least a portion of the phalanx articulation member 282 are implanted into the proximal phalanx bone. In some embodiments, a portion ("screw head") of the phalanx articulation member 282 proximate to the locking member 283 may be received within the resected bone.

Figure 28:
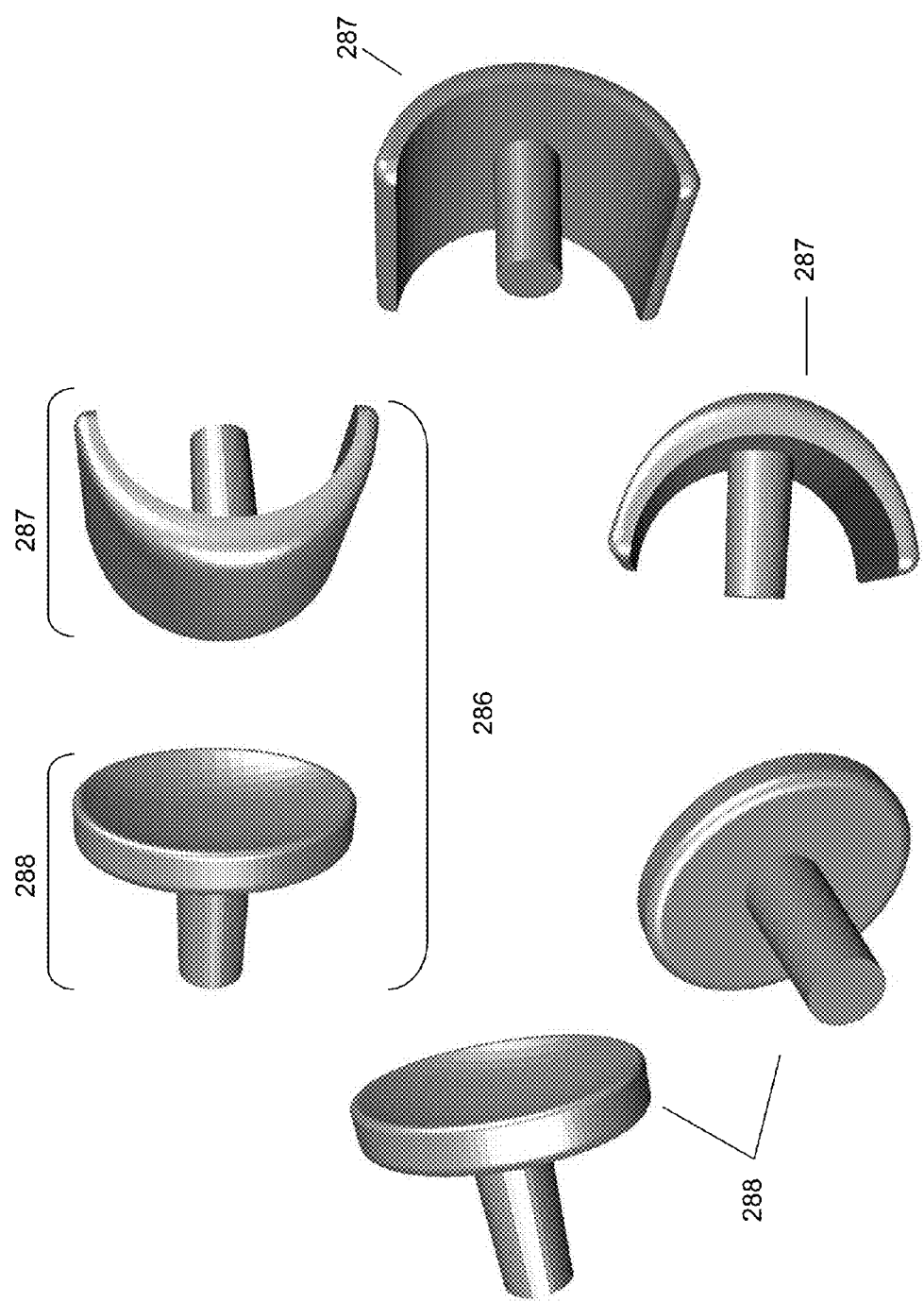
FIGS. 28-30 also illustrate one example of an implantable two-component device and elements thereof.
Figure 29:
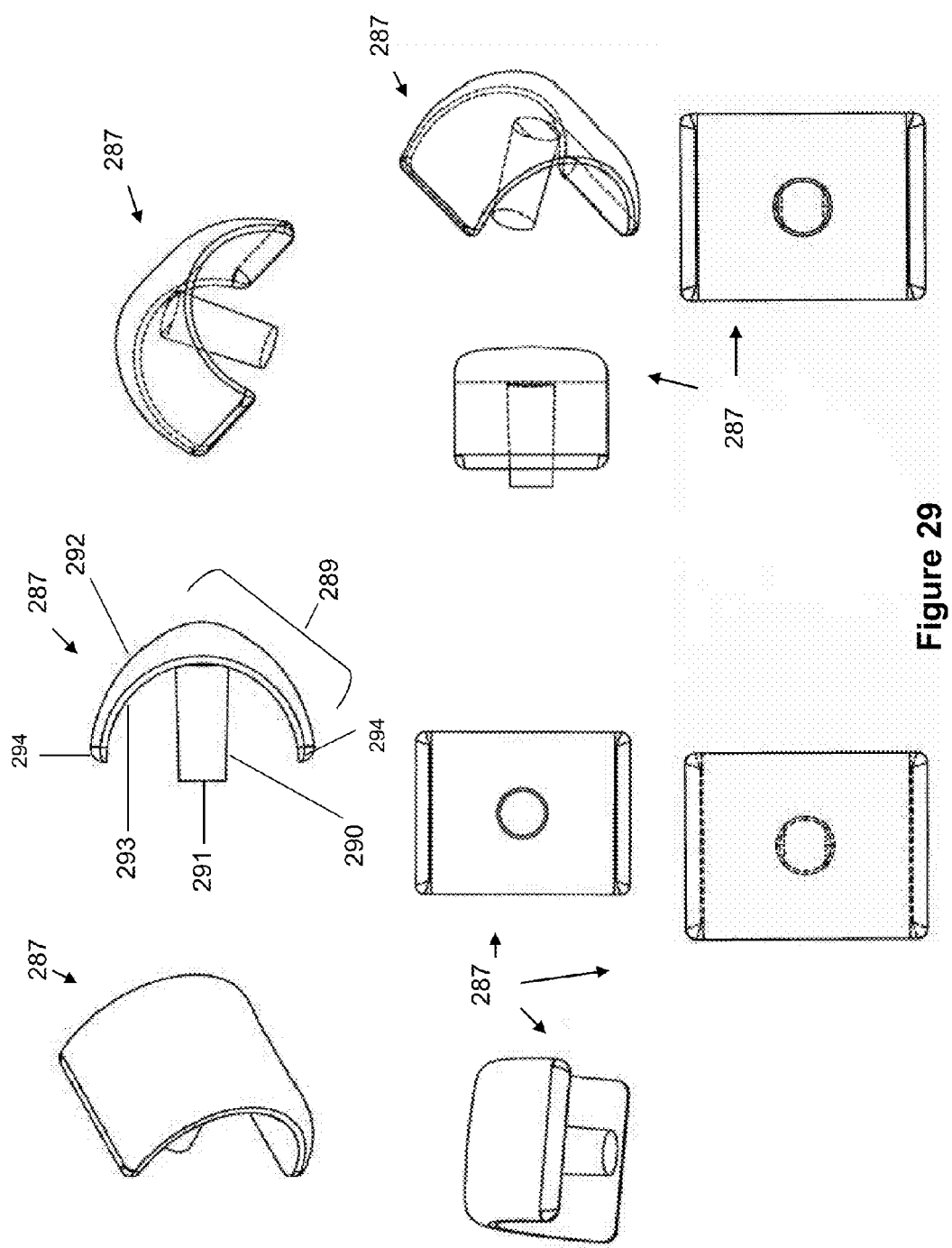
Figure 30:
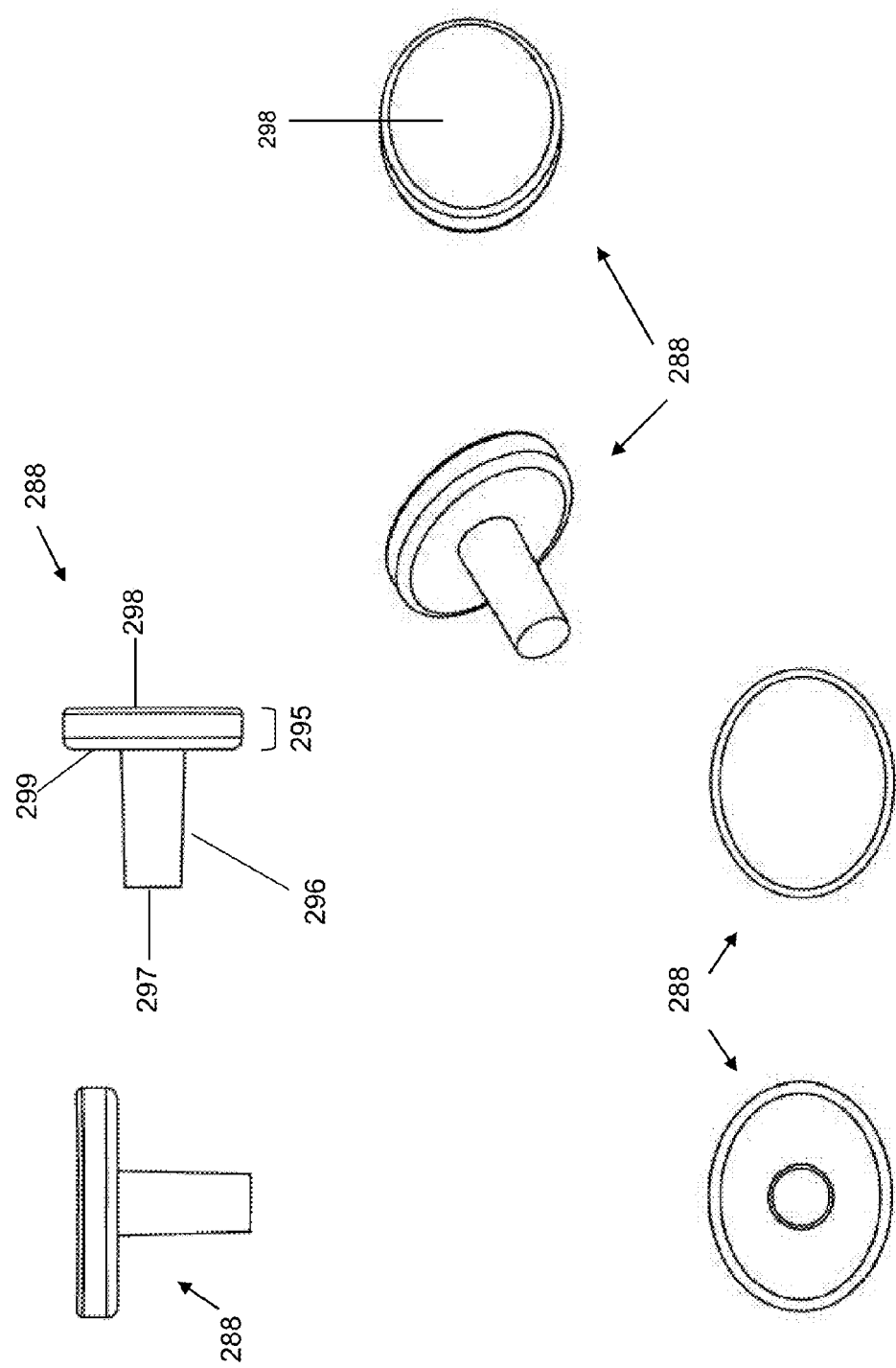
Figure 31:
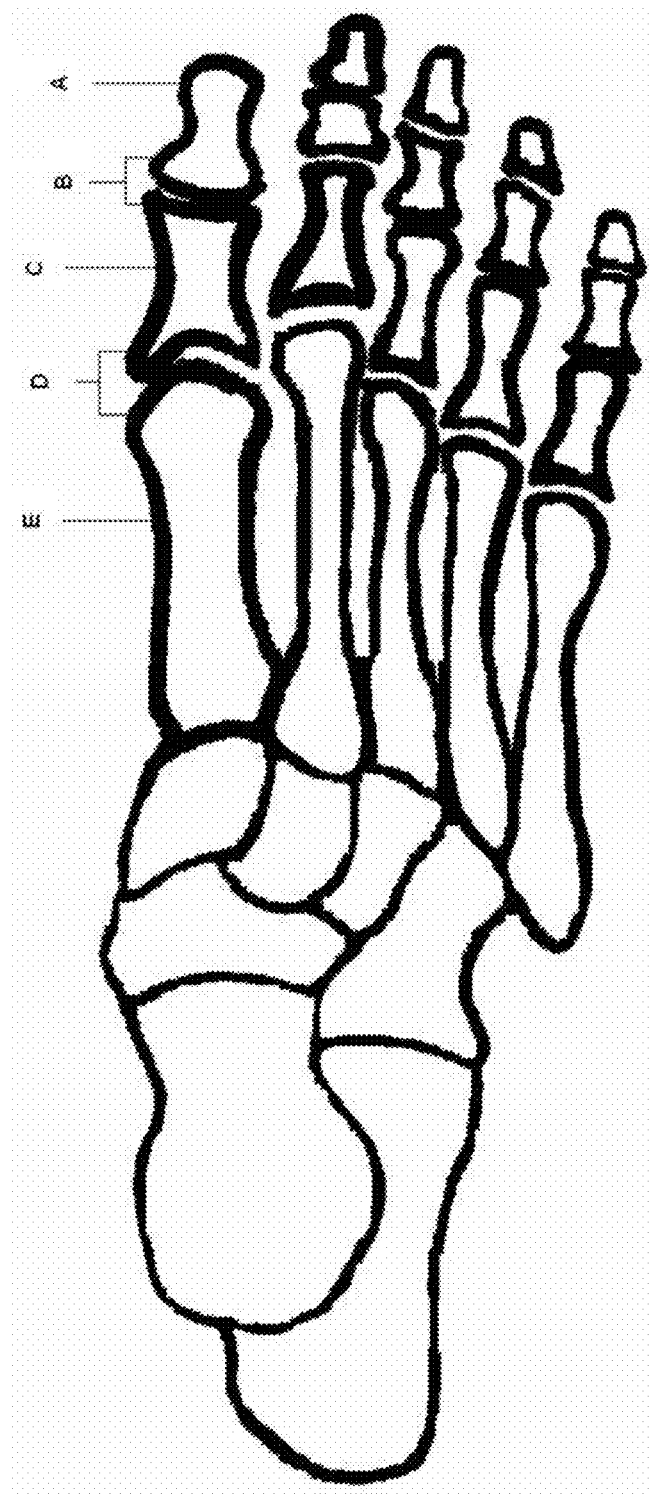
FIG. 31 illustrates the bones of the foot, including those most relevant to hallux valgus: A, distal phalanx; B, interphalangeal joint; C, proximal phalanx; D, metatarsophalangeal joint; E, metatarsal.
Figure 32:
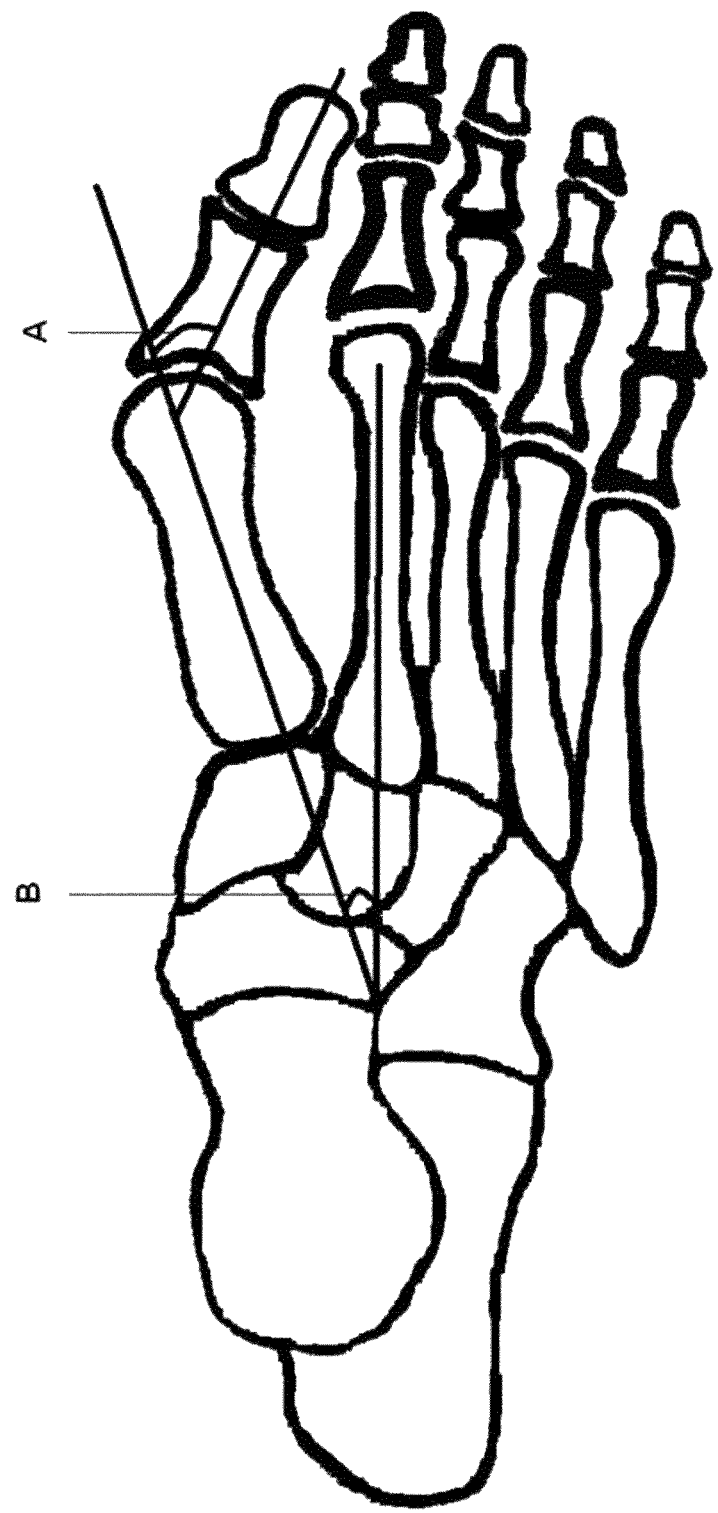
FIG. 32 illustrates deformity of the A, hallux valgus angle; and B, intermetatarsal angle. In various embodiments, the provided implants are designed to correct one or both angles in a subject foot.

Referring to FIGS. 28-30, illustrated is an example of an implantable device of the invention which is designed to replace all or a portion of a metatarsophalangeal joint. Such device comprises one or more of: (i) a metatarsal component for surgical implantation into the distal end of a metatarsal bone, comprising a metatarsal articulation member comprising a substantially convex parabolic bearing surface terminating at equidistantly positioned ends; and (ii) a phalanx component for surgical implantation into the proximal end of a proximal phalanx bone, comprising a phalanx articulation member comprising a substantially concave bearing surface.

In those embodiments wherein one of the components is implanted, the chosen component is adapted to cooperatively engage with and move with respect to either the proximal end of the proximal phalanx bone or the distal end of the metatarsal bone. In those embodiments wherein both of the components are implanted, the metatarsal component and the phalanx component are adapted to cooperatively engage such that the metatarsal articulation member and the phalanx articulation member move with respect to each other and collectively serve as a prosthetic metatarsophalangeal joint.

As illustrated, the two-component device 286 comprises a metatarsal component 287 and a phalanx component 288. The metatarsal component 287 is designed to be implanted into the distal end of a resected metatarsal bone to replace all or a portion of the metatarsal head and function as the metatarsal component of the metatarsophalangeal joint. The phalanx component 288 is designed to be implanted into the proximal end of the proximal phalanx and function as the phalanx component of the metatarsophalangeal joint.

In some embodiments, the components 287, 288 may be implanted into one or both of the metatarsal and phalanx bones in a primary resectional arthroplasty procedure, in a revision arthroplasty procedure performed to replace or compensate for a failed implant, or combinations thereof. In some embodiments, implantation is by a revision arthroplasty procedure. In some embodiments, each device implanted may be selected from small, medium, or large sizes as necessary to approximate the anatomy of the subject. In some embodiments, the components 287, 288 may comprise one or more of the dimensions set forth in Table 9. In some embodiments, each device and elements thereof may be customized to the anatomy of the subject.

TABLE 9

| | Dimension (mm) |
|---|---|
| Metatarsal | |
| Stem Length | 10-11 |
| Stem Diameter | 5-6 |
| Articulation Member Width | 18-19 |
| Articulation Member Diameter | 12-14 |
| Phalanx | |
| Stem Length | 10-11 |
| Stem Diameter | 5-6 |
| Articulation Member Height | 16-18 |
| Articulation Member Width | 20-21 |
| Articulation Member Diameter | 12-14 |

In some embodiments, the material of composition of the components 287, 288 is pyrocarbon. In some embodiments, the material of composition is pyrocarbon having a coating to enhance bone growth. In some embodiments, the coating is titanium plasma spray.

As further illustrated in FIG. 29, the metatarsal component 287 comprises a metatarsal articulation member 289, a stem 290, and a proximal end 291. The metatarsal articulation member 289 comprises a substantially convex bearing surface 292 having a parabolic cross-section and a proximal surface 293 opposite thereto. In some embodiments, the proximal surface 293 has a semi-circular cross-section. However, alternative cross-sections are also contemplated. For example, semi-elliptical, semi-oval, or parabolic cross-sections. In some embodiments, the convex bearing surface 292 and proximal surface 293 comprise shared ends 294 that are equidistantly positioned with respect to each other. In some embodiments, the ends 294 are equidistantly position with respect to each other and the stem 290. The bearing surface 292 is adapted to emulate the general shape and function as the head portion of the metatarsal bone within a metatarsophalangeal joint.

The stem 290 protrudes from the center (not labeled) of the proximal surface 293, terminates at the proximal end 291, and is adapted to be received within a resected metatarsal bone. As shown, the stem 290 is conical or tapered and has a circular cross-section. In some embodiments, the stem 290 is tapered and has a taper angle of from about 0-10°. However, it is also contemplated that the stem 290 could alternatively be non-conical or non-tapered, have another suitable cross-section, or combinations thereof. For example, a stem 290 could be cylindrical, have a cross-section selected from generally elliptical, square, triangular, or other suitable shape, or combinations thereof. The stem 290 may be of any suitable length and dimension to allow for fixation within the metatarsal bone, and may be fixed by any medically suitable means. In some embodiments, the stem 290 is designed to be implanted in approximately one third of the length of the metatarsal bone. In some embodiments, it may be fixed with bone cement.

In some embodiments of operation, the proximal end 291 and at least a portion of the stem 290 of the metatarsal component 287 are implanted into the distal end of a resected metatarsal bone. In some embodiments of operation, the proximal end 291 and the entire stem 290 are implanted such that the proximal surface 293 abuts the distal end of the resected metatarsal bone. In some embodiments, the metatarsal component 287 is designed to be implanted without a washer or other spacer means between the proximal surface 293 and the bone.

As further illustrated in FIG. 30, the phalanx component 288 comprises a phalanx articulation member 295, a stem 296, and a distal end 297. The phalanx articulation member 295 comprises a substantially concave bearing surface 298 and a distal surface 299 opposite thereto. As shown, the distal surface 299 is generally planar, but it is also contemplated that it could be non-planar. Moreover, as shown, the phalanx articulation member 295 has a generally elliptical cross-section. It is contemplated, however, that it could have another suitable cross-section, provided that the metatarsal component 287 is correspondingly adapted to enable cooperative engagement. The bearing surface 298 is adapted to emulate the general shape and function as the proximal portion of the proximal phalanx bone within a metatarsophalangeal joint. The stem 296 protrudes from the center (not labeled) of the distal surface 299, terminates at the distal end 297, and is adapted to be received within a resected proximal phalanx bone. As shown, the stem 296 is conical or tapered and has a circular cross-section. In some embodiments, the stem 296 is tapered and has a taper angle of from about 0-10°. However, it is also contemplated that the stem 296 could alternatively be non-conical or non-tapered, have another suitable cross-section, or combinations thereof. For example, a stem 296 could be cylindrical, have a cross-section selected from generally elliptical, square, triangular, or other suitable shape, or combinations thereof. The stem 296 may be of any suitable length and dimension to allow for fixation within the phalanx bone, and may be fixed by any medically suitable means. In some embodiments, the stem 296 is designed to be implanted in approximately half of the length of the phalanx bone. In some embodiments, it may be fixed with bone cement.

In some embodiments of operation, the distal end 297 and at least a portion of the stem 296 of the phalanx component 288 are implanted into the proximal end of a resected proximal phalanx bone. In some embodiments of operation, the distal end 297 and the entire stem 296 are implanted such that the distal surface 299 abuts the proximal end of the resected proximal phalanx bone. In some embodiments, the phalanx component 288 is designed to be implanted without a washer or other spacer means between the distal surface 299 and the bone.

In various embodiments, provided are methods of treating hallux valgus, comprising replacing all or a portion of a metatarsophalangeal joint with implantable devices selected from: (i) a metatarsal component for surgical implantation into the distal end of a metatarsal bone, comprising a metatarsal articulation member comprising a substantially convex bearing surface; (ii) a phalanx component for surgical implantation into the proximal end of a proximal phalanx bone, comprising a phalanx articulation member comprising a substantially concave bearing surface; or (iii) a metatarsal component for surgical implantation into the distal end of a metatarsal bone, comprising a metatarsal articulation member comprising a substantially convex bearing surface; and a phalanx component for surgical implantation into the proximal end of a proximal phalanx bone, comprising a phalanx articulation member comprising a substantially concave bearing surface. In some embodiments, the provided methods may be used to correct one or more of the hallus valgus angle and the intermetatarsal angle. In some embodiments, the provided methods may be used to provide a subject with alignment and articulation of the metatarsal and proximal phalanx bones in a manner consistent with that of a natural metatarsophalangeal joint. In some embodiments, the provided methods may be performed without complex assembly, positioning, or other manipulation of the implant device by the surgeon. In some embodiments, one or more of the devices illustrated in FIGS. 2-30 and further described herein may be utilized with the provided methods.

What is claimed is:

1. An implantable device, comprising:
   (i) a metatarsal component configured to be surgically implanted into the distal end of a resected metatarsal bone, comprising:
      an articulation member comprising (a) a head portion having a substantially convex bearing surface and a second surface opposite thereto; and (b) a locking member protruding from the second surface in a direction opposite to the bearing surface and terminating at an end portion;
      a base member configured to be fixed within the resected metatarsal bone, the base member comprising (a) a continuous first end; (b) a discontinuous second end opposite thereto; and (c) a cavity configured to receive the locking member, the cavity having a first end recessed within the base member, an opposing second end partially shared with the discontinuous second end of the base member, and a slot integrated into the first end of the cavity;
      wherein the metatarsal component is configured such that when the articulation member and the base member are mechanically joined, the locking member is disposed within the cavity such that the second surface of the articulation member abuts the second end of the base member, and the end portion of the locking member is locked within the slot; and
   (ii) a phalanx component configured to be surgically implanted into the proximal end of a resected proximal phalanx bone, comprising:
      an articulation member comprising (a) a head portion having a substantially concave bearing surface and a second surface opposite thereto; and (b) a locking member protruding from the second surface in a direction opposite to the bearing surface and terminating at an end portion;
      a base member configured to be fixed within the resected proximal phalanx bone, the base member comprising (a) a continuous first end; (b) a discontinuous second end opposite thereto; and (c) a cavity configured to receive the locking member, the cavity having a first end recessed within the base member, an opposing second end partially shared with the discontinuous second end of the base member, and a slot integrated into the first end of the cavity;
      wherein the phalanx component is configured such that when the articulation member and the base member are mechanically joined, the locking member is disposed within the cavity such that the second surface of the articulation member abuts the second end of the base member, and the end portion of the locking member is locked within the slot;
   wherein the metatarsal component and the phalanx component are configured to cooperatively engage when implanted such that the metatarsal articulation member and the phalanx articulation member may move with respect to each other and collectively serve as a prosthetic metatarsophalangeal joint;
      wherein the base member of the metatarsal component, the base member of the phalanx component, or both comprise one or more peripherally positioned flanges running longitudinally along at least a portion of the base member, each flange configured to be received within a cavity of a resected bone, wherein the flanges are flexible spring members that, when inserted into the bone cavity, exert sufficient tension to fix the base member within the bone;
      wherein each of the flanges comprise:
         at least one upper surface positioned proximate the discontinuous second end of the base member and angled directionally outward from the discontinuous second end towards the continuous first end;
         at least one side surface connected to and extending a distance from the upper surface towards the continuous first end of the base member,
         wherein the upper surface of the flange is partially non-contacted with the articulation member when the articulation member and the base member are mechanically joined.

2. A device according to claim 1, wherein the base member of the metatarsal component, the base member of the phalanx component, or both, have a shape selected from cylindrical, conical, or tapered.

3. A device according to claim 1, comprising four equidistantly positioned flanges.

4. A device according to claim 1, wherein each flange has a triangular cross-section and one end positioned in the same plane as the discontinuous second end of the base member.

5. A device according to claim 1, wherein the metatarsal articulation member comprises a neck portion abutting the second surface of the head portion, and a body portion positioned between the neck portion and the end portion.

6. A device according to claim 5, wherein the body portion of the metatarsal articulation member has a square or rectangular shape, and the cavity of the metatarsal base member has a corresponding shape.

7. A device according to claim 6, wherein the end portion of the metatarsal locking member and the slot of the metatarsal base member cavity have a circular cross-section.

8. A device according to claim 1, wherein the phalanx articulation member comprises a neck portion abutting the second surface of the head portion, and a body portion positioned between the neck portion and the end portion.

9. A device according to claim 8, wherein the body portion of the phalanx articulation member has a square or rectangular shape, and the cavity of the phalanx base member has a corresponding shape.

10. A device according to claim 9, wherein the end portion of the phalanx locking member and the slot of the phalanx base member cavity have a circular cross-section.

11. A device according to claim 1, comprising a material of composition selected from ultra-high molecular weight polyethylene, stainless steel, titanium, titanium alloy, chromium-cobalt-molybdenum alloy, pyrocarbon, and combinations thereof.

* * * * *

UNITED STATES PATENT AND TRADEMARK OFFICE
CERTIFICATE OF CORRECTION

PATENT NO. : 9,044,332 B2
APPLICATION NO. : 13/655269
DATED : June 2, 2015
INVENTOR(S) : Tarun K. Goswami et al.

Page 1 of 2

It is certified that error appears in the above-identified patent and that said Letters Patent is hereby corrected as shown below:

In the Specification

Col. 8, Line 29,
 "A further illustrated in FIG. 3, the base member 4 of the" should read
 --As further illustrated in FIG. 3, the base member 4 of the--;

Col. 14, Line 32,
 "A further illustrated in FIG. 7, the base member 44 of the" should read
 --As further illustrated in FIG. 7, the base member 44 of the--;

Col. 21, Line 13,
 "In those embodiment wherein one of the components is" should read
 --In those embodiments wherein one of the components is--;

Col. 22, Line 24,
 "A further illustrated in FIG. 12, the base member 116 of the" should read
 --As further illustrated in FIG. 12, the base member 116 of the--;

Col. 27, Line 11,
 "A further illustrated in FIG. 15, the base member 153 of the" should read
 --As further illustrated in FIG. 15, the base member 153 of the--;

Col. 28, Line 42,
 "A further illustrated in FIG. 16, the base member 155 of the" should read
 --As further illustrated in FIG. 16, the base member 155 of the--;

Col. 30, Line 49,
 "A further illustrated in FIG. 18, the base member 186 of the" should read
 --As further illustrated in FIG. 18, the base member 186 of the--;

Signed and Sealed this
Twenty-ninth Day of March, 2016

Michelle K. Lee
*Director of the United States Patent and Trademark Office*

CERTIFICATE OF CORRECTION (continued)
U.S. Pat. No. 9,044,332 B2

Col. 32, Line 13,
 "A further illustrated in FIG. 19, the base member 188 of the" should read
 --As further illustrated in FIG. 19, the base member 188 of the--;

Col. 34, Line 62,
 "A further illustrated in FIG. 21, the base member 218 of the" should read
 --As further illustrated in FIG. 21, the base member 218 of the--;

Col. 35, Line 54,
 "cylindrical, have an different cross-section, or combinations" should read
 --cylindrical, have a different cross-section, or combinations--;

Col. 36, Line 2,
 "member 218 is adapted be at least partially received by the" should read
 --member 218 is adapted to be at least partially received by the--;

Col. 38, Line 41,
 "A further illustrated in FIG. 24, the base member 248" should read
 --As further illustrated in FIG. 24, the base member 248--;

Col. 39, Line 38,
 "ber 248 is adapted be at least partially received by the meta-" should read
 --ber 248 is adapted to be at least partially received by the meta- --; and Col. 43, Line 38,
 "embodiments, the ends 294 are equidistantly position with" should read
 --embodiments, the ends 294 are equidistantly positioned with--.